US010315039B2

(12) United States Patent
Perryman et al.

(10) Patent No.: US 10,315,039 B2
(45) Date of Patent: Jun. 11, 2019

(54) MICROWAVE FIELD STIMULATOR

(71) Applicant: Micron Devices LLC, Miami Beach, FL (US)

(72) Inventors: Laura Tyler Perryman, Miami Beach, FL (US); Patrick Larson, Surfside, FL (US); Chad Andresen, Miami Beach, FL (US)

(73) Assignee: Stimwave Technologies Incorporated, Pompano Beach, FL (US)

( * ) Notice: Subject to any disclaimer, the term of this patent is extended or adjusted under 35 U.S.C. 154(b) by 0 days.

(21) Appl. No.: 14/445,159

(22) Filed: Jul. 29, 2014

(65) Prior Publication Data

US 2014/0336727 A1    Nov. 13, 2014

Related U.S. Application Data

(60) Division of application No. 13/584,618, filed on Aug. 13, 2012, now Pat. No. 8,849,412, which is a
(Continued)

(51) Int. Cl.
*A61N 1/372* (2006.01)
*A61N 1/02* (2006.01)
*A61N 1/36* (2006.01)

(52) U.S. Cl.
CPC ......... *A61N 1/37252* (2013.01); *A61N 1/025* (2013.01); *A61N 1/36125* (2013.01);
(Continued)

(58) Field of Classification Search
CPC ............ A61N 1/37252; A61N 1/37235; A61N 1/36146; A61N 1/37229; A61N 1/025;
(Continued)

(56) References Cited

U.S. PATENT DOCUMENTS 2,990,547 A   6/1961   McDougal
3,662,758 A   5/1972   Glover
(Continued)

FOREIGN PATENT DOCUMENTS

CN       1678370      10/2005
CN     101185789       5/2008
(Continued)

OTHER PUBLICATIONS

US 5,197,469 A, 03/1993, Adams (withdrawn)
(Continued)

*Primary Examiner* — Michael W Kahelin
(74) *Attorney, Agent, or Firm* — Fish & Richardson P.C.

(57) ABSTRACT

A system includes a controller module, which includes a storage device, a controller, a modulator, and one or more antennas. The storage device is stored with parameters defining a stimulation waveform. The controller is configured to generate, based on the stored parameters, an output signal that includes the stimulation waveform, wherein the output signal additionally includes polarity assignments for electrodes in an implantable, passive stimulation device. The modulator modulates a stimulus carrier signal with the output signal to generate a transmission signal. The one or more antennas transmit the transmission signal to the implantable, passive stimulation device such that the implantable, passive stimulation device uses energy in the transmission signal for operation, sets the polarities for the electrodes in the implantable, passive stimulation device based on the encoded polarity assignments, generates electrical pulses using the stimulation waveform, and applies the electrical pulses to excitable tissue.

9 Claims, 34 Drawing Sheets

Related U.S. Application Data continuation-in-part of application No. 13/562,221, filed on Jul. 30, 2012, now Pat. No. 9,199,089, which is a continuation-in-part of application No. PCT/US2012/023029, filed on Jan. 27, 2012.

(60) Provisional application No. 61/522,812, filed on Aug. 12, 2011, provisional application No. 61/513,397, filed on Jul. 29, 2011, provisional application No. 61/437,561, filed on Jan. 28, 2011.

(52) U.S. Cl.
CPC ..... *A61N 1/36146* (2013.01); *A61N 1/37223* (2013.01); *A61N 1/37229* (2013.01); *A61N 1/37235* (2013.01); *A61N 1/37247* (2013.01); *A61N 1/36139* (2013.01); *A61N 1/3727* (2013.01)

(58) Field of Classification Search
CPC ............ A61N 1/37247; A61N 1/36125; A61N 1/37223; A61N 1/36139; A61N 1/3727
See application file for complete search history.

(56) References Cited

U.S. PATENT DOCUMENTS

| | | | |
|---|---|---|---|
| 3,663,758 | A | 5/1972 | Erbert |
| 3,727,616 | A | 4/1973 | Lenzkes |
| 4,057,069 | A | 11/1977 | Dorffer |
| 4,102,344 | A | 7/1978 | Conway |
| 4,223,679 | A * | 9/1980 | Schulman .......... A61N 1/3727 607/32 |
| 4,494,950 | A | 1/1985 | Fischell |
| 4,524,774 | A | 6/1985 | Hildebrandt |
| 4,525,774 | A | 6/1985 | Kino |
| 4,532,930 | A * | 8/1985 | Crosby .............. A61N 1/36036 607/57 |
| 4,561,443 | A | 12/1985 | Hogrefe |
| 4,592,359 | A | 6/1986 | Galbraith |
| 4,612,934 | A | 9/1986 | Borkan |
| 4,628,933 | A | 12/1986 | Michelson |
| 4,736,752 | A | 4/1988 | Munck |
| 4,741,339 | A | 5/1988 | Harrison et al. |
| 4,750,499 | A | 6/1988 | Hoffer |
| 4,793,353 | A * | 12/1988 | Borkan ................ A61N 1/372 607/49 |
| 4,837,049 | A | 6/1989 | Byers et al. |
| 4,947,844 | A | 8/1990 | McDermott |
| 5,058,581 | A | 10/1991 | Silvian |
| 5,070,535 | A | 12/1991 | Hochmair et al. |
| 5,193,539 | A | 3/1993 | Schulman |
| 5,262,793 | A | 11/1993 | Sperry |
| 5,314,458 | A | 5/1994 | Najafi |
| 5,343,766 | A | 9/1994 | Lee |
| 5,358,514 | A | 10/1994 | Schulman |
| 5,411,535 | A | 5/1995 | Fujii |
| 5,583,510 | A | 12/1996 | Ponnapalli |
| 5,591,217 | A | 1/1997 | Barreras |
| 5,626,630 | A | 5/1997 | Markowitz |
| 5,735,887 | A | 4/1998 | Barreras |
| 5,769,877 | A | 6/1998 | Barreras |
| 5,861,019 | A | 1/1999 | Sun |
| 5,991,664 | A | 11/1999 | Seligman |
| 5,995,874 | A | 11/1999 | Borza |
| 6,141,588 | A | 10/2000 | Cox |
| 6,164,284 | A * | 12/2000 | Schulman ............ A61B 5/0031 128/899 |
| 6,175,752 | B1 | 1/2001 | Say |
| 6,350,335 | B1 | 2/2002 | Hampel |
| 6,364,889 | B1 | 4/2002 | Kheiri et al. |
| 6,415,184 | B1 | 7/2002 | Ishikawa |
| 6,445,953 | B1 | 9/2002 | Bulkes |
| 6,445,955 | B1 | 9/2002 | Michelson |
| 6,458,157 | B1 | 10/2002 | Suaning |
| 6,463,336 | B1 | 10/2002 | Mawhinney |
| D466,487 | S | 12/2002 | Wada et al. |
| 6,516,227 | B1 | 2/2003 | Meadows |
| D474,982 | S | 5/2003 | Wilson |
| 6,564,807 | B1 | 5/2003 | Schulman |
| 6,611,715 | B1 | 8/2003 | Boveja |
| 6,615,081 | B1 | 9/2003 | Boveja |
| 6,647,296 | B2 | 11/2003 | Fischell |
| 6,662,052 | B1 | 12/2003 | Sarwal |
| 6,684,104 | B2 | 1/2004 | Gordon et al. |
| 6,690,974 | B2 | 2/2004 | Archer |
| 6,889,086 | B2 | 5/2005 | Mass |
| 6,895,280 | B2 | 5/2005 | Meadows |
| 6,972,727 | B1 | 12/2005 | West et al. |
| 7,027,874 | B1 | 4/2006 | Sawan |
| 7,110,823 | B2 | 9/2006 | Whitehurst |
| D529,402 | S | 10/2006 | Burton |
| 7,177,690 | B2 | 2/2007 | Woods |
| 7,214,189 | B2 | 5/2007 | Zdeblick |
| 7,277,728 | B1 | 10/2007 | Kauhanen |
| 7,283,875 | B2 | 10/2007 | Larsson |
| 7,317,947 | B2 | 1/2008 | Wahlstrand |
| 7,436,752 | B2 | 10/2008 | He |
| 7,471,257 | B2 | 12/2008 | Candal |
| 7,489,248 | B2 | 2/2009 | Gengel et al. |
| 7,616,991 | B2 | 11/2009 | Mann et al. |
| 7,620,451 | B2 | 11/2009 | Demarais |
| 7,630,771 | B2 | 12/2009 | Cauller |
| 7,664,552 | B2 | 2/2010 | Wahlstrand |
| D612,543 | S | 3/2010 | Marseille |
| 7,738,964 | B2 | 6/2010 | Von |
| 7,741,734 | B2 | 6/2010 | Joannopoulos et al. |
| 7,765,013 | B2 | 7/2010 | Blick |
| 7,853,333 | B2 | 12/2010 | Demarais |
| 7,869,885 | B2 | 1/2011 | Begnaud |
| 7,894,905 | B2 | 2/2011 | Pless |
| 7,904,170 | B2 | 3/2011 | Harding |
| 7,908,014 | B2 | 3/2011 | Schulman et al. |
| 7,939,346 | B2 | 5/2011 | Blick |
| D658,302 | S | 4/2012 | Nixon |
| 8,170,672 | B2 | 5/2012 | Weiss |
| 8,242,968 | B2 | 8/2012 | Conrad et al. |
| 8,320,850 | B1 | 11/2012 | Khlat |
| 8,332,040 | B1 | 12/2012 | Winstrom |
| 8,634,928 | B1 | 1/2014 | O'Driscoll et al. |
| D701,504 | S | 3/2014 | Christopher et al. |
| D703,204 | S | 4/2014 | Riddiford et al. |
| D714,288 | S | 9/2014 | Aumiller et al. |
| 8,849,412 | B2 | 9/2014 | Perryman et al. |
| 8,903,502 | B2 | 12/2014 | Perryman |
| D721,701 | S | 1/2015 | Al-Nasser |
| D725,071 | S | 3/2015 | Lee et al. |
| D725,072 | S | 3/2015 | Kim et al. |
| D725,652 | S | 3/2015 | Ishii |
| D734,330 | S | 7/2015 | Huang et al. |
| 9,199,089 | B2 | 12/2015 | Perryman et al. |
| 9,220,897 | B2 | 12/2015 | Perryman et al. |
| 9,242,103 | B2 | 1/2016 | Perryman et al. |
| 9,254,393 | B2 | 2/2016 | Perryman et al. |
| 9,757,571 | B2 | 9/2017 | Perryman |
| 2001/0010662 | A1 | 8/2001 | Saitou et al. |
| 2002/0095195 | A1 | 7/2002 | Mass |
| 2002/0123779 | A1 | 9/2002 | Von Arx et al. |
| 2003/0078633 | A1 | 4/2003 | Firlik et al. |
| 2003/0114898 | A1 | 6/2003 | Von Arx et al. |
| 2003/0114899 | A1 | 6/2003 | Woods et al. |
| 2003/0139782 | A1 | 7/2003 | Duncan et al. |
| 2003/0169207 | A1 | 9/2003 | Beigel |
| 2003/0204224 | A1 | 10/2003 | Torgerson et al. |
| 2004/0044385 | A1 | 3/2004 | Fenn et al. |
| 2004/0059392 | A1 | 3/2004 | Parramon |
| 2004/0082979 | A1 | 4/2004 | Tong |
| 2004/0127942 | A1 | 7/2004 | Yomtov |
| 2004/0138723 | A1 | 7/2004 | Malick et al. |
| 2004/0167587 | A1 | 8/2004 | Thompson et al. |
| 2004/0176803 | A1 | 9/2004 | Whelan |
| 2004/0220621 | A1 | 11/2004 | Zhou |
| 2004/0230263 | A1 | 11/2004 | Samulski |
| 2005/0119716 | A1 | 6/2005 | McClure et al. |

(56) References Cited

U.S. PATENT DOCUMENTS

| | | |
|---|---|---|
| 2005/0137668 A1 | 6/2005 | Khan |
| 2005/0245994 A1 | 11/2005 | Varrichio et al. |
| 2006/0001583 A1 | 1/2006 | Bisig |
| 2006/0003721 A1 | 1/2006 | Bisig |
| 2006/0085039 A1 | 4/2006 | Hastings et al. |
| 2006/0085042 A1 | 4/2006 | Hastings |
| 2006/0161216 A1* | 7/2006 | John ................ A61N 1/3605 607/40 |
| 2006/0161225 A1 | 7/2006 | Sormann |
| 2006/0287686 A1 | 12/2006 | Cullen |
| 2006/0289528 A1 | 12/2006 | Chiu |
| 2007/0055322 A1 | 3/2007 | Forsberg et al. |
| 2007/0055324 A1 | 3/2007 | Thompson et al. |
| 2007/0100395 A1 | 5/2007 | Ibrahim |
| 2007/0100935 A1 | 5/2007 | Miyazaki |
| 2007/0106337 A1 | 5/2007 | Errico |
| 2007/0109208 A1 | 5/2007 | Turner |
| 2007/0112402 A1 | 5/2007 | Grill et al. |
| 2007/0156179 A1 | 7/2007 | S.E. |
| 2007/0208394 A1 | 9/2007 | King et al. |
| 2007/0213773 A1 | 9/2007 | Hill |
| 2007/0213783 A1 | 9/2007 | Pless |
| 2007/0254632 A1 | 11/2007 | Beadle |
| 2007/0265543 A1 | 11/2007 | VanSickle |
| 2007/0265690 A1 | 11/2007 | Lichtenstein |
| 2007/0288066 A1 | 12/2007 | Christman |
| 2008/0010358 A1 | 1/2008 | Jin |
| 2008/0046012 A1 | 2/2008 | Covalin |
| 2008/0077184 A1 | 3/2008 | Denker et al. |
| 2008/0077188 A1 | 3/2008 | Denker |
| 2008/0077189 A1* | 3/2008 | Ostroff ............... A61N 1/3706 607/27 |
| 2008/0103558 A1 | 5/2008 | Wenzel |
| 2008/0154217 A1 | 6/2008 | Carrez et al. |
| 2008/0266123 A1 | 10/2008 | Ales |
| 2008/0281244 A1 | 11/2008 | Jacobs |
| 2009/0018599 A1 | 1/2009 | Hastings et al. |
| 2009/0099405 A1 | 4/2009 | Schneider et al. |
| 2009/0105784 A1 | 4/2009 | Massoud-Ansari |
| 2009/0125091 A1 | 5/2009 | Schoenbach et al. |
| 2009/0132002 A1 | 5/2009 | Kieval |
| 2009/0132003 A1 | 5/2009 | Borgens |
| 2009/0200985 A1 | 8/2009 | Zane |
| 2009/0204170 A1 | 8/2009 | Hastings |
| 2009/0234407 A1 | 9/2009 | Hastings |
| 2009/0248112 A1 | 10/2009 | Mumbru |
| 2009/0292339 A1 | 11/2009 | Erickson |
| 2010/0053789 A1 | 3/2010 | Duric |
| 2010/0114198 A1 | 5/2010 | Donofrio |
| 2010/0125269 A1 | 5/2010 | Emmons |
| 2010/0137938 A1 | 6/2010 | Kishawi et al. |
| 2010/0168818 A1 | 7/2010 | Barror |
| 2010/0174340 A1 | 7/2010 | Simon |
| 2010/0179449 A1 | 7/2010 | Chow |
| 2010/0198039 A1 | 8/2010 | Towe |
| 2010/0198307 A1 | 8/2010 | Toy et al. |
| 2010/0231382 A1 | 9/2010 | Tayrani |
| 2010/0234922 A1 | 9/2010 | Forsell |
| 2010/0241051 A1 | 9/2010 | Dacey, Jr. et al. |
| 2010/0268298 A1 | 10/2010 | Moffitt |
| 2010/0269339 A1 | 10/2010 | Dye et al. |
| 2010/0298742 A1 | 11/2010 | Perlman |
| 2010/0331934 A1 | 12/2010 | McDonald |
| 2011/0040350 A1 | 2/2011 | Griffith |
| 2011/0074342 A1 | 3/2011 | MacLaughlin |
| 2011/0077698 A1 | 3/2011 | Tsampazis et al. |
| 2011/0098583 A1 | 4/2011 | Pandia |
| 2011/0106220 A1 | 5/2011 | DeGiorgio et al. |
| 2011/0120822 A1 | 5/2011 | Kondou |
| 2011/0121822 A1 | 5/2011 | Parsche |
| 2011/0125214 A1 | 5/2011 | Goetz |
| 2011/0130804 A1 | 6/2011 | Lin |
| 2011/0144468 A1 | 6/2011 | Boggs et al. |
| 2011/0152750 A1 | 6/2011 | Dacey et al. |
| 2011/0172733 A1 | 7/2011 | Lima et al. |
| 2011/0190849 A1 | 8/2011 | Faltys |
| 2011/0245892 A1 | 10/2011 | Kast et al. |
| 2012/0004709 A1 | 1/2012 | Chen et al. |
| 2012/0158407 A1 | 6/2012 | Forsell |
| 2012/0194399 A1 | 8/2012 | Bily et al. |
| 2012/0215218 A1 | 8/2012 | Lipani |
| 2012/0283800 A1 | 11/2012 | Perryman et al. |
| 2012/0330384 A1 | 12/2012 | Perryman et al. |
| 2013/0016016 A1 | 1/2013 | Lin et al. |
| 2013/0018439 A1 | 1/2013 | Chow et al. |
| 2013/0066400 A1 | 3/2013 | Perryman |
| 2013/0079849 A1 | 3/2013 | Perryman et al. |
| 2013/0165991 A1 | 6/2013 | Kim |
| 2013/0310901 A1 | 11/2013 | Perryman et al. |
| 2014/0031837 A1 | 1/2014 | Perryman et al. |
| 2014/0047713 A1 | 2/2014 | Singh et al. |
| 2014/0058480 A1 | 2/2014 | Perryman et al. |
| 2014/0058481 A1 | 2/2014 | Perryman et al. |
| 2014/0169142 A1 | 6/2014 | Heck et al. |
| 2014/0266935 A1 | 9/2014 | Tankiewicz |
| 2014/0336727 A1 | 11/2014 | Perryman et al. |
| 2015/0321017 A1 | 11/2015 | Perryman et al. |
| 2016/0101287 A1 | 4/2016 | Perryman |
| 2018/0236248 A1 | 8/2018 | Perryman |
| 2018/0264277 A1 | 9/2018 | Perryman |

FOREIGN PATENT DOCUMENTS

| | | |
|---|---|---|
| CN | 101352596 | 1/2009 |
| CN | 101773701 | 7/2010 |
| CN | 201676401 | 12/2010 |
| EP | 2462981 | 6/2001 |
| EP | 1588609 A2 | 10/2005 |
| JP | 2002524124 | 8/2002 |
| JP | 2008161667 | 7/2008 |
| JP | 2008528222 | 7/2008 |
| JP | 2009523402 | 6/2009 |
| JP | 201155912 | 3/2011 |
| JP | 2011510787 | 4/2011 |
| WO | WO 2000013585 | 3/2000 |
| WO | WO 2004004826 | 1/2004 |
| WO | WO 2006113802 | 10/2006 |
| WO | WO 2007059386 | 5/2007 |
| WO | WO 2007081971 | 7/2007 |
| WO | WO 2010051189 | 5/2010 |
| WO | WO 2010053789 | 5/2010 |
| WO | WO 2010057046 | 5/2010 |
| WO | WO 2010104569 | 9/2010 |
| WO | WO2011079309 A2 | 6/2011 |
| WO | WO 2012103519 | 8/2012 |
| WO | WO 2012138782 | 10/2012 |
| WO | WO 2013019757 | 2/2013 |
| WO | WO 2013025632 | 2/2013 |
| WO | WO 2013040549 | 3/2013 |

OTHER PUBLICATIONS

PCT Notification of Transmittal of the International Search Report and the Written Opinion for Application No. PCTUS2012048903 dated Oct. 10, 2012, 10 pages.

PCT Notification of the International Search Report and Written Opinion of Application No. PCTUS 1250633 dated Oct. 23, 2012, 8 pages.

Notification of Transmittal of the International Search Report and the Written Opinion of the International Searching Authority, or the Declaration dated May 16, 2012 in International Application No. PCTUS1223029, 11 pages.

U.S. Non-Final Office Action for U.S. Appl. No. 13/584,618 dated Jun. 12, 2013, 15 pages.

PCT International Search Report and PCT Written Opinion of the International Searching Authority for application PCT/US2012/55746, dated Jan. 3, 2013, 11 pages.

PCT International Search Report, application PCT/US2012/032200, dated Jul. 27, 2012, 13 pages.

Communication from the European Patent Office in EP Application No. 12767575.9, dated Nov. 7, 2014, 7 pages.

(56) References Cited

OTHER PUBLICATIONS

International Preliminary Report on Patentability and Written Opinion for PCT/US2012/032200 dated Oct. 8, 2013, 11 pages.
International Preliminary Report on Patentability and Written Opinion for PCT/US2012/023029, dated Jan. 28, 2014, 9 pages.
International Preliminary Report on Patentability and Written Opinion for PCT/US2012/048903, dated Mar. 25, 2014, 8 pages.
International Preliminary Report on Patentability issued in International Application No. PCT/US2012/055746, dated Mar. 18, 2014, 10 pages.
U.S. Non-Final Office Action for U.S. Appl. No. 13/621,530, dated Apr. 11, 2014, 15 pages.
U.S. Notice of Allowance for U.S. Appl. No. 13/897,427, dated Jul. 28, 2014, 8 pages.
U.S. Final Office Action for U.S. Appl. No. 13/562,221, dated Oct. 23, 2014, 22 pages.
U.S. Final Office Action for U.S. Appl. No. 13/621,530, dated Jan. 5, 2015, 32 pages.
U.S. Non-Final Office Action for U.S. Appl. No. 14/045,764 dated Apr. 1, 2015, 15 pages.
Partial Supplementary European Search Report from European Patent Application No. 12831083.6, dated Mar. 24, 2015, 7 pages.
Extended European Search report in Application No. 12831083.6, dated Aug. 17, 2015, 9 pages.
Extended European Search report in Application No. 12740011.7, dated Sep. 9, 2015, 6 pages.
Extended European Search report in Application No. 12819482.6, dated Apr. 28, 2015, 7 pages.
Extended European Search Report in Application No. 12824347.4, dated Apr. 22, 2015, 6 pages.
U.S. Advisory Action for U.S. Appl. No. 13/551,050, dated Apr. 24, 2015, 3 pages.
U.S. Final Office Action for U.S. Appl. No. 13/551,050, dated Feb. 13, 2015, 18 pages.
U.S. Final Office Action for U.S. Appl. No. 14/068,750 dated Jul. 29, 2015, 18 pages.
U.S. Non-Final Office Action for U.S. Appl. No. 14/045,764 dated Feb. 6, 2015, 14 pages.
U.S. Non-Final Office Action for U.S. Appl. No. 13/551,050 dated Sep. 24, 2015, 16 pages.
U.S. Notice of Allowance for U.S. Appl. No. 13/562,221, dated Jul. 21, 2015, 8 pages.
U.S. Notice of Allowance for U.S. Appl. No. 13/621,530, dated Aug. 20, 2015, 9 pages.
U.S. Notice of Allowance for U.S. Appl. No. 14/045,764, dated Aug. 17, 2015, 11 pages.
Extended European Search Report in Application No. 15793285.6, dated Dec. 12, 2017, 7 pages.
U.S. Appl. No. 14/445,159, filed Nov. 13, 2014, Perryman et al.
U.S. Appl. No. 29/478,687, filed Jan. 7, 2003, Perryman et al.
"Assembly, Wearable Antenna, 350-450 MHz," Retrieved from the Internet: <URL: http://www.pharad.com/pdf/UHF-Wearable-Antenna-2D.pdf>, Oct. 14, 2010, 1 page.
"Pharad at Forefront of LTE Antenna Innovation with Develpoment of LTE Wearable Antenna," Wireless Design Mag [online] Aug. 12, 2012. Retrieved from the Internet: <URL:http://www.wirelessdesignmag.com/product-release/2013/08/pharad-forefront-lte-antenna-innovation-development-lte-wearable-antenna>, 3 pages.
Associate letter reporting Office Action in Application No. MX/a/2013/008690, dated Feb. 12, 2016, 1 page.
Chinese Office Action in Application No. 201280006578.7, dated Dec. 8, 2014.
Chinese Office Action in Application No. 201280006578.7, dated Jul. 29, 2015, 14 pages (with English translation).
Chinese Office action in Application No. 201280006578.7, dated Mar. 2, 2016, 9 pages.
Chinese Office Action in Application No. 201280017245.4, dated Mar. 2, 2016, 10 pages (with English translation).
Chinese Office Action in Application No. 201280017245.4, dated Aug. 3, 2015, 16 pages (with English translation).
Chinese Office Action in Application No. 201280017245.4, dated Dec. 3, 2014, 6 pages (with English translation).
Chinese Office Action in Application No. 201280037814, dated May 6, 2015, 18 pages (with English translation).
Chinese Office Action in Application No. 201280037814.1 dated Mar. 7, 2016, 31 pages (with English translation.
European Search Report in European Application No. 12767575.9, dated Jan. 11, 2018, 6 pages.
Examination Report in Application No. 2012240239, dated May 9, 2016, 3 pages.
Examination Report in Application No. 2012308197, dated Apr. 22, 2016, 5 pages.
Extended European Search report in Application No. 12767575.9, dated Nov. 10, 2014, 7 pages.
Iannetta, "Nov. 2014 New Products: Wearable coil facilities positioning during prostate MRI" Urology Times [online] Nov. 10, 2014 [retreived 2016-03017]. Retrieved from the Internet: <URL: http://urologytimes.modernmedicine.com/urology-times/news/november-2014-new-products-wearable-coil-facilitates-positioning-during-prostate-mri?page=full>, 7 pages.
International Preliminary Report on Patentability for PCT/US2013/077846, dated Jun. 30, 2015, 6 pages.
International Preliminary Report on Patentability issued in International Application No. PCT/US2012/050633, dated Feb. 18, 2014, 7 pages.
International Search Report and Written Opinion for International Application No. PCT/US2013/077846 dated Apr. 21, 2014, 10 pages.
International Search Report and Written Opinion for PCT/US2012/032200, dated Jul. 27, 2014, 13 pages.
International Search Report and Written Opinion in International Application No. PCT/US2015/030433, dated Sep. 29, 2015, 18 pages.
Isreal Office Action in Isreal Application No. 228485, dated Jan. 16, 2017, 16 pages.
Japanese Office Action in Japanese Application No. 2014-503961, dated Nov. 8, 2017.
Japanese Office Action in Japanese Application No. 2014-503961, dated Mar. 30, 2016, 10 pages.
Notice of Allowance for U.S. Appl. No. 14/141,197, dated Sep. 30, 2015, 7 pages.
O'Driscoll et al., "A mm-Sized implantable power receiver with adaptive link compensation," ISSCC 2009, Session 17, TD: Energy-Aware Sensor Systems, 17.5, 2009, 3 pages.
Office Action in JP Application No. 2013-551396, dated Jan. 12, 2016, 7 pages (with English translations).
Poon et al., "Optimal frequency for wireless power transmission into dispersive tissue," IEEE Transactions on Antennas and Propagation, May 2010, 58(5):1739-1750.
U.S Non-Final Office Action for U.S. Appl. No. 13/584,618, dated May 23, 2013, 6 pages.
U.S Notice of Allowance for U.S. Appl. No. 14/068,750, dated Jun. 13, 2016, 5 pages.
U.S. Advisory Action for U.S. Appl. No. 13/621,530, dated May 11, 2015, 3 pages.
U.S. Final Office Action for U.S. Appl. No. 13/584,618, dated Aug. 26, 2013, 13 pages.
U.S. Final Office Action for U.S. Appl. No. 14/141,197, dated Jul. 8, 2015, 11 pages.
U.S. Final Office Action for U.S. Appl. No. 14/445,159, dated Jun. 9, 2016, 9 pages.
U.S. Final Office Action in U.S. Appl. No. 14/445,159, dated Dec. 15, 2015, 7 pages.
U.S. Non-Final Office Action for U.S. Appl. No. 13/551,050 dated Mar. 4, 2014, 30 pages.
U.S. Non-Final Office Action for U.S. Appl. No. 13/562,221, dated Jan. 29, 2014, 30 pages.
U.S. Non-final Office Action for U.S. Appl. No. 13/897,427, dated Jan. 9, 2014, 24 pages.
U.S. Non-Final Office Action for U.S. Appl. No. 14/068,750 dated Jan. 9, 2015, 27 pages.
U.S. Non-Final Office Action for U.S. Appl. No. 14/141,197, dated Mar. 4, 2015, 11 pages.

(56) References Cited

OTHER PUBLICATIONS

U.S. Non-Final Office Action for U.S. Appl. No. 14/710,548, dated Dec. 18, 2015, 6 pages.
U.S. Non-Final Office Action for U.S. Appl. No. 29/478,687, dated Aug. 12, 2015, 8 pages.
U.S. Non-final Office Action in U.S. Appl. No. 14/068,750, dated Jan. 4, 2016, 13 pages.
U.S. Notice of Allowance for U.S. Appl. No. 13/551,050 dated Apr. 6, 2016, 7 pages.
U.S. Notice of Allowance for U.S. Appl. No. 13/584,618, dated May 16, 2014, 8 pages.
U.S. Notice of Allowance for U.S. Appl. No. 13/621,530, dated Oct. 7, 2015, 4 pages.
U.S. Notice of Allowance for U.S. Appl. No. 13/897,427, dated Sep. 24, 2014, 4 pages.
U.S. Notice of Allowance for U.S. Appl. No. 14/710,548, dated Apr. 4, 2016, 6 pages.
U.S. Office Action for U.S. Appl. No. 13/551,050 dated Sep. 12, 2013, 8 pages.
U.S. Office Action for U.S. Appl. No. 13/562,221, dated Sep. 13, 2013, 7 pages.
US. Advisory Action for U.S. Appl. No. 13/584,618, dated Nov. 1, 2013, 3 pages.
EP Office Action in European ApplN No. 15793285.6, dated Oct. 4, 2018, 6 pages.
CN Office Action in Chinese ApplN No. 201580036252.2, dated Sep. 30, 2018, 87 pages.
EP Office Action in European ApplN No. 12740011.7, dated Sep. 18, 2018, 21 pages.
EP European Search Report in European ApplN No. 17208566.4, dated Sep. 26, 2018, 14 pages.

\* cited by examiner

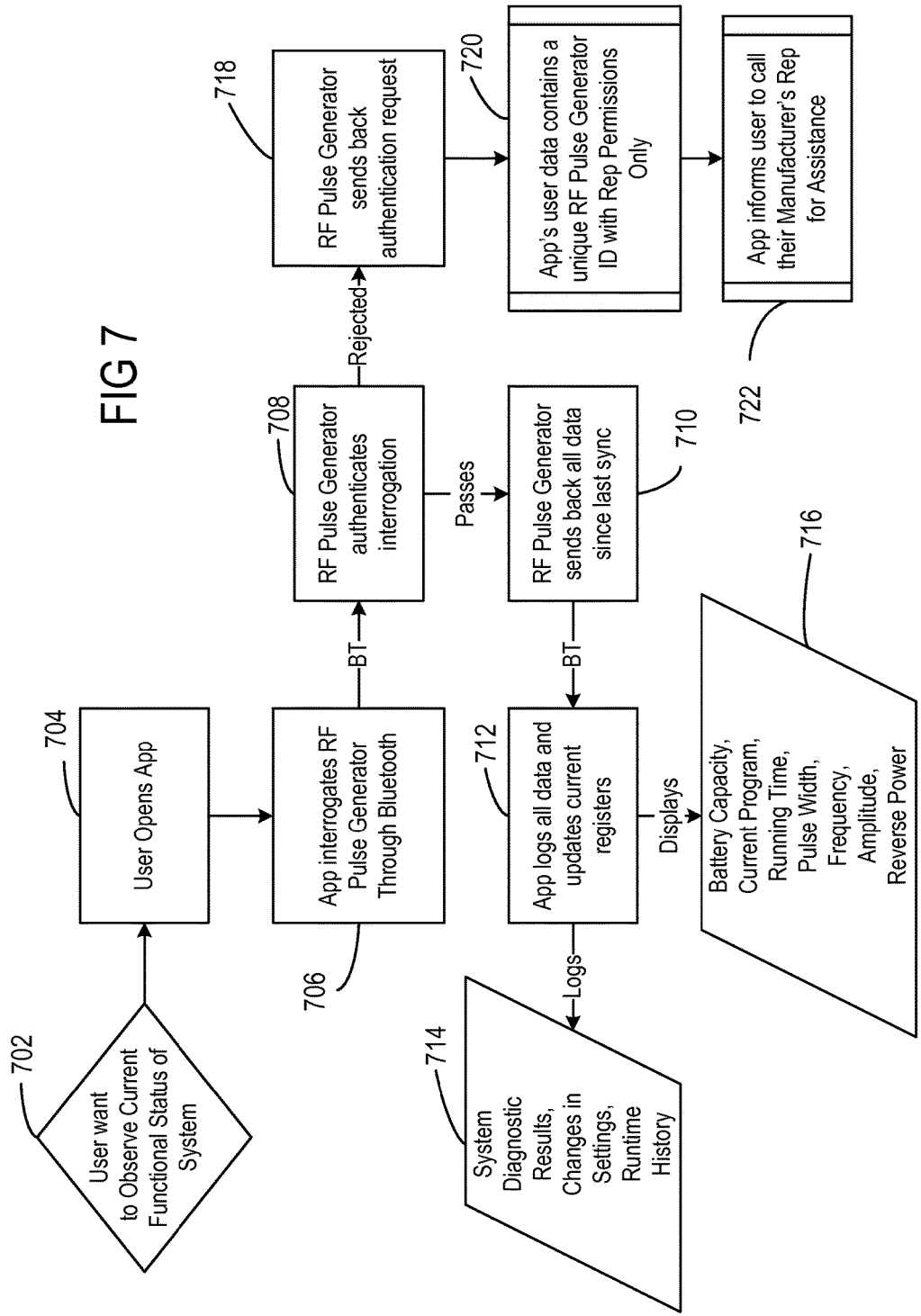

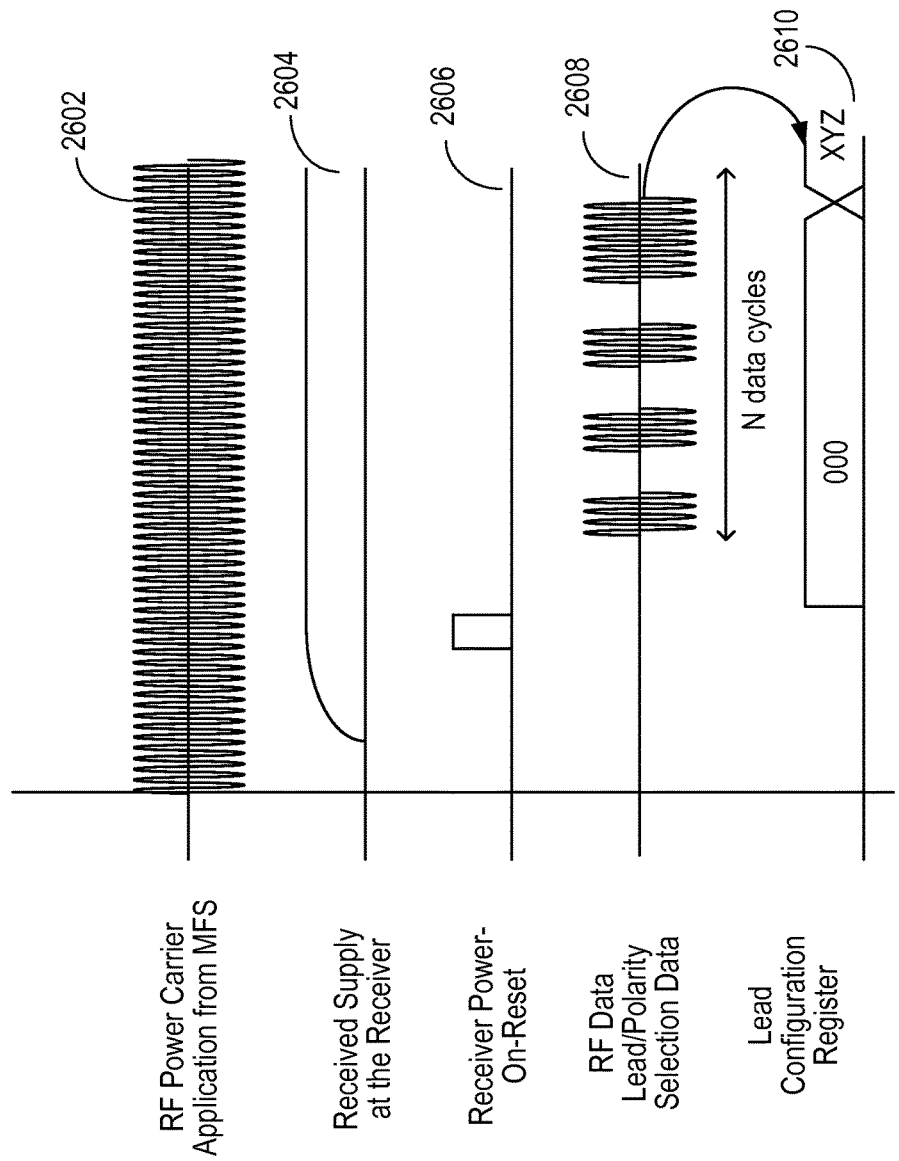

MICROWAVE FIELD STIMULATOR

CROSS REFERENCE TO RELATED APPLICATIONS

This application is a divisional (and claims the benefit of priority under 35 USC 121) of U.S. application Ser. No. 13/584,618, filed Aug. 13, 2012, now allowed, which claims the benefit of U.S. Provisional Application Ser. No. 61/522,812, filed Aug. 12, 2011. This application is a continuation-in-part of U.S. application Ser. No. 13/562,221, filed Jul. 30, 2012, which claims benefit of U.S. Provisional Application Ser. No. 61/513,397, filed Jul. 29, 2011, and is a continuation-in-part of PCT Application PCT/US2012/023029, filed Jan. 27, 2012, which claims benefit of U.S. Provisional Application Ser. No. 61/437,561, filed Jan. 28, 2011. All of the proceeding applications are hereby incorporated by reference in their entirety.

BACKGROUND

Neural modulation of neural tissue in the body by electrical stimulation has become an important type of therapy for chronic disabling conditions, such as chronic pain, problems of movement initiation and control, involuntary movements, dystonia, urinary and fecal incontinence, sexual difficulties, vascular insufficiency, heart arrhythmia and more. Electrical stimulation of the spinal column and nerve bundles leaving the spinal cord was the first approved neural modulation therapy and been used commercially since the 1970s. Implanted electrodes are used to pass pulsatile electrical currents of controllable frequency, pulse width and amplitudes. Two or more electrodes are in contact with neural elements, chiefly axons, and can selectively activate varying diameters of axons, with positive therapeutic benefits. A variety of therapeutic intra-body electrical stimulation techniques are utilized to treat neuropathic conditions that utilize an implanted neural stimulator in the spinal column or surrounding areas, including the dorsal horn, dorsal root ganglia, dorsal roots, dorsal column fibers and peripheral nerve bundles leaving the dorsal column or brain, such as vagus-, occipital-, trigeminal, hypoglossal-, sacral-, and coccygeal nerves.

SUMMARY

In one aspect, a system includes a controller module. The controller module includes a storage device, a controller, a modulator, and one or more antennas. The storage device is configured to store parameters defining a stimulation waveform. The controller is configured to generate, based on the stored parameters, an output signal that includes the stimulation waveform. The output signal additionally includes polarity assignments for electrodes in an implantable passive neural stimulation device. The modulator configured to modulate a carrier signal with the output signal to generate a transmission signal. The one or more antennas configured to transmit the transmission signal to the implantable, passive stimulation device such that the implantable, passive stimulation device uses energy in the transmission signal for operation, sets the polarities for the electrodes in the implantable, passive stimulation device based on the encoded polarity assignments, generates electrical pulses using the stimulation waveform, and applies the electrical pulses to excitable tissue.

Implementations of this and other aspects may include the following features. The stimulation waveform may include a sequence of pulses and the stored parameters include at least one of: a pulse duration, pulse amplitude, and a pulse repetition rate. The output signal generated by the controller may include a configuration portion that encodes the polarity assignments and a stimulation portion that includes the stimulation waveform.

The controller module may be configured to generate the transmission signal such that the transmission signal has an initial power-on portion that precedes the configuration portion and the stimulation portion, the initial portion being sent to the implantable, passive stimulation device as part of the transmission signal such that the implantable, passive stimulation device stores energy from the initial power-on portion and sends a power-on event signal when the stored energy reaches a threshold amount.

The controller module may be further configured to: receive the power-on event signal from the implantable passive stimulator; in response to receiving the power-on event signal, generate the configuration portion that is sent to the implantable passive stimulation device; and after generating the configuration portion, generate the stimulation portion. The configuration portion may include multiple waveform edges that encode the polarity assignments.

The controller module may further include a rechargeable power source managed by a power management protocol. The power management protocol may include: a level in which the receiver is configured to ignore telemetry feedback signal from the implantable passive stimulation device. The rechargeable power source may include one of: a lithium-ion battery, a lithium polymer battery.

The system may further include a programmer module having a visual programming interface to enable a user to program the controller module. The visual programming module may be configured to authenticate the user and thereafter provide access control to the user.

In some implementations of the system, the one or more antennas may be further configured to receive telemetry feedback signals from the implantable passive device in response to the transmission signal, and the controller may be further configured to modify the output signal by using a closed-loop feedback control based on the received telemetry feedback signal.

In one implementation, the controller may be further programmed to apply the closed-loop feedback control by: ascertaining a distortion to the electrical pulses as applied by the electrodes of the implantable, passive stimulation device, the distortion caused by at least one of a transmission characteristic of the antenna, a characteristic of the implantable passive stimulation device, or an impedance characteristic of the tissue; and adjusting the stimulation waveform embedded in the transmission signal to compensate the distortion such that the electrical pulses as applied are substantially undistorted despite the transmission characteristic of the antenna, the characteristic of the implantable passive stimulation device, or the impedance characteristic of the tissue. The distortion may be characterized as a frequency response corresponding to at least one of the transmission characteristic of the antenna, the characteristic of the implantable passive stimulation device, and the impedance characteristic of the tissue. The adjustment may be by filtering the transmission signal according to an inverse of the frequency response.

In another implementation, the controller may be further programmed to apply the closed-loop feedback control by: monitoring a stimulus power being directed to the tissue through the electrodes based on information contained in the telemetry feedback signal; and adjusting a parameter associated with the stimulation waveform embedded in the transmission signal such that the stimulus power remains substantially constant. Changes in the stimulus power are induced by patient body movement. The parameter may include an amplitude level associated with the stimulation waveform, and the amplitude level may be adjusted based on a lookup table showing a relationship between the amplitude level and a corresponding power applied to the tissue through the electrodes. The adjustments may include modifying the carrier frequency within a range of up to 10 megahertz.

The storage device may include non-volatile memory including at least one of: an EEPROM, a flash memory.

The controller module is placed within a 3-feet radius of the implantable, passive stimulation device. The controller module may be placed as a sub-cutaneous implantation. In another aspect, a system includes a controller module. The controller module includes a storage device, a controller, a modulator, and one or more antennas. The storage device is configured to store parameters defining a stimulation waveform and polarity assignments for electrodes in an implantable, passive stimulation device that includes a power-on reset circuit, control logic, stimulation circuitry, and stimulation electrodes. The controller is configured to generate, based on the stored parameters and polarity assignments, an output signal that includes an initial power-on portion followed by a configuration portion that encodes the polarity assignments followed by a stimulation portion that includes the stimulation waveform. The modulator is configured to modulate a carrier signal with the output signal to generate a transmission signal. The one or more antennas are configured to transmit the transmission signal to the implantable passive stimulation device such that the power-on reset circuit uses energy in the power-on portion to generate a power-on reset signal that resets the control logic, the control logic reads the polarity assignment information encoded in the configuration portion and sets the polarities for the electrodes, and the stimulation circuitry generates electrical pulses using the stimulation waveform and applies the electrical pulses to excitable tissue.

Implementations of this and other aspects may include the following features. The controller module may be configured to read a telemetry feedback signal from the implantable passive stimulation device, the telemetry signal generated by: sensing a first electrical parameter and a second electrical parameter concurrently; and comparing the first electrical parameter and the second electrical parameter to generate an analog carrier frequency signal with a stimulus carrier frequency that is proportional to a difference between the first electrical parameter and the second electrical parameter.

The first electrical parameter may be a voltage over a reference resistor placed in serial connection with the electrode, and the second electrical parameter may be a voltage over the electrode. The stimulus carrier frequency may be proportional to a difference between a voltage over the reference resistor and a voltage over the electrode.

The first electrical parameter may be a voltage over a reference resistor placed in serial connection with the electrode, and the second electrical parameter may be a voltage over a calibration resister placed in parallel connection with the electrode. The stimulus carrier frequency may be proportional to a difference between a voltage over the reference resistor and the voltage over the calibration resistor.

The first electrical parameter may correspond to a fixed voltage and the second electrical parameter may be a voltage over one of: a calibration resistor, a reference resistor, an electrode.

The power-on signal may cause a handshake signal to be transmitted from implantable, passive stimulator to the controller module, the handshake signal confirms to the controller module that the implantable, passive stimulation device is ready to receive polarity setting information.

The handshake signal may be received from the implantable, passive stimulator when the polarities for the electrodes are set according to the polarity assignment information encoded in the configuration portion, the handshake signal confirms to the controller module that the implantable, passive stimulator is ready to receive the stimulation portion of the transmission signal.

The details of one or more implementations are set forth in the accompanying drawings and the description below. Other features, objects, and advantages will be apparent from the description and drawings, and from the claims.

DESCRIPTION OF DRAWINGS

FIG. 7 is a flow chart showing a process for the user to control the implantable wireless neural stimulator through an external programmer in an open loop feedback system.

FIG. 26 is a timing diagram showing example waveforms during the initial portion and the subsequent configuration portion of a transmission signal received at the implantable, passive stimulation device.

DETAILED DESCRIPTION

In various implementations, a neural stimulation system may be used to send electrical stimulation to targeted nerve tissue by using remote radio frequency (RF) energy with neither cables nor inductive coupling to power the passive implanted stimulator. The targeted nerve tissues may be, for example, in the spinal column including the spinothalamic tracts, dorsal horn, dorsal root ganglia, dorsal roots, dorsal column fibers, and peripheral nerves bundles leaving the dorsal column or brainstem, as well as any cranial nerves, abdominal, thoracic, or trigeminal ganglia nerves, nerve bundles of the cerebral cortex, deep brain and any sensory or motor nerves.

For instance, in some implementations, the neural stimulation system may include a controller module, such as an RF pulse generator module, and a passive implanted neural stimulator that contains one or more dipole antennas, one or more circuits, and one or more electrodes in contact with or in proximity to targeted neural tissue to facilitate stimulation. The RF pulse generator module may include an antenna and may be configured to transfer energy from the module antenna to the implanted antennas. The one or more circuits of the implanted neural stimulator may be configured to generate electrical pulses suitable for neural stimulation using the transferred energy and to supply the electrical pulses to the electrodes so that the pulses are applied to the neural tissue. For instance, the one or more circuits may include wave conditioning circuitry that rectifies the received RF signal (for example, using a diode rectifier), transforms the RF energy to a low frequency signal suitable for the stimulation of neural tissue, and presents the resulting waveform to an electrode array. The one or more circuits of the implanted neural stimulator may also include circuitry for communicating information back to the RF pulse generator module to facilitate a feedback control mechanism for stimulation parameter control. For example, the implanted neural stimulator may send to the RF pulse generator module a stimulus feedback signal that is indicative of parameters of the electrical pulses, and the RF pulse generator module may employ the stimulus feedback signal to adjust parameters of the signal sent to the neural stimulator.

Figure 1:
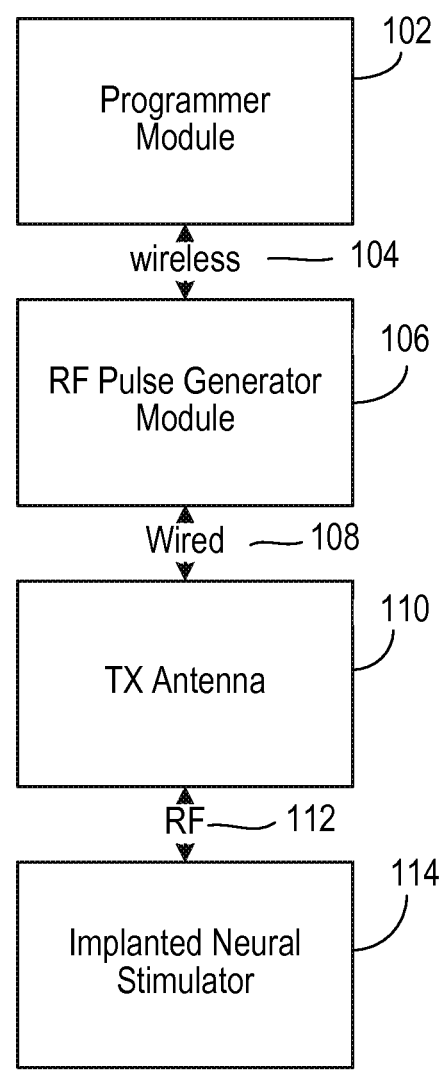
FIG. 1 depicts a high-level diagram of an example of a wireless neural stimulation system.

FIG. 1 depicts a high-level diagram of an example of a neural stimulation system. The neural stimulation system may include four major components, namely, a programmer module 102, a RF pulse generator module 106, a transmit (TX) antenna 110 (for example, a patch antenna, slot antenna, or a dipole antenna), and an implanted wireless neural stimulator 114. The programmer module 102 may be a computer device, such as a smart phone, running a software application that supports a wireless connection 114, such as Bluetooth®. The application can enable the user to view the system status and diagnostics, change various parameters, increase/decrease the desired stimulus amplitude of the electrode pulses, and adjust feedback sensitivity of the RF pulse generator module 106, among other functions.

The RF pulse generator module 106 may include communication electronics that support the wireless connection 104, the stimulation circuitry, and the battery to power the generator electronics. In some implementations, the RF pulse generator module 106 includes the TX antenna embedded into its packaging form factor while, in other implementations, the TX antenna is connected to the RF pulse generator module 106 through a wired connection 108 or a wireless connection (not shown). The TX antenna 110 may be coupled directly to tissue to create an electric field that powers the implanted neural stimulator module 114. The TX antenna 110 communicates with the implanted neural stimulator module 114 through an RF interface. For instance, the TX antenna 110 radiates an RF transmission signal that is modulated and encoded by the RF pulse generator module 110. The implanted wireless neural stimulator module 114 contains one or more antennas, such as dipole antenna(s), to receive and transmit through RF interface 112. In particular, the coupling mechanism between antenna 110 and the one or more antennas on the implanted neural stimulation module 114 is electrical radiative coupling and not inductive coupling. In other words, the coupling is through an electric field rather than a magnetic field.

Through this electrical radiative coupling, the TX antenna 110 can provide an input signal to the implanted neural stimulation module 114. This input signal contains energy and may contain information encoding stimulus waveforms to be applied at the electrodes of the implanted neural stimulator module 114. In some implementations, the power level of this input signal directly determines an applied amplitude (for example, power, current, or voltage) of the one or more electrical pulses created using the electrical energy contained in the input signal. Within the implanted wireless neural stimulator 114 are components for demodulating the RF transmission signal, and electrodes to deliver the stimulation to surrounding neuronal tissue.

The RF pulse generator module 106 can be implanted subcutaneously, or it can be worn external to the body. When external to the body, the RF generator module 106 can be incorporated into a belt or harness design to allow for electric radiative coupling through the skin and underlying tissue to transfer power and/or control parameters to the implanted neural stimulator module 114, which can be a passive stimulator. In either event, receiver circuit(s) internal to the neural stimulator module 114 can capture the energy radiated by the TX antenna 110 and convert this energy to an electrical waveform. The receiver circuit(s) may further modify the waveform to create an electrical pulse suitable for the stimulation of neural tissue, and this pulse may be delivered to the tissue via electrode pads.

In some implementations, the RF pulse generator module 106 can remotely control the stimulus parameters (that is, the parameters of the electrical pulses applied to the neural tissue) and monitor feedback from the wireless neural stimulator module 114 based on RF signals received from the implanted wireless neural stimulator module 114. A feedback detection algorithm implemented by the RF pulse generator module 106 can monitor data sent wirelessly from the implanted wireless neural stimulator module 114, including information about the energy that the implanted wireless neural stimulator module 114 is receiving from the RF pulse generator and information about the stimulus waveform being delivered to the electrode pads. In order to provide an effective therapy for a given medical condition, the system can be tuned to provide the optimal amount of excitation or inhibition to the nerve fibers by electrical stimulation. A closed loop feedback control method can be used in which the output signals from the implanted wireless neural stimulator module 114 are monitored and used to determine the appropriate level of neural stimulation current for maintaining effective neuronal activation, or, in some cases, the patient can manually adjust the output signals in an open loop control method.

Figure 2A:
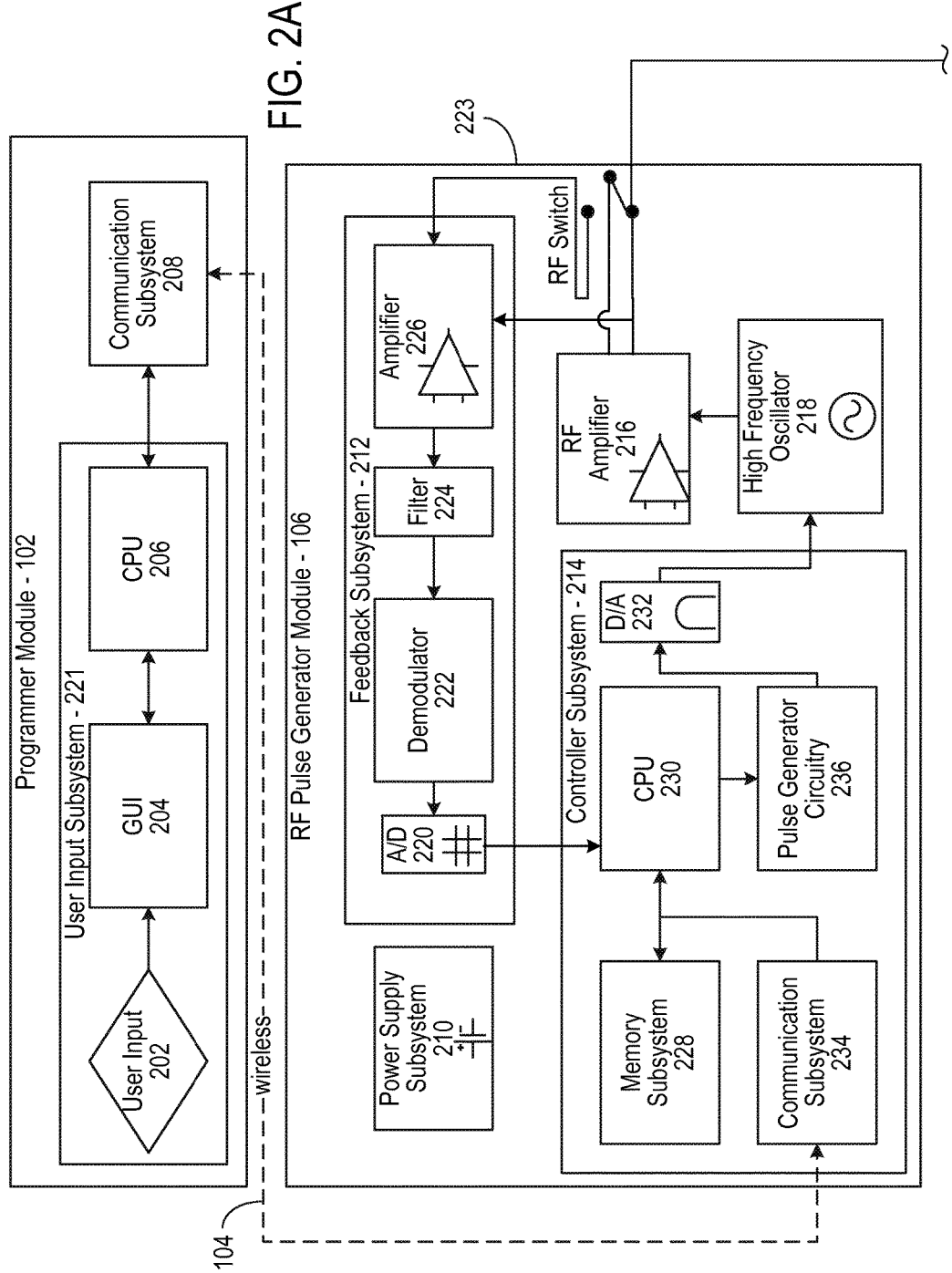
FIGS. 2A and 2B depict a detailed diagram of an example of the wireless neural stimulation system.
Figure 2B:
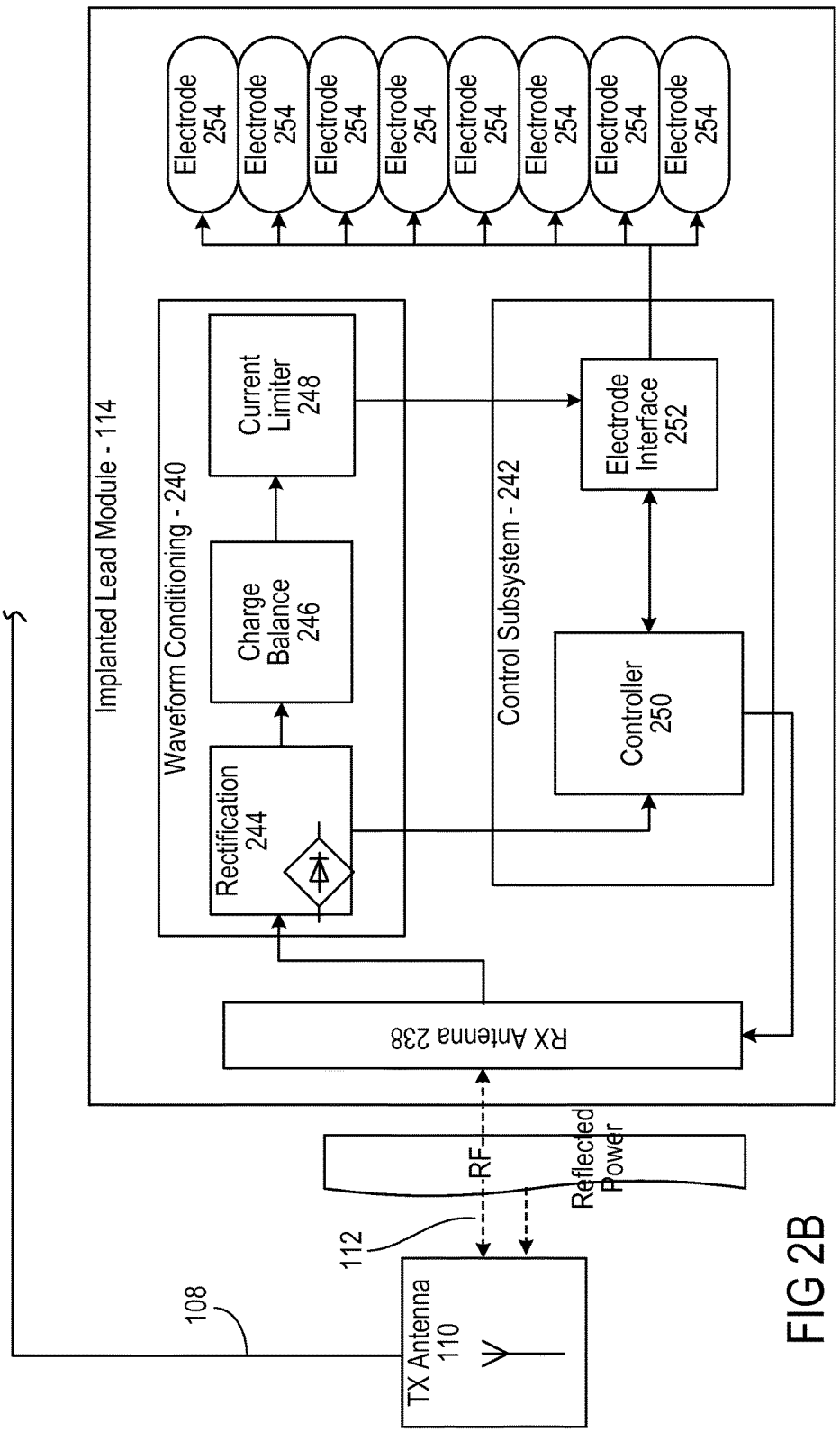

FIGS. 2A and 2B depict a detailed diagram of an example of the neural stimulation system. As depicted, the programming module 102 may comprise user input system 202 and communication subsystem 208. The user input system 221 may allow various parameter settings to be adjusted (in some cases, in an open loop fashion) by the user in the form of instruction sets. The communication subsystem 208 may transmit these instruction sets (and other information) via the wireless connection 104, such as Bluetooth or Wi-Fi, to the RF pulse generator module 106, as well as receive data from module 106.

For instance, the programmer module 102, which can be utilized for multiple users, such as a patient's control unit or clinician's programmer unit, can be used to send stimulation parameters to the RF pulse generator module 106. The stimulation parameters that can be controlled may include pulse amplitude, pulse frequency, and pulse width in the ranges shown in Table 1. In this context the term pulse refers to the phase of the waveform that directly produces stimulation of the tissue; the parameters of the charge-balancing phase (described below) can similarly be controlled. The patient and/or the clinician can also optionally control overall duration and pattern of treatment.

TABLE 1

| Stimulation Parameter | |
| --- | --- |
| Pulse Amplitude: | 0 to 20 mA |
| Pulse Frequency: | 0 to 2000 Hz |
| Pulse Width: | 0 to 2 ms |

The implantable neural stimulator module 114 or RF pulse generator module 114 may be initially programmed to meet the specific parameter settings for each individual patient during the initial implantation procedure. Because medical conditions or the body itself can change over time, the ability to re-adjust the parameter settings may be beneficial to ensure ongoing efficacy of the neural modulation therapy.

The programmer module 102 may be functionally a smart device and associated application. The smart device hardware may include a CPU 206 and be used as a vehicle to handle touchscreen input on a graphical user interface (GUI) 204, for processing and storing data.

The RF pulse generator module 106 may be connected via wired connection 108 to an external TX antenna 110. Alternatively, both the antenna and the RF pulse generator are located subcutaneously (not shown).

The signals sent by RF pulse generator module 106 to the implanted stimulator 114 may include both power and parameter-setting attributes in regards to stimulus waveform, amplitude, pulse width, and frequency. The RF pulse generator module 106 can also function as a wireless receiving unit that receives feedback signals from the implanted stimulator module 114. To that end, the RF pulse generator module 106 may contain microelectronics or other circuitry to handle the generation of the signals transmitted to the stimulator module 114 as well as handle feedback signals, such as those from the stimulator module 114. For example, the RF pulse generator module 106 may comprise controller subsystem 214, high-frequency oscillator 218, RF amplifier 216, a RF switch, and a feedback subsystem 212.

The controller subsystem 214 may include a CPU 230 to handle data processing, a memory subsystem 228 such as a local memory, communication subsystem 234 to communicate with programmer module 102 (including receiving stimulation parameters from programmer module), pulse generator circuitry 236, and digital/analog (D/A) converters 232.

The controller subsystem 214 may be used by the patient and/or the clinician to control the stimulation parameter settings (for example, by controlling the parameters of the signal sent from RF pulse generator module 106 to neural stimulator module 114). These parameter settings can affect, for example, the power, current level, or shape of the one or more electrical pulses. The programming of the stimulation parameters can be performed using the programming module 102, as described above, to set the repetition rate, pulse width, amplitude, and waveform that will be transmitted by RF energy to the receive (RX) antenna 238, typically a dipole antenna (although other types may be used), in the wireless implanted neural stimulator module 214. The clinician may have the option of locking and/or hiding certain settings within the programmer interface, thus limiting the patient's ability to view or adjust certain parameters because adjustment of certain parameters may require detailed medical knowledge of neurophysiology, neuroanatomy, protocols for neural modulation, and safety limits of electrical stimulation.

The controller subsystem 214 may store received parameter settings in the local memory subsystem 228, until the parameter settings are modified by new input data received from the programming module 102. The CPU 206 may use the parameters stored in the local memory to control the pulse generator circuitry 236 to generate a stimulus waveform that is modulated by a high frequency oscillator 218 in the range from 300 MHz to 8 GHz. The resulting RF signal may then be amplified by RF amplifier 226 and then sent through an RF switch 223 to the TX antenna 110 to reach through depths of tissue to the RX antenna 238.

In some implementations, the RF signal sent by TX antenna 110 may simply be a power transmission signal used by stimulator module 114 to generate electric pulses. In other implementations, a telemetry signal may also be transmitted to the stimulator module 114 to send instructions about the various operations of the stimulator module 114. The telemetry signal may be sent by the modulation of the carrier signal (through the skin if external, or through other body tissues if the pulse generator module 106 is implanted subcutaneously). The telemetry signal is used to modulate the carrier signal (a high frequency signal) that is coupled onto the implanted antenna(s) 238 and does not interfere with the input received on the same lead to power the implant. In one embodiment the telemetry signal and powering signal are combined into one signal, where the RF telemetry signal is used to modulate the RF powering signal, and thus the implanted stimulator is powered directly by the received telemetry signal; separate subsystems in the stimulator harness the power contained in the signal and interpret the data content of the signal.

The RF switch 223 may be a multipurpose device such as a dual directional coupler, which passes the relatively high amplitude, extremely short duration RF pulse to the TX antenna 110 with minimal insertion loss while simultaneously providing two low-level outputs to feedback subsystem 212; one output delivers a forward power signal to the feedback subsystem 212, where the forward power signal is an attenuated version of the RF pulse sent to the TX antenna 110, and the other output delivers a reverse power signal to a different port of the feedback subsystem 212, where reverse power is an attenuated version of the reflected RF energy from the TX Antenna 110.

During the on-cycle time (when an RF signal is being transmitted to stimulator 114), the RF switch 223 is set to send the forward power signal to feedback subsystem. During the off-cycle time (when an RF signal is not being transmitted to the stimulator module 114), the RF switch 223 can change to a receiving mode in which the reflected RF energy and/or RF signals from the stimulator module 114 are received to be analyzed in the feedback subsystem 212.

The feedback subsystem 212 of the RF pulse generator module 106 may include reception circuitry to receive and extract telemetry or other feedback signals from the stimulator 114 and/or reflected RF energy from the signal sent by TX antenna 110. The feedback subsystem may include an amplifier 226, a filter 224, a demodulator 222, and an A/D converter 220.

The feedback subsystem 212 receives the forward power signal and converts this high-frequency AC signal to a DC level that can be sampled and sent to the controller subsystem 214. In this way the characteristics of the generated RF pulse can be compared to a reference signal within the controller subsystem 214. If a disparity (error) exists in any parameter, the controller subsystem 214 can adjust the output to the RF pulse generator 106. The nature of the adjustment can be, for example, proportional to the computed error. The controller subsystem 214 can incorporate additional inputs and limits on its adjustment scheme such as the signal amplitude of the reverse power and any predetermined maximum or minimum values for various pulse parameters.

The reverse power signal can be used to detect fault conditions in the RF-power delivery system. In an ideal condition, when TX antenna 110 has perfectly matched impedance to the tissue that it contacts, the electromagnetic waves generated from the RF pulse generator 106 pass unimpeded from the TX antenna 110 into the body tissue. However, in real-world applications a large degree of variability may exist in the body types of users, types of clothing worn, and positioning of the antenna 110 relative to the body surface. Since the impedance of the antenna 110 depends on the relative permittivity of the underlying tissue and any intervening materials, and also depends on the overall separation distance of the antenna from the skin, in any given application there can be an impedance mismatch at the interface of the TX antenna 110 with the body surface. When such a mismatch occurs, the electromagnetic waves sent from the RF pulse generator 106 are partially reflected at this interface, and this reflected energy propagates backward through the antenna feed.

The dual directional coupler RF switch 223 may prevent the reflected RF energy propagating back into the amplifier 226, and may attenuate this reflected RF signal and send the attenuated signal as the reverse power signal to the feedback subsystem 212. The feedback subsystem 212 can convert this high-frequency AC signal to a DC level that can be sampled and sent to the controller subsystem 214. The controller subsystem 214 can then calculate the ratio of the amplitude of the reverse power signal to the amplitude of the forward power signal. The ratio of the amplitude of reverse power signal to the amplitude level of forward power may indicate severity of the impedance mismatch.

In order to sense impedance mismatch conditions, the controller subsystem 214 can measure the reflected-power ratio in real time, and according to preset thresholds for this measurement, the controller subsystem 214 can modify the level of RF power generated by the RF pulse generator 106. For example, for a moderate degree of reflected power the course of action can be for the controller subsystem 214 to increase the amplitude of RF power sent to the TX antenna 110, as would be needed to compensate for slightly non-optimum but acceptable TX antenna coupling to the body. For higher ratios of reflected power, the course of action can be to prevent operation of the RF pulse generator 106 and set a fault code to indicate that the TX antenna 110 has little or no coupling with the body. This type of reflected-power fault condition can also be generated by a poor or broken connection to the TX antenna. In either case, it may be desirable to stop RF transmission when the reflected-power ratio is above a defined threshold, because internally reflected power can lead to unwanted heating of internal components, and this fault condition means the system cannot deliver sufficient power to the implanted wireless neural stimulator and thus cannot deliver therapy to the user.

The controller 242 of the stimulator 114 may transmit informational signals, such as a telemetry signal, through the antenna 238 to communicate with the RF pulse generator module 106 during its receive cycle. For example, the telemetry signal from the stimulator 114 may be coupled to the modulated signal on the dipole antenna(s) 238, during the on and off state of the transistor circuit to enable or disable a waveform that produces the corresponding RF bursts necessary to transmit to the external (or remotely implanted) pulse generator module 106. The antenna(s) 238 may be connected to electrodes 254 in contact with tissue to provide a return path for the transmitted signal. An A/D (not shown) converter can be used to transfer stored data to a serialized pattern that can be transmitted on the pulse modulated signal from the internal antenna(s) 238 of the neural stimulator.

A telemetry signal from the implanted wireless neural stimulator module 114 may include stimulus parameters such as the power or the amplitude of the current that is delivered to the tissue from the electrodes. The feedback signal can be transmitted to the RF pulse generator module 116 to indicate the strength of the stimulus at the nerve bundle by means of coupling the signal to the implanted RX antenna 238, which radiates the telemetry signal to the external (or remotely implanted) RF pulse generator module 106. The feedback signal can include either or both an analog and digital telemetry pulse modulated carrier signal. Data such as stimulation pulse parameters and measured characteristics of stimulator performance can be stored in an internal memory device within the implanted neural stimulator 114, and sent on the telemetry signal. The frequency of the carrier signal may be in the range of at 300 MHz to 8 GHz.

In the feedback subsystem 212, the telemetry signal can be down modulated using demodulator 222 and digitized by being processed through an analog to digital (A/D) converter 220. The digital telemetry signal may then be routed to a CPU 230 with embedded code, with the option to reprogram, to translate the signal into a corresponding current measurement in the tissue based on the amplitude of the received signal. The CPU 230 of the controller subsystem 214 can compare the reported stimulus parameters to those held in local memory 228 to verify the stimulator(s) 114 delivered the specified stimuli to tissue. For example, if the stimulator reports a lower current than was specified, the power level from the RF pulse generator module 106 can be increased so that the implanted neural stimulator 114 will have more available power for stimulation. The implanted neural stimulator 114 can generate telemetry data in real time, for example, at a rate of 8 kbits per second. All feedback data received from the implanted lead module 114 can be logged against time and sampled to be stored for retrieval to a remote monitoring system accessible by the health care professional for trending and statistical correlations.

The sequence of remotely programmable RF signals received by the internal antenna(s) 238 may be conditioned into waveforms that are controlled within the implantable stimulator 114 by the control subsystem 242 and routed to the appropriate electrodes 254 that are placed in proximity to the tissue to be stimulated. For instance, the RF signal transmitted from the RF pulse generator module 106 may be received by RX antenna 238 and processed by circuitry, such as waveform conditioning circuitry 240, within the implanted wireless neural stimulator module 114 to be converted into electrical pulses applied to the electrodes 254 through electrode interface 252. In some implementations, the implanted stimulator 114 contains between two to sixteen electrodes 254.

The waveform conditioning circuitry 240 may include a rectifier 244, which rectifies the signal received by the RX antenna 238. The rectified signal may be fed to the controller 242 for receiving encoded instructions from the RF pulse generator module 106. The rectifier signal may also be fed to a charge balance component 246 that is configured to create one or more electrical pulses based such that the one or more electrical pulses result in a substantially zero net charge at the one or more electrodes (that is, the pulses are charge balanced). The charge-balanced pulses are passed through the current limiter 248 to the electrode interface 252, which applies the pulses to the electrodes 254 as appropriate.

The current limiter 248 insures the current level of the pulses applied to the electrodes 254 is not above a threshold current level. In some implementations, an amplitude (for example, current level, voltage level, or power level) of the received RF pulse directly determines the amplitude of the stimulus. In this case, it may be particularly beneficial to include current limiter 248 to prevent excessive current or charge being delivered through the electrodes, although current limiter 248 may be used in other implementations where this is not the case. Generally, for a given electrode having several square millimeters surface area, it is the charge per phase that should be limited for safety (where the charge delivered by a stimulus phase is the integral of the current). But, in some cases, the limit can instead be placed on the current, where the maximum current multiplied by the maximum possible pulse duration is less than or equal to the maximum safe charge. More generally, the limiter 248 acts as a charge limiter that limits a characteristic (for example, current or duration) of the electrical pulses so that the charge per phase remains below a threshold level (typically, a safe-charge limit).

In the event the implanted wireless neural stimulator 114 receives a "strong" pulse of RF power sufficient to generate a stimulus that would exceed the predetermined safe-charge limit, the current limiter 248 can automatically limit or "clip" the stimulus phase to maintain the total charge of the phase within the safety limit. The current limiter 248 may be a passive current limiting component that cuts the signal to the electrodes 254 once the safe current limit (the threshold current level) is reached. Alternatively, or additionally, the current limiter 248 may communicate with the electrode interface 252 to turn off all electrodes 254 to prevent tissue damaging current levels.

A clipping event may trigger a current limiter feedback control mode. The action of clipping may cause the controller to send a threshold power data signal to the pulse generator 106. The feedback subsystem 212 detects the threshold power signal and demodulates the signal into data that is communicated to the controller subsystem 214. The controller subsystem 214 algorithms may act on this current-limiting condition by specifically reducing the RF power generated by the RF pulse generator, or cutting the power completely. In this way, the pulse generator 106 can reduce the RF power delivered to the body if the implanted wireless neural stimulator 114 reports it is receiving excess RF power.

The controller 250 of the stimulator 205 may communicate with the electrode interface 252 to control various aspects of the electrode setup and pulses applied to the electrodes 254. The electrode interface 252 may act as a multiplex and control the polarity and switching of each of the electrodes 254. For instance, in some implementations, the wireless stimulator 106 has multiple electrodes 254 in contact with tissue, and for a given stimulus the RF pulse generator module 106 can arbitrarily assign one or more electrodes to 1) act as a stimulating electrode, 2) act as a return electrode, or 3) be inactive by communication of assignment sent wirelessly with the parameter instructions, which the controller 250 uses to set electrode interface 252 as appropriate. It may be physiologically advantageous to assign, for example, one or two electrodes as stimulating electrodes and to assign all remaining electrodes as return electrodes.

Also, in some implementations, for a given stimulus pulse, the controller 250 may control the electrode interface 252 to divide the current arbitrarily (or according to instructions from pulse generator module 106) among the designated stimulating electrodes. This control over electrode assignment and current control can be advantageous because in practice the electrodes 254 may be spatially distributed along various neural structures, and through strategic selection of the stimulating electrode location and the proportion of current specified for each location, the aggregate current distribution in tissue can be modified to selectively activate specific neural targets. This strategy of current steering can improve the therapeutic effect for the patient.

In another implementation, the time course of stimuli may be arbitrarily manipulated. A given stimulus waveform may be initiated at a time T_start and terminated at a time T_final, and this time course may be synchronized across all stimulating and return electrodes; further, the frequency of repetition of this stimulus cycle may be synchronous for all the electrodes. However, controller 250, on its own or in response to instructions from pulse generator 106, can control electrode interface 252 to designate one or more subsets of electrodes to deliver stimulus waveforms with non-synchronous start and stop times, and the frequency of repetition of each stimulus cycle can be arbitrarily and independently specified.

For example, a stimulator having eight electrodes may be configured to have a subset of five electrodes, called set A, and a subset of three electrodes, called set B. Set A might be configured to use two of its electrodes as stimulating electrodes, with the remainder being return electrodes. Set B might be configured to have just one stimulating electrode. The controller 250 could then specify that set A deliver a stimulus phase with 3 mA current for a duration of 200 us followed by a 400 us charge-balancing phase. This stimulus cycle could be specified to repeat at a rate of 60 cycles per second. Then, for set B, the controller 250 could specify a stimulus phase with 1 mA current for duration of 500 us followed by a 800 us charge-balancing phase. The repetition rate for the set-B stimulus cycle can be set independently of set A, say for example it could be specified at 25 cycles per second. Or, if the controller 250 was configured to match the repetition rate for set B to that of set A, for such a case the controller 250 can specify the relative start times of the stimulus cycles to be coincident in time or to be arbitrarily offset from one another by some delay interval.

In some implementations, the controller 250 can arbitrarily shape the stimulus waveform amplitude, and may do so in response to instructions from pulse generator 106. The stimulus phase may be delivered by a constant-current source or a constant-voltage source, and this type of control may generate characteristic waveforms that are static, e.g. a constant-current source generates a characteristic rectangular pulse in which the current waveform has a very steep rise, a constant amplitude for the duration of the stimulus, and then a very steep return to baseline. Alternatively, or additionally, the controller 250 can increase or decrease the level of current at any time during the stimulus phase and/or during the charge-balancing phase. Thus, in some implementations, the controller 250 can deliver arbitrarily shaped stimulus waveforms such as a triangular pulse, sinusoidal pulse, or Gaussian pulse for example. Similarly, the charge-balancing phase can be arbitrarily amplitude-shaped, and similarly a leading anodic pulse (prior to the stimulus phase) may also be amplitude-shaped.

As described above, the stimulator 114 may include a charge-balancing component 246. Generally, for constant current stimulation pulses, pulses should be charge balanced by having the amount of cathodic current should equal the amount of anodic current, which is typically called biphasic stimulation. Charge density is the amount of current times the duration it is applied, and is typically expressed in the units $uC/cm^2$. In order to avoid the irreversible electrochemical reactions such as pH change, electrode dissolution as well as tissue destruction, no net charge should appear at the electrode-electrolyte interface, and it is generally acceptable to have a charge density less than 30 $uC/cm^2$. Biphasic stimulating current pulses ensure that no net charge appears at the electrode after each stimulation cycle and the electrochemical processes are balanced to prevent net dc currents. Neural stimulator 114 may be designed to ensure that the resulting stimulus waveform has a net zero charge. Charge balanced stimuli are thought to have minimal damaging effects on tissue by reducing or eliminating electrochemical reaction products created at the electrode-tissue interface.

A stimulus pulse may have a negative-voltage or current, called the cathodic phase of the waveform. Stimulating electrodes may have both cathodic and anodic phases at different times during the stimulus cycle. An electrode that delivers a negative current with sufficient amplitude to stimulate adjacent neural tissue is called a "stimulating electrode." During the stimulus phase the stimulating electrode acts as a current sink. One or more additional electrodes act as a current source and these electrodes are called "return electrodes." Return electrodes are placed elsewhere in the tissue at some distance from the stimulating electrodes. When a typical negative stimulus phase is delivered to tissue at the stimulating electrode, the return electrode has a positive stimulus phase. During the subsequent charge-balancing phase, the polarities of each electrode are reversed.

In some implementations, the charge balance component 246 uses a blocking capacitor(s) placed electrically in series with the stimulating electrodes and body tissue, between the point of stimulus generation within the stimulator circuitry and the point of stimulus delivery to tissue. In this manner, a resistor-capacitor (RC) network may be formed. In a multi-electrode stimulator, one charge-balance capacitor(s) may be used for each electrode or a centralized capacitor(s) may be used within the stimulator circuitry prior to the point of electrode selection. The RC network can block direct current (DC), however it can also prevent low-frequency alternating current (AC) from passing to the tissue. The frequency below which the series RC network essentially blocks signals is commonly referred to as the cutoff frequency, and in one embodiment the design of the stimulator system may ensure the cutoff frequency is not above the fundamental frequency of the stimulus waveform. In this embodiment, the wireless stimulator may have a charge-balance capacitor with a value chosen according to the measured series resistance of the electrodes and the tissue environment in which the stimulator is implanted. By selecting a specific capacitance value the cutoff frequency of the RC network in this embodiment is at or below the fundamental frequency of the stimulus pulse.

In other implementations, the cutoff frequency may be chosen to be at or above the fundamental frequency of the stimulus, and in this scenario the stimulus waveform created prior to the charge-balance capacitor, called the drive waveform, may be designed to be non-stationary, where the envelope of the drive waveform is varied during the duration of the drive pulse. For example, in one embodiment, the initial amplitude of the drive waveform is set at an initial amplitude Vi, and the amplitude is increased during the duration of the pulse until it reaches a final value k*Vi. By changing the amplitude of the drive waveform over time, the shape of the stimulus waveform passed through the charge-balance capacitor is also modified. The shape of the stimulus waveform may be modified in this fashion to create a physiologically advantageous stimulus.

In some implementations, the wireless neural stimulator module 114 may create a drive-waveform envelope that follows the envelope of the RF pulse received by the receiving dipole antenna(s) 238. In this case, the RF pulse generator module 106 can directly control the envelope of the drive waveform within the wireless neural stimulator 114, and thus no energy storage may be required inside the stimulator itself. In this implementation, the stimulator circuitry may modify the envelope of the drive waveform or may pass it directly to the charge-balance capacitor and/or electrode-selection stage.

In some implementations, the implanted neural stimulator 114 may deliver a single-phase drive waveform to the charge balance capacitor or it may deliver multiphase drive waveforms. In the case of a single-phase drive waveform, for example, a negative-going rectangular pulse, this pulse comprises the physiological stimulus phase, and the charge-balance capacitor is polarized (charged) during this phase. After the drive pulse is completed, the charge balancing function is performed solely by the passive discharge of the charge-balance capacitor, where is dissipates its charge through the tissue in an opposite polarity relative to the preceding stimulus. In one implementation, a resistor within the stimulator facilitates the discharge of the charge-balance capacitor. In some implementations, using a passive discharge phase, the capacitor may allow virtually complete discharge prior to the onset of the subsequent stimulus pulse.

In the case of multiphase drive waveforms the wireless stimulator may perform internal switching to pass negative-going or positive-going pulses (phases) to the charge-balance capacitor. These pulses may be delivered in any sequence and with varying amplitudes and waveform shapes to achieve a desired physiological effect. For example, the stimulus phase may be followed by an actively driven charge-balancing phase, and/or the stimulus phase may be preceded by an opposite phase. Preceding the stimulus with an opposite-polarity phase, for example, can have the advantage of reducing the amplitude of the stimulus phase required to excite tissue.

In some implementations, the amplitude and timing of stimulus and charge-balancing phases is controlled by the amplitude and timing of RF pulses from the RF pulse generator module 106, and in others this control may be administered internally by circuitry onboard the wireless stimulator 114, such as controller 250. In the case of onboard control, the amplitude and timing may be specified or modified by data commands delivered from the pulse generator module 106.

Figure 3:
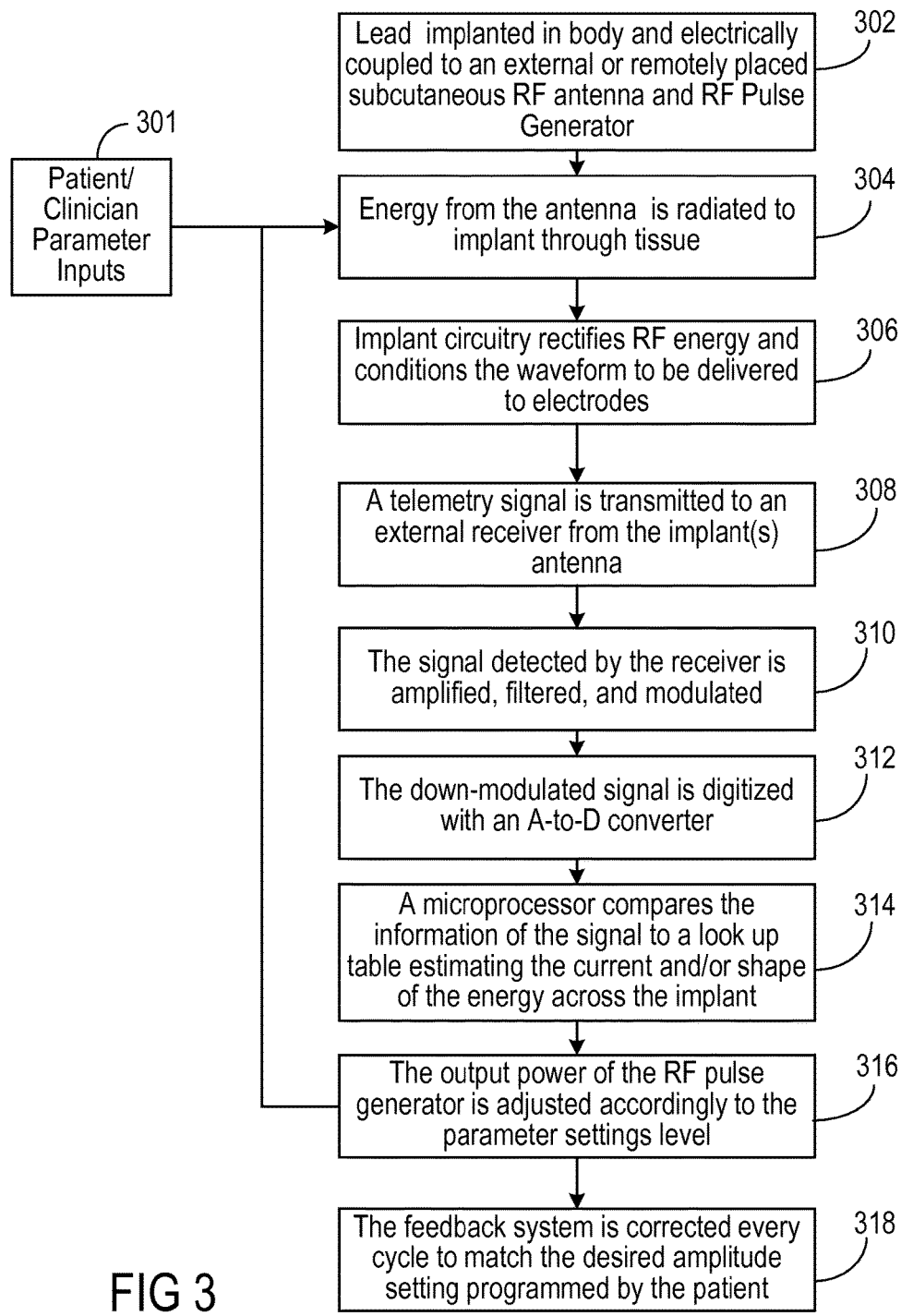
FIG. 3 is a flowchart showing an example of the operation of the wireless neural stimulator system.

FIG. 3 is a flowchart showing an example of an operation of the neural stimulator system. In block 302, the wireless neural stimulator 114 is implanted in proximity to nerve bundles and is coupled to the electric field produced by the TX antenna 110. That is, the pulse generator module 106 and the TX antenna 110 are positioned in such a way (for example, in proximity to the patient) that the TX antenna 110 is electrically radiatively coupled with the implanted RX antenna 238 of the neural stimulator 114. In certain implementations, both the antenna 110 and the RF pulse generator 106 are located subcutaneously. In other implementations, the antenna 110 and the RF pulse generator 106 are located external to the patient's body. In this case, the TX antenna 110 may be coupled directly to the patient's skin.

Energy from the RF pulse generator is radiated to the implanted wireless neural stimulator 114 from the antenna 110 through tissue, as shown in block 304. The energy radiated may be controlled by the Patient/Clinician Parameter inputs in block 301. In some instances, the parameter settings can be adjusted in an open loop fashion by the patient or clinician, who would adjust the parameter inputs in block 301 to the system.

The wireless implanted stimulator 114 uses the received energy to generate electrical pulses to be applied to the neural tissue through the electrodes 238. For instance, the stimulator 114 may contain circuitry that rectifies the received RF energy and conditions the waveform to charge balance the energy delivered to the electrodes to stimulate the targeted nerves or tissues, as shown in block 306. The implanted stimulator 114 communicates with the pulse generator 106 by using antenna 238 to send a telemetry signal, as shown in block 308. The telemetry signal may contain information about parameters of the electrical pulses applied to the electrodes, such as the impedance of the electrodes, whether the safe current limit has been reached, or the amplitude of the current that is presented to the tissue from the electrodes.

In block 310, the RF pulse generator 106 detects amplifies, filters and modulates the received telemetry signal using amplifier 226, filter 224, and demodulator 222, respectively. The A/D converter 230 then digitizes the resulting analog signal, as shown in 312. The digital telemetry signal is routed to CPU 230, which determines whether the parameters of the signal sent to the stimulator 114 need to be adjusted based on the digital telemetry signal. For instance, in block 314, the CPU 230 compares the information of the digital signal to a look-up table, which may indicate an appropriate change in stimulation parameters. The indicated change may be, for example, a change in the current level of the pulses applied to the electrodes. As a result, the CPU may change the output power of the signal sent to stimulator 114 so as to adjust the current applied by the electrodes 254, as shown in block 316.

Thus, for instance, the CPU 230 may adjust parameters of the signal sent to the stimulator 114 every cycle to match the desired current amplitude setting programmed by the patient, as shown in block 318. The status of the stimulator system may be sampled in real time at a rate of 8 kbits per second of telemetry data. All feedback data received from the stimulator 114 can be maintained against time and sampled per minute to be stored for download or upload to a remote monitoring system accessible by the health care professional for trending and statistical correlations in block 318. If operated in an open loop fashion, the stimulator system operation may be reduced to just the functional elements shown in blocks 302, 304, 306, and 308, and the patient uses their judgment to adjust parameter settings rather than the closed looped feedback from the implanted device.

Figure 4:
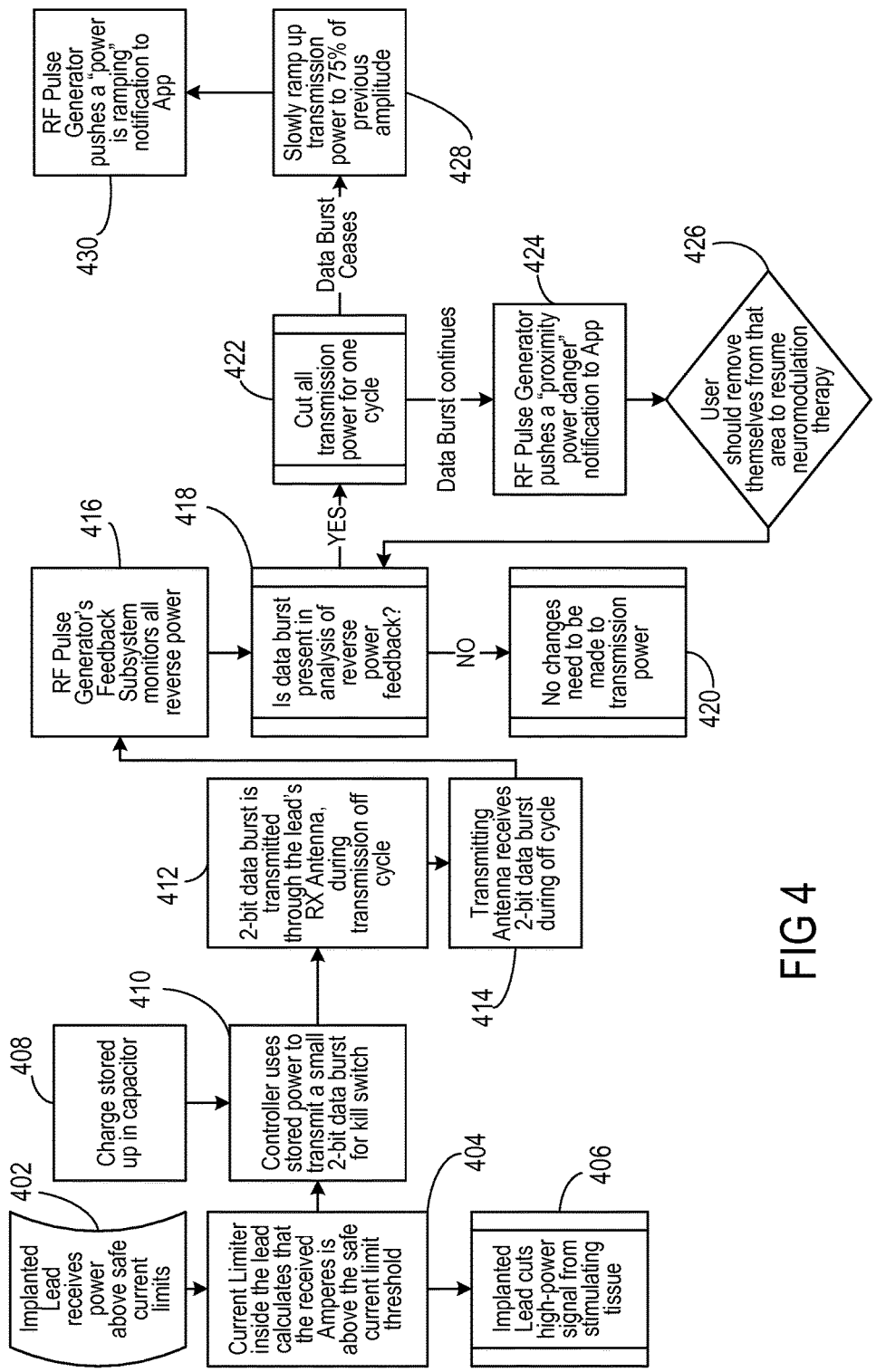
FIG. 4 depicts a flow chart showing an example of the operation of the system when the current level at the electrodes is above the threshold limit.

FIG. 4 depicts a flow chart showing an example of an operation of the system when the current level at the electrodes 254 is above a threshold limit. In certain instances, the implanted wireless neural stimulator 114 may receive an input power signal with a current level above an established safe current limit, as shown in block 402. For instance, the current limiter 248 may determine the current is above an established tissue-safe limit of amperes, as shown in block 404. If the current limiter senses that the current is above the threshold, it may stop the high-power signal from damaging surrounding tissue in contact with the electrodes as shown in block 406, the operations of which are as described above in association with FIGS. 2A and 2B.

A capacitor may store excess power, as shown in block 408. When the current limiter senses the current is above the threshold, the controller 250 may use the excess power available to transmit a small 2-bit data burst back to the RF pulse generator 106, as shown in block 410. The 2-bit data burst may be transmitted through the implanted wireless neural stimulator's antenna(s) 238 during the RF pulse generator's receive cycle, as shown in block 412. The RF pulse generator antenna 110 may receive the 2-bit data burst during its receive cycle, as shown in block 414, at a rate of 8 kbps, and may relay the data burst back to the RF pulse generator's feedback subsystem 212 which is monitoring all reverse power, as shown in block 416. The CPU 230 may analyze signals from feedback subsystem 202, as shown in block 418 and if there is no data burst present, no changes may be made to the stimulation parameters, as shown in block 420. If the data burst is present in the analysis, the CPU 230 can cut all transmission power for one cycle, as shown in block 422.

If the data burst continues, the RF pulse generator 106 may push a "proximity power danger" notification to the application on the programmer module 102, as shown in block 424. This proximity danger notification occurs because the RF pulse generator has ceased its transmission of power. This notification means an unauthorized form of energy is powering the implant above safe levels. The application may alert the user of the danger and that the user should leave the immediate area to resume neural modulation therapy, as shown in block 426. If after one cycle the data burst has stopped, the RF pulse generator 106 may slowly ramp up the transmission power in increments, for example from 5% to 75% of previous current amplitude levels, as shown in block 428. The user can then manually adjust current amplitude level to go higher at the user's own risk. During the ramp up, the RF pulse generator 106 may notify the application of its progress and the application may notify the user that there was an unsafe power level and the system is ramping back up, as shown in block 430.

Figure 5:
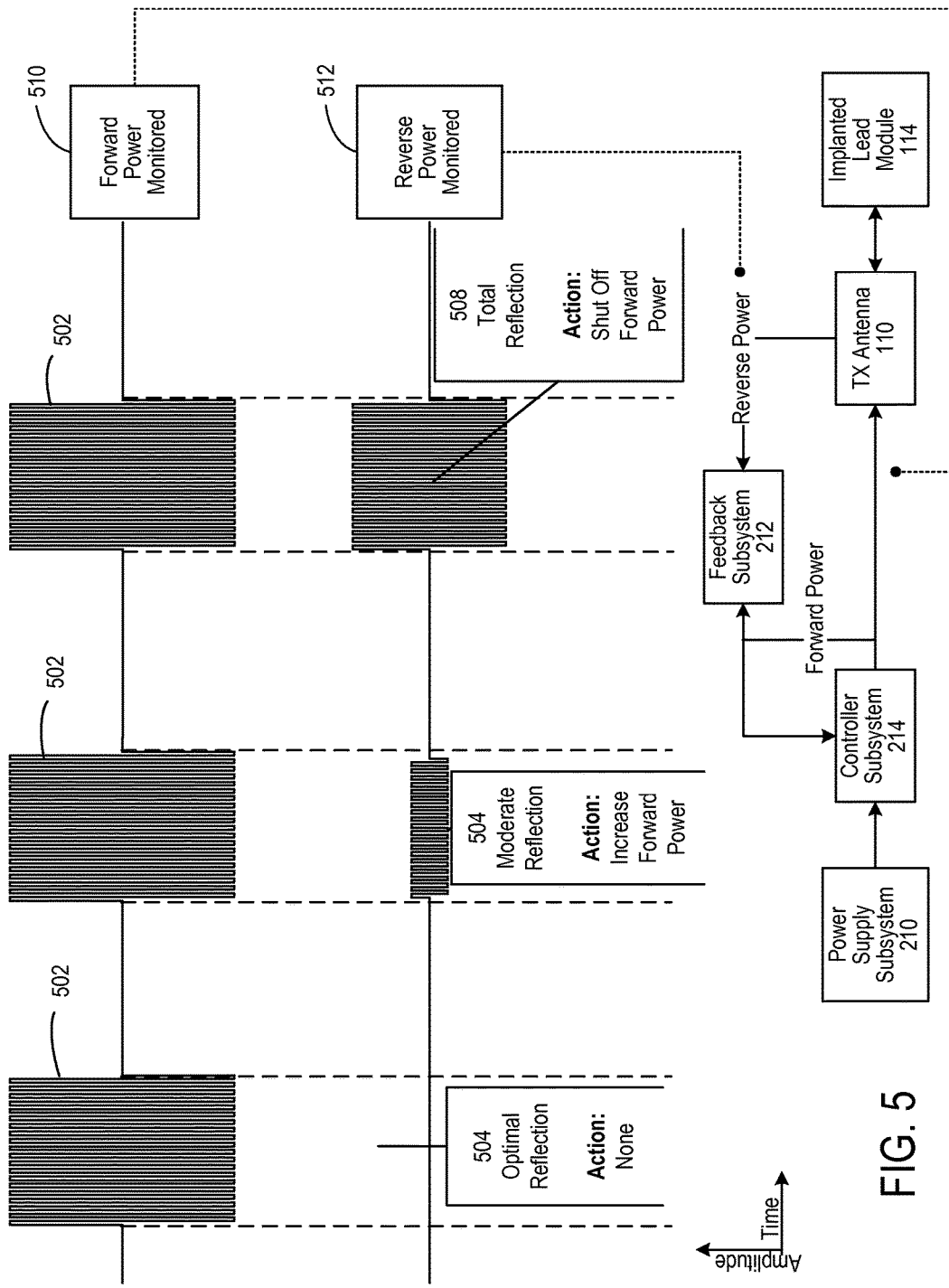
FIG. 5 is a diagram showing examples of signals that may be used to detect an impedance mismatch.

FIG. 5 is a diagram showing examples of signals that may be used to detect an impedance mismatch. As described above, a forward power signal and a reverse power signal may be used to detect an impedance mismatch. For instance, a RF pulse 502 generated by the RF pulse generator may pass through a device such as a dual directional coupler to the TX antenna 110. The TX antenna 110 then radiates the RF signal into the body, where the energy is received by the implanted wireless neural stimulator 114 and converted into a tissue-stimulating pulse. The coupler passes an attenuated version of this RF signal, forward power 510, to feedback subsystem 212. The feedback subsystem 212 demodulates the AC signal and computes the amplitude of the forward RF power, and this data is passed to controller subsystem 214. Similarly the dual directional coupler (or similar component) also receives RF energy reflected back from the TX antenna 110 and passes an attenuated version of this RF signal, reverse power 512, to feedback subsystem 212. The feedback subsystem 212 demodulates the AC signal and computes the amplitude of the reflected RF power, and this data is passed to controller subsystem 214.

In the optimal case, when the TX antenna 110 may be perfectly impedance-matched to the body so that the RF energy passes unimpeded across the interface of the TX antenna 110 to the body, and no RF energy is reflected at the interface. Thus, in this optimal case, the reverse power 512 may have close to zero amplitude as shown by signal 504, and the ratio of reverse power 512 to forward power 510 is zero. In this circumstance, no error condition exists, and the controller 214 sets a system message that operation is optimal.

In practice, the impedance match of the TX antenna 204 to the body may not be optimal, and some energy of the RF pulse 502 is reflected from the interface of the TX antenna 110 and the body. This can occur for example if the TX antenna 110 is held somewhat away from the skin by a piece of clothing. This non-optimal antenna coupling causes a small portion of the forward RF energy to be reflected at the interface, and this is depicted as signal 506. In this case, the ratio of reverse power 512 to forward power 510 is small, but a small ratio implies that most of the RF energy is still radiated from the TX antenna 110, so this condition is acceptable within the control algorithm. This determination of acceptable reflection ratio may be made within controller subsystem 214 based upon a programmed threshold, and the controller subsystem 214 may generate a low-priority alert to be sent to the user interface. In addition, the controller subsystem 214 sensing the condition of a small reflection ratio, may moderately increase the amplitude of the RF pulse 502 to compensate for the moderate loss of forward energy transfer to the implanted wireless neural stimulator 114.

During daily operational use, the TX antenna 110 might be accidentally removed from the body entirely, in which case the TX antenna will have very poor coupling to the body (if any). In this or other circumstances, a relatively high proportion of the RF pulse energy is reflected as signal 508 from the TX antenna 110 and fed backward into the RF-powering system. Similarly, this phenomenon can occur if the connection to the TX antenna is physically broken, in which case virtually 100% of the RF energy is reflected backward from the point of the break. In such cases, the ratio of reverse power 512 to forward power 510 is very high, and the controller subsystem 214 will determine the ratio has exceeded the threshold of acceptance. In this case, the controller subsystem 214 may prevent any further RF pulses from being generated. The shutdown of the RF pulse generator module 106 may be reported to the user interface to inform the user that stimulation therapy cannot be delivered.

Figure 6:
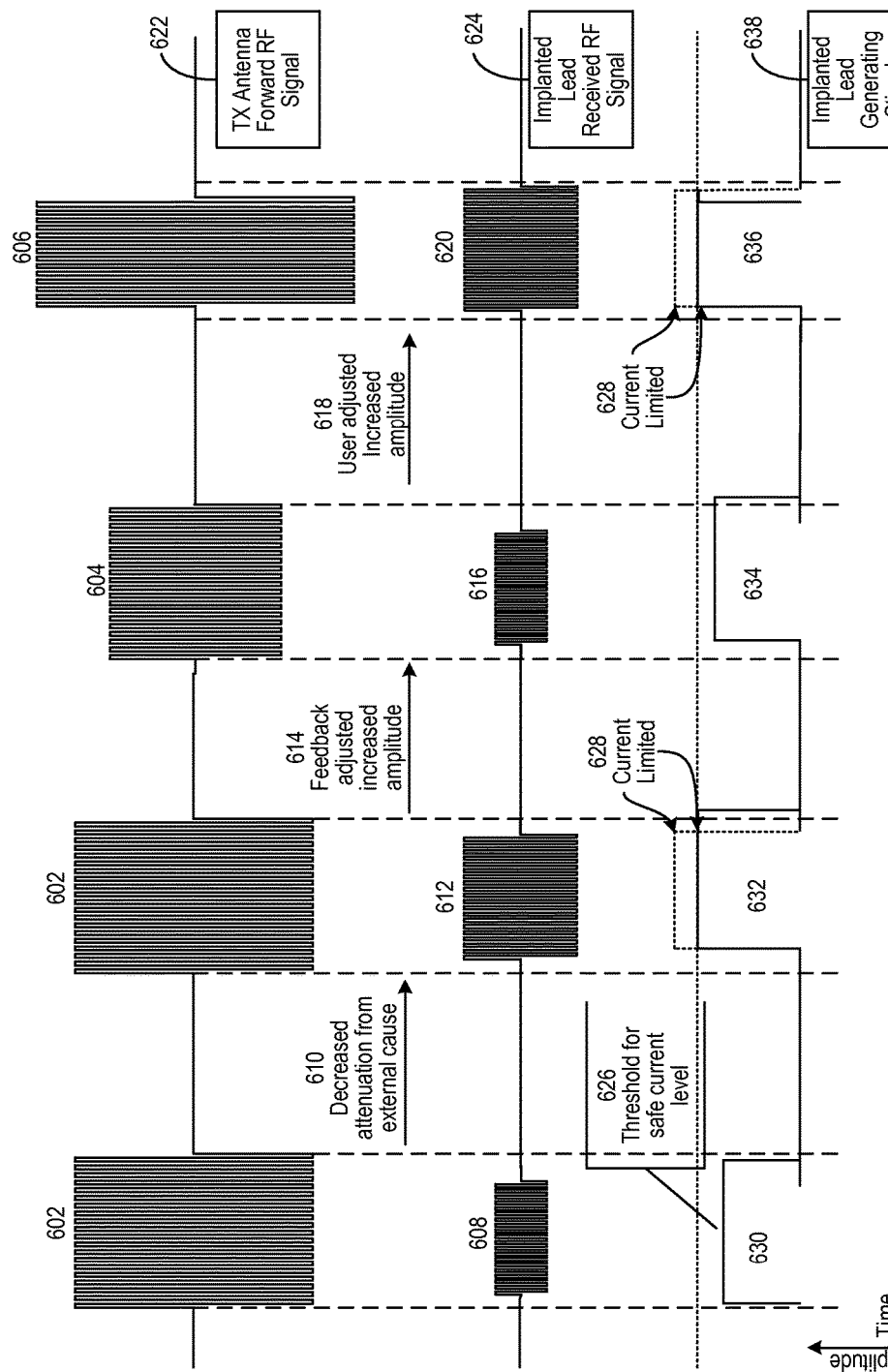
FIG. 6 is a diagram showing examples of signals that may be employed during operation of the wireless neural stimulator system.

FIG. 6 is a diagram showing examples of signals that may be employed during operation of the neural stimulator system. According to some implementations, the amplitude of the RF pulse 602 received by the implanted wireless neural stimulator 114 can directly control the amplitude of the stimulus 630 delivered to tissue. The duration of the RF pulse 608 corresponds to the specified pulse width of the stimulus 630. During normal operation the RF pulse generator module 106 sends an RF pulse waveform 602 via TX antenna 110 into the body, and RF pulse waveform 608 may represent the corresponding RF pulse received by implanted wireless neural stimulator 114. In this instance the received power has an amplitude suitable for generating a safe stimulus pulse 630. The stimulus pulse 630 is below the safety threshold 626, and no error condition exists. In another example, the attenuation between the TX antenna 110 and the implanted wireless neural stimulator 114 has been unexpectedly reduced, for example due to the user repositioning the TX antenna 110. This reduced attenuation can lead to increased amplitude in the RF pulse waveform 612 being received at the neural stimulator 114. Although the RF pulse 602 is generated with the same amplitude as before, the improved RF coupling between the TX antenna 110 and the implanted wireless neural stimulator 114 can cause the received RF pulse 612 to be larger in amplitude. Implanted wireless neural stimulator 114 in this situation may generate a larger stimulus 632 in response to the increase in received RF pulse 612. However, in this example, the received power 612 is capable of generating a stimulus 632 that exceeds the prudent safety limit for tissue. In this situation, the current limiter feedback control mode can operate to clip the waveform of the stimulus pulse 632 such that the stimulus delivered is held within the predetermined safety limit 626. The clipping event 628 may be communicated through the feedback subsystem 212 as described above, and subsequently controller subsystem 214 can reduce the amplitude specified for the RF pulse. As a result, the subsequent RF pulse 604 is reduced in amplitude, and correspondingly the amplitude of the received RF pulse 616 is reduced to a suitable level (non-clipping level). In this fashion, the current limiter feedback control mode may operate to reduce the RF power delivered to the body if the implanted wireless neural stimulator 114 receives excess RF power.

In another example, the RF pulse waveform 606 depicts a higher amplitude RF pulse generated as a result of user input to the user interface. In this circumstance, the RF pulse 620 received by the implanted wireless neural stimulator 14 is increased in amplitude, and similarly current limiter feedback mode operates to prevent stimulus 636 from exceeding safety limit 626. Once again, this clipping event 628 may be communicated through the feedback subsystem 212, and subsequently controller subsystem 214 may reduce the amplitude of the RF pulse, thus overriding the user input. The reduced RF pulse 604 can produce correspondingly smaller amplitudes of the received waveforms 616, and clipping of the stimulus current may no longer be required to keep the current within the safety limit. In this fashion, the current limiter feedback may reduce the RF power delivered to the body if the implanted wireless neural stimulator 114 reports it is receiving excess RF power.

FIG. 7 is a flow chart showing a process for the user to control the implantable wireless neural stimulator through the programmer in an open loop feedback system. In one implementation of the system, the user has a wireless neural stimulator implanted in their body, the RF pulse generator 106 sends the stimulating pulse power wirelessly to the stimulator 114, and an application on the programmer module 102 (for example, a smart device) is communicating with the RF pulse generator 106. In this implementation, if a user wants to observe the current status of the functioning pulse generator, as shown in block 702, the user may open the application, as shown in block 704. The application can use Bluetooth protocols built into the smart device to interrogate the pulse generator, as shown in block 706. The RF pulse generator 106 may authenticate the identity of the smart device and serialized patient assigned secure iteration of the application, as shown in block 708. The authentication process may utilize a unique key to the patient specific RF pulse generator serial number. The application can be customized with the patient specific unique key through the Manufacturer Representative who has programmed the initial patient settings for the stimulation system, as shown in block 720. If the RF pulse generator rejects the authentication it may inform the application that the code is invalid, as shown in block 718 and needs the authentication provided by the authorized individual with security clearance from the device manufacturer, known as the "Manufacturer's Representative," as shown in block 722. In an implementation, only the Manufacturer's Representative can have access to the security code needed to change the application's stored RF pulse generator unique ID. If the RF pulse generator authentication system passes, the pulse generator module 106 sends back all of the data that has been logged since the last sync, as shown in block 710. The application may then register the most current information and transmit the information to a 3rd party in a secure fashion, as shown in 712. The application may maintain a database that logs all system diagnostic results and values, the changes in settings by the user and the feedback system, and the global runtime history, as shown in block 714. The application may then display relevant data to the user, as shown in block 716; including the battery capacity, current program parameter, running time, pulse width, frequency, amplitude, and the status of the feedback system.

Figure 8A:
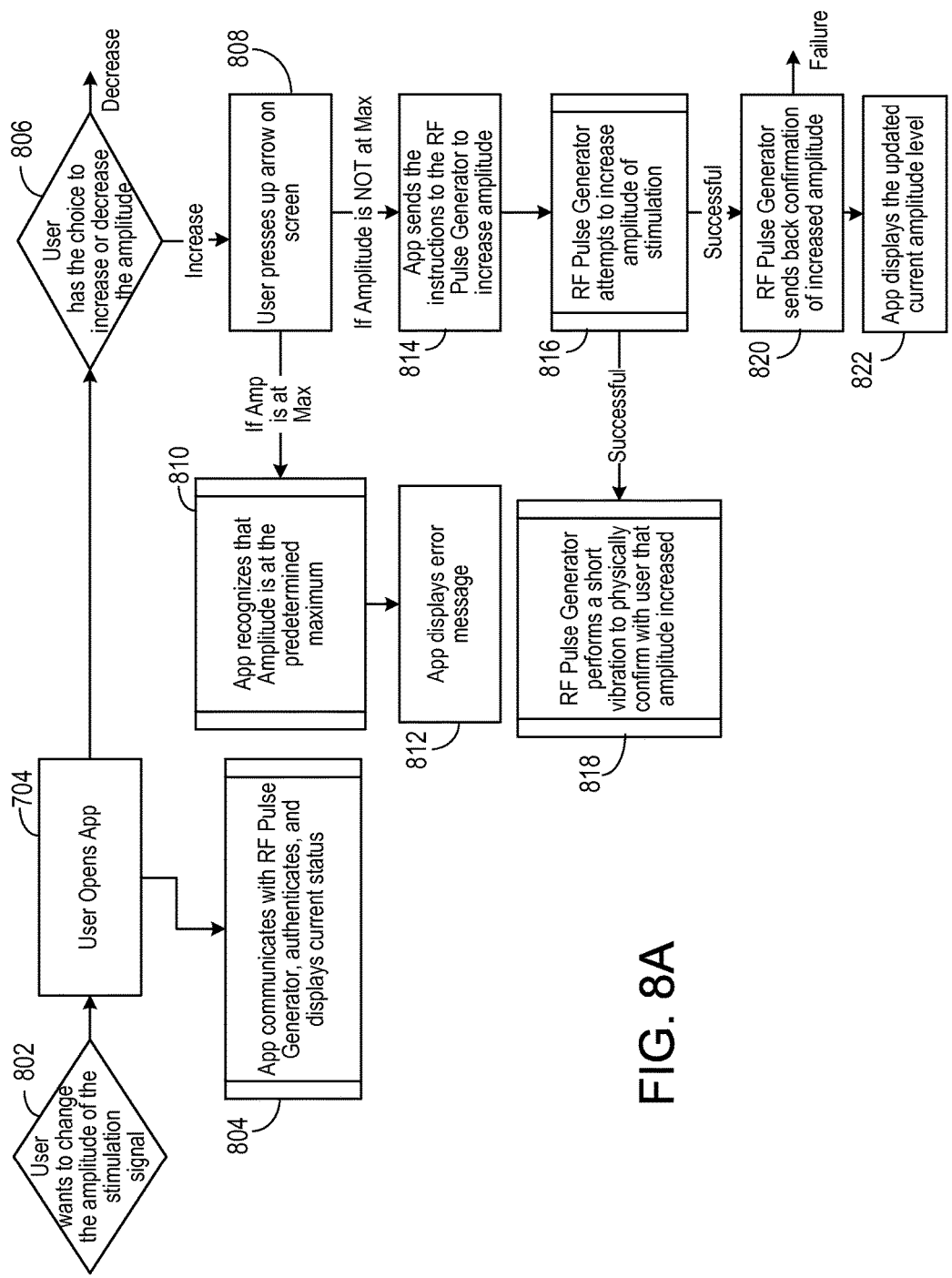
FIGS. 8A and 8B show another example flow chart of a process for the user to control the wireless stimulator with limitations on the lower and upper limits of current amplitude.
Figure 8B:
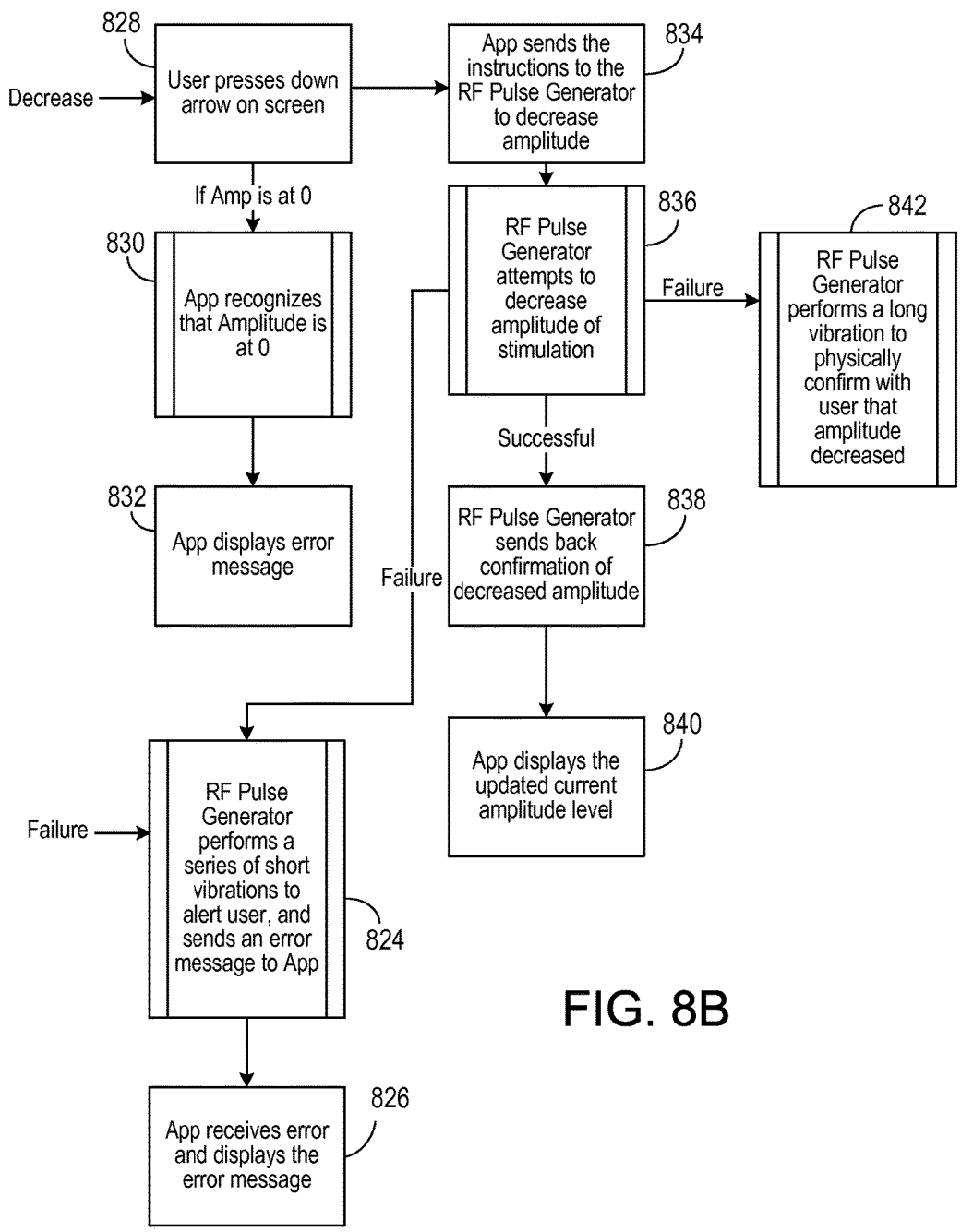

FIGS. 8A and 8B show another example flow chart of a process for the user to control the wireless stimulator with limitations on the lower and upper limits of current amplitude. The user wants to change the amplitude of the stimulation signal, as shown in block 802. The user may open the application, as show in block 704 and the application may go through the process described in FIG. 7 to communicate with the RF pulse generator, authenticate successfully, and display the current status to the user, as shown in block 804. The application displays the stimulation amplitude as the most prevalent changeable interface option and displays two arrows with which the user can adjust the current amplitude. The user may make a decision based on their need for more or less stimulation in accordance with their pain levels, as shown in block 806. If the user chooses to increase the current amplitude, the user may press the up arrow on the application screen, as shown in block 808. The application can include safety maximum limiting algorithms, so if a request to increase current amplitude is recognized by the application as exceeding the preset safety maximum, as shown in block 810, then the application will display an error message, as shown in block 812 and will not communicate with the RF pulse generator module 106. If the user presses the up arrow, as shown in block 808 and the current amplitude request does not exceed the current amplitude maximum allowable value, then the application will send instructions to the RF pulse generator module 106 to increase amplitude, as shown in block 814. The RF pulse generator module 106 may then attempt to increase the current amplitude of stimulation, as shown in block 816. If the RF pulse generator is successful at increasing the current amplitude, the RF pulse generator module 106 may perform a short vibration to physically confirm with the user that the amplitude is increased, as shown in block 818. The RF pulse generator module 106 can also send back confirmation of increased amplitude to the application, as shown in block 820, and then the application may display the updated current amplitude level, as shown in block 822.

If the user decides to decrease the current amplitude level in block 806, the user can press the down arrow on the application, as shown in block 828. If the current amplitude level is already at zero, the application recognizes that the current amplitude cannot be decreased any further, as shown in block 830 and displays an error message to the user without communicating any data to the RF pulse generator, as shown in block 832. If the current amplitude level is not at zero, the application can send instructions to the RF pulse generator module 106 to decrease current amplitude level accordingly, as shown in block 834. The RF pulse generator may then attempt to decrease current amplitude level of stimulation RF pulse generator module 106 and, if successful, the RF pulse generator module 106 may perform a short vibration to physically confirm to the user that the current amplitude level has been decreased, as shown in block 842. The RF pulse generator module 106 can send back confirmation of the decreased current amplitude level to the application, as shown in block 838. The application then may display the updated current amplitude level, as indicated by block 840. If the current amplitude level decrease or increase fails, the RF pulse generator module 106 can perform a series of short vibrations to alert user, and send an error message to the application, as shown in block 824. The application receives the error and may display the data for the user's benefit, as shown in block 826.

Figure 9:
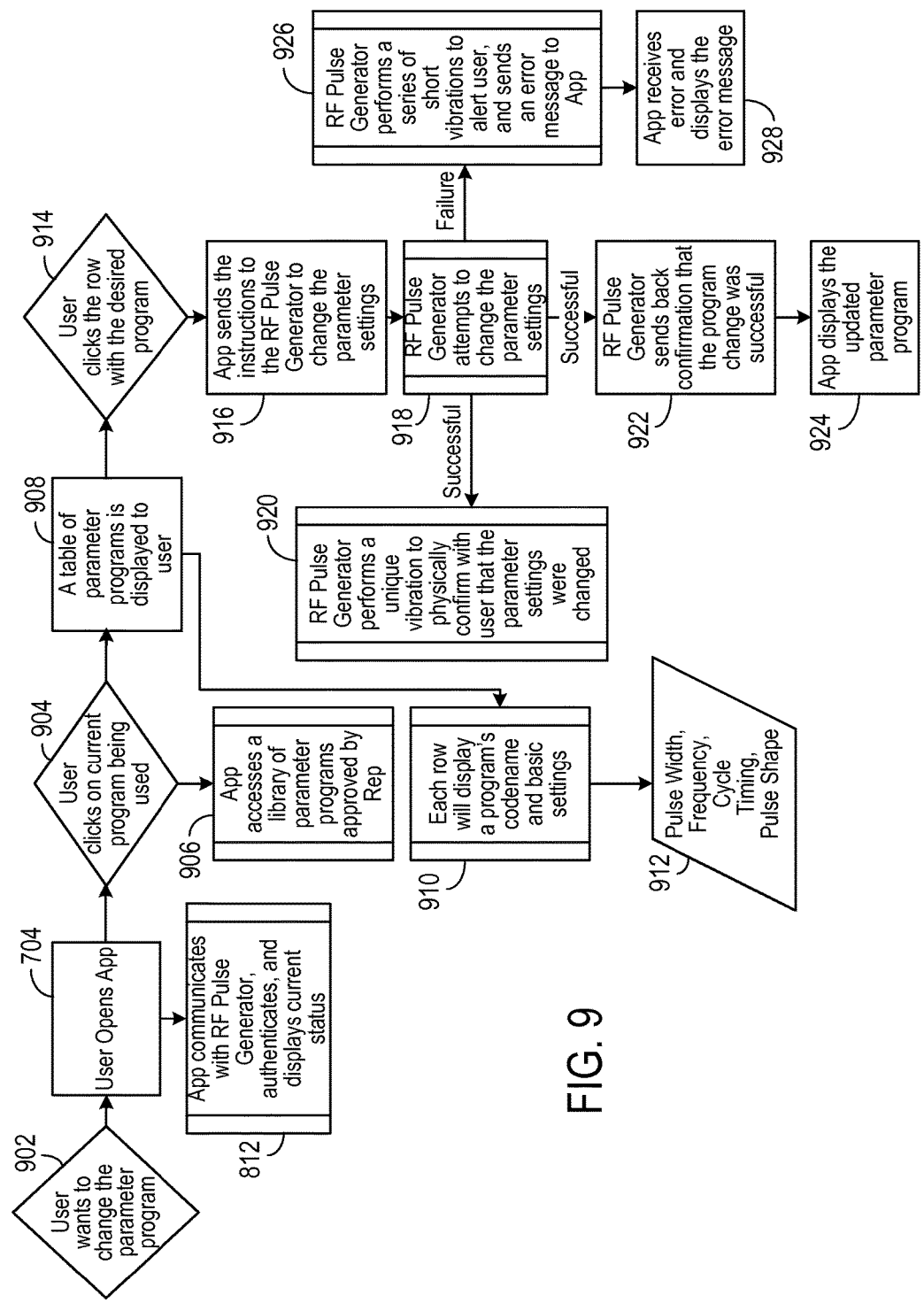
FIG. 9 is yet another example flow chart of a process for the user to control the wireless neural stimulator through preprogrammed parameter settings.

FIG. 9 is yet another example flow chart of a process for the user to control the wireless neural stimulator 114 through preprogrammed parameter settings. The user wants to change the parameter program, as indicated by block 902. When the user is implanted with a wireless neural stimulator or when the user visits the doctor, the Manufacturer's Representative may determine and provide the patient/user RF pulse generator with preset programs that have different stimulation parameters that will be used to treat the user. The user will then able to switch between the various parameter programs as needed. The user can open the application on their smart device, as indicated by block 704, which first follows the process described in FIG. 7, communicating with the RF pulse generator module 106, authenticating successfully, and displaying the current status of the RF pulse generator module 106, including the current program parameter settings, as indicated by block 812. In this implementation, through the user interface of the application, the user can select the program that they wish to use, as shown by block 904. The application may then access a library of pre-programmed parameters that have been approved by the Manufacturer's Representative for the user to interchange between as desired and in accordance with the management of their indication, as indicated by block 906. A table can be displayed to the user, as shown in block 908 and each row displays a program's codename and lists its basic parameter settings, as shown in block 910, which includes but is not limited to: pulse width, frequency, cycle timing, pulse shape, duration, feedback sensitivity, as shown in block 912. The user may then select the row containing the desired parameter preset program to be used, as shown in block 912. The application can send instructions to the RF pulse generator module 106 to change the parameter settings, as shown in block 916. The RF pulse generator module 106 may attempt to change the parameter settings 154. If the parameter settings are successfully changed, the RF pulse generator module 106 can perform a unique vibration pattern to physically confirm with the user that the parameter settings were changed, as shown in block 920. Also, the RF pulse generator module 106 can send back confirmation to the application that the parameter change has been successful, as shown in block 922, and the application may display the updated current program, as shown in block 924. If the parameter program change has failed, the RF pulse generator module 106 may perform a series of short vibrations to alert the user, and send an error message to the application, as shown in block 926, which receives the error and may display to the user, as shown in block 928.

Figure 10:
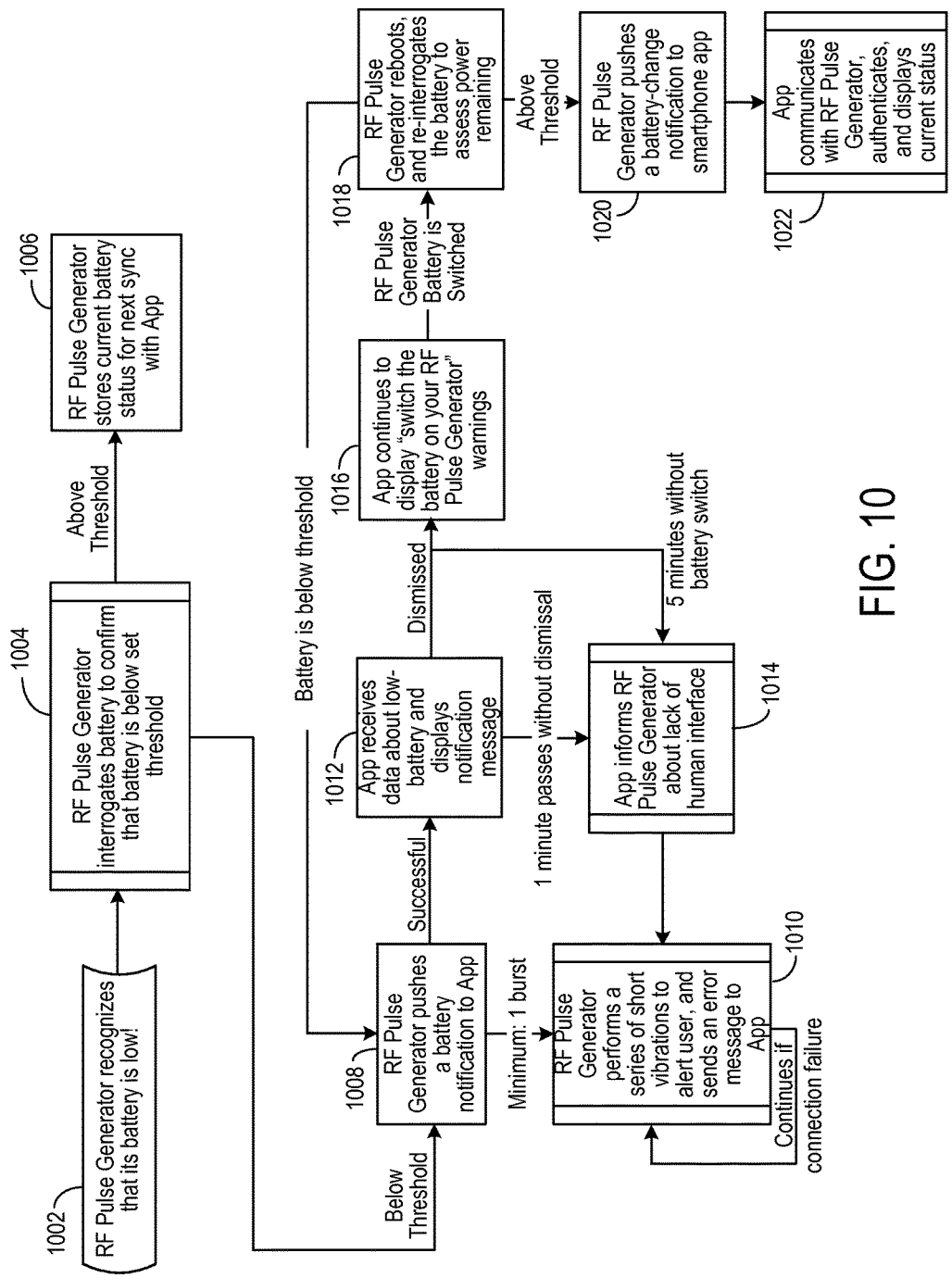
FIG. 10 is still another example flow chart of a process for a low battery state for the RF pulse generator module.

FIG. 10 is still another example flow chart of a process for a low battery state for the RF pulse generator module 106. In this implementation, the RF pulse generator module's remaining battery power level is recognized as low, as shown in block 1002. The RF pulse generator module 106 regularly interrogates the power supply battery subsystem 210 about the current power and the RF pulse generator microprocessor asks the battery if its remaining power is below threshold, as shown in block 1004. If the battery's remaining power is above the threshold, the RF pulse generator module 106 may store the current battery status to be sent to the application during the next sync, as shown in block 1006. If the battery's remaining power is below threshold the RF pulse generator module 106 may push a low-battery notification to the application, as shown in block 1008. The RF pulse generator module 106 may always perform one sequence of short vibrations to alert the user of an issue and send the application a notification, as shown in block 1010. If there continues to be no confirmation of the application receiving the notification then the RF pulse generator can continue to perform short vibration pulses to notify user, as shown in block 1010. If the application successfully receives the notification, it may display the notification and may need user acknowledgement, as shown in block 1012. If, for example, one minute passes without the notification message on the application being dismissed the application informs the RF pulse generator module 106 about lack of human acknowledgement, as shown in block 1014, and the RF pulse generator module 106 may begin to perform the vibration pulses to notify the user, as shown in block 1010. If the user dismisses the notification, the application may display a passive notification to switch the battery, as shown in block 1016. If a predetermined amount of time passes, such as five minutes for example, without the battery being switched, the application can inform the RF pulse generator module 106 of the lack of human acknowledgement, as shown in block 1014 and the RF pulse generator module 106 may perform vibrations, as shown in block 1010. If the RF pulse generator module battery is switched, the RF pulse generator module 106 reboots and interrogates the battery to assess power remaining, as shown in block 1018. If the battery's power remaining is below threshold, the cycle may begin again with the RF pulse generator module 106 pushing a notification to the application, as shown in block 1008. If the battery's power remaining is above threshold the RF pulse generator module 106 may push a successful battery-change notification to the application, as shown in block 1020. The application may then communicate with the RF pulse generator module 106 and displays current system status, as shown in block 1022.

Figure 11:
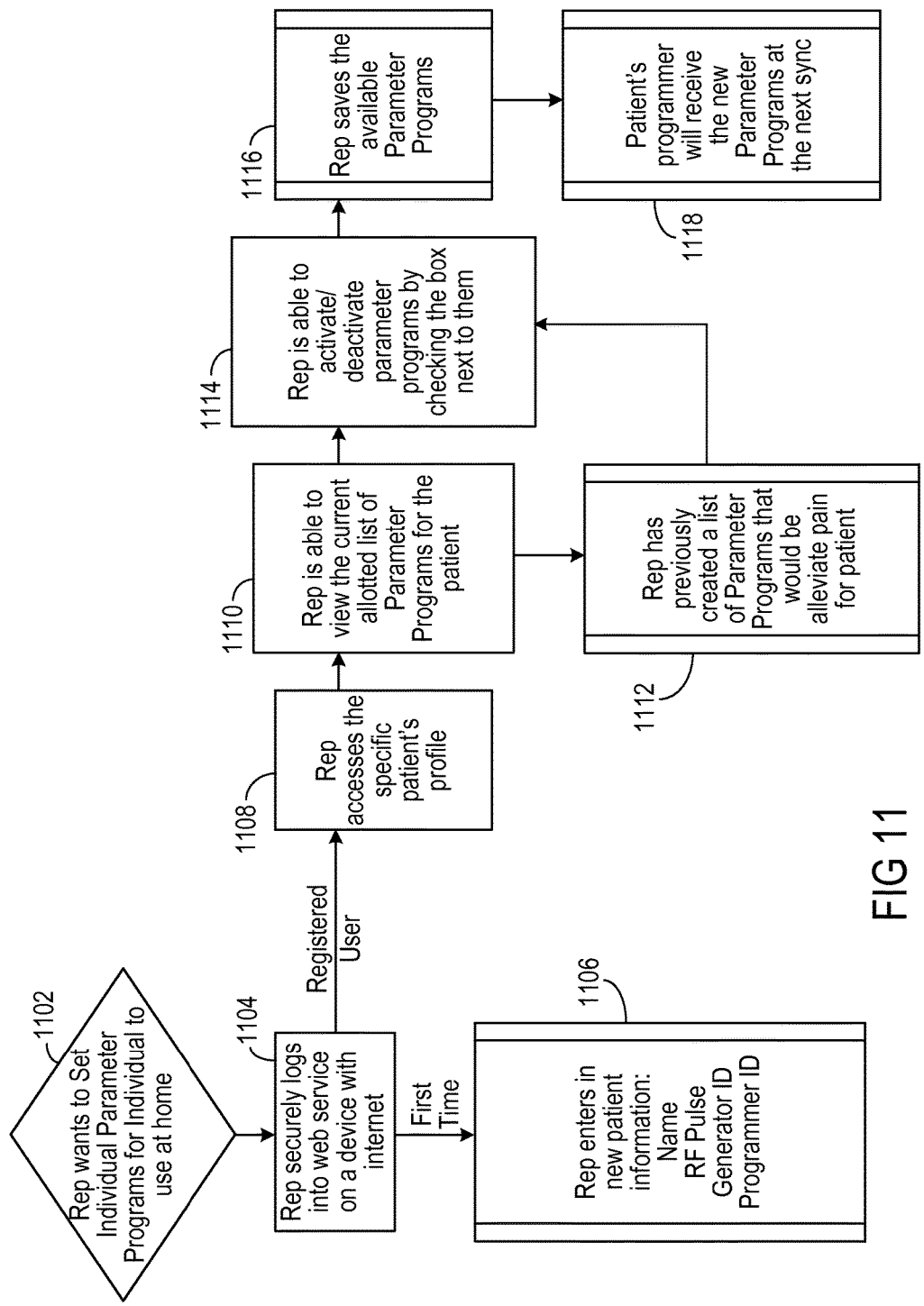
FIG. 11 is yet another example flow chart of a process for a Manufacturer's Representative to program the implanted wireless neural stimulator.

FIG. 11 is yet another example flow chart of a process for a Manufacturer's Representative to program the implanted wireless neural stimulator. In this implementation, a user wants the Manufacturer's Representative to set individual parameter programs from a remote location different than where the user is, for the user to use as needed, as shown in block 1102. The Manufacturer's Representative can gain access to the user's set parameter programs through a secure web based service. The Manufacturer's Representative can securely log into the manufacturer's web service on a device connected to the Internet, as shown in block 1104. If the Manufacturer's Representative is registering the user for the first time in their care they enter in the patient's basic information, the RF pulse generator's unique ID and the programming application's unique ID, as shown in block 1106. Once the Manufacturer's Representative's new or old user is already registered, the Manufacturer's Representative accesses the specific user's profile, as shown in block 1108. The Manufacturer's Representative is able to view the current allotted list of parameter programs for the specific user, as shown in block 1110. This list may contain previous active and retired parameter preset programs, as shown in block 1112. The Manufacturer's Representative is able to activate/deactivate preset parameter programs by checking the box next to the appropriate row in the table displayed, as shown in block 1114. The Manufacturer's Representative may then submit and save the allotted new preset parameter programs, as shown in block 1116. The user's programmer application may receive the new preset parameter programs at the next sync with the manufacturer's database.

Figure 12:
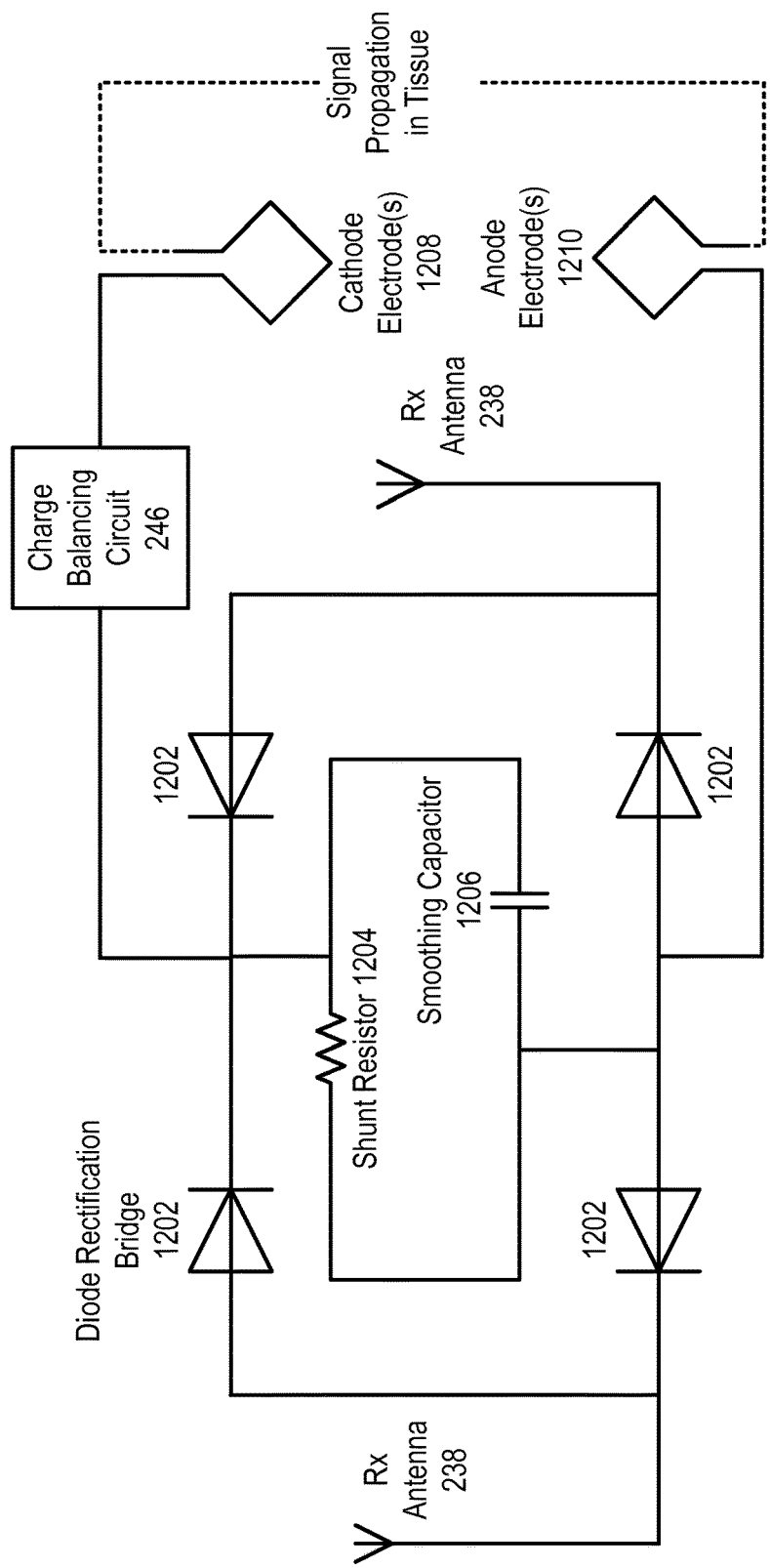
FIG. 12 is a circuit diagram showing an example of a wireless neural stimulator.

FIG. 12 is a circuit diagram showing an example of a wireless neural stimulator, such as stimulator 114. This example contains paired electrodes, comprising cathode electrode(s) 1208 and anode electrode(s) 1210, as shown. When energized, the charged electrodes create a volume conduction field of current density within the tissue. In this implementation, the wireless energy is received through a dipole antenna(s) 238. At least four diodes are connected together to form a full wave bridge rectifier 1202 attached to the dipole antenna(s) 238. Each diode, up to 100 micrometers in length, uses a junction potential to prevent the flow of negative electrical current, from cathode to anode, from passing through the device when said current does not exceed the reverse threshold. For neural stimulation via wireless power, transmitted through tissue, the natural inefficiency of the lossy material may lead to a low threshold voltage. In this implementation, a zero biased diode rectifier results in a low output impedance for the device. A resistor 1204 and a smoothing capacitor 1206 are placed across the output nodes of the bridge rectifier to discharge the electrodes to the ground of the bridge anode. The rectification bridge 1202 includes two branches of diode pairs connecting an anode-to-anode and then cathode to cathode. The electrodes 1208 and 1210 are connected to the output of the charge balancing circuit 246.

Figure 13:
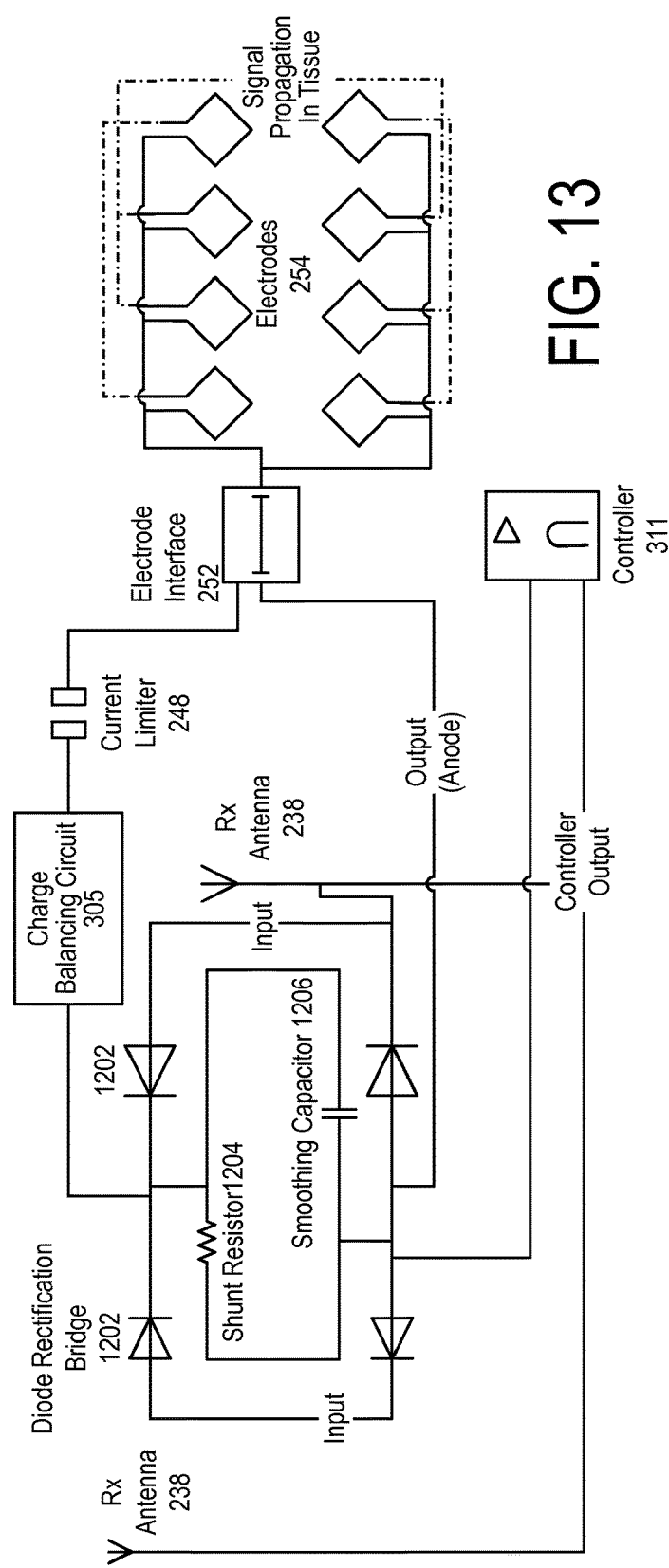
FIG. 13 is a circuit diagram of another example of a wireless neural stimulator.

FIG. 13 is a circuit diagram of another example of a wireless neural stimulator, such as stimulator 114. The example shown in FIG. 13 includes multiple electrode control and may employ full closed loop control. The stimulator includes an electrode array 254 in which the polarity of the electrodes can be assigned as cathodic or anodic, and for which the electrodes can be alternatively not powered with any energy. When energized, the charged electrodes create a volume conduction field of current density within the tissue. In this implementation, the wireless energy is received by the device through the dipole antenna(s) 238. The electrode array 254 is controlled through an on-board controller circuit 242 that sends the appropriate bit information to the electrode interface 252 in order to set the polarity of each electrode in the array, as well as power to each individual electrode. The lack of power to a specific electrode would set that electrode in a functional OFF position. In another implementation (not shown), the amount of current sent to each electrode is also controlled through the controller 242. The controller current, polarity and power state parameter data, shown as the controller output, is be sent back to the antenna(s) 238 for telemetry transmission back to the pulse generator module 106. The controller 242 also includes the functionality of current monitoring and sets a bit register counter so that the status of total current drawn can be sent back to the pulse generator module 106.

At least four diodes can be connected together to form a full wave bridge rectifier 302 attached to the dipole antenna(s) 238. Each diode, up to 100 micrometers in length, uses a junction potential to prevent the flow of negative electrical current, from cathode to anode, from passing through the device when said current does not exceed the reverse threshold. For neural stimulation via wireless power, transmitted through tissue, the natural inefficiency of the lossy material may lead to a low threshold voltage. In this implementation, a zero biased diode rectifier results in a low output impedance for the device. A resistor 1204 and a smoothing capacitor 1206 are placed across the output nodes of the bridge rectifier to discharge the electrodes to the ground of the bridge anode. The rectification bridge 1202 may include two branches of diode pairs connecting an anode-to-anode and then cathode to cathode. The electrode polarity outputs, both cathode 1208 and anode 1210 are connected to the outputs formed by the bridge connection. Charge balancing circuitry 246 and current limiting circuitry 248 are placed in series with the outputs.

Figure 14:
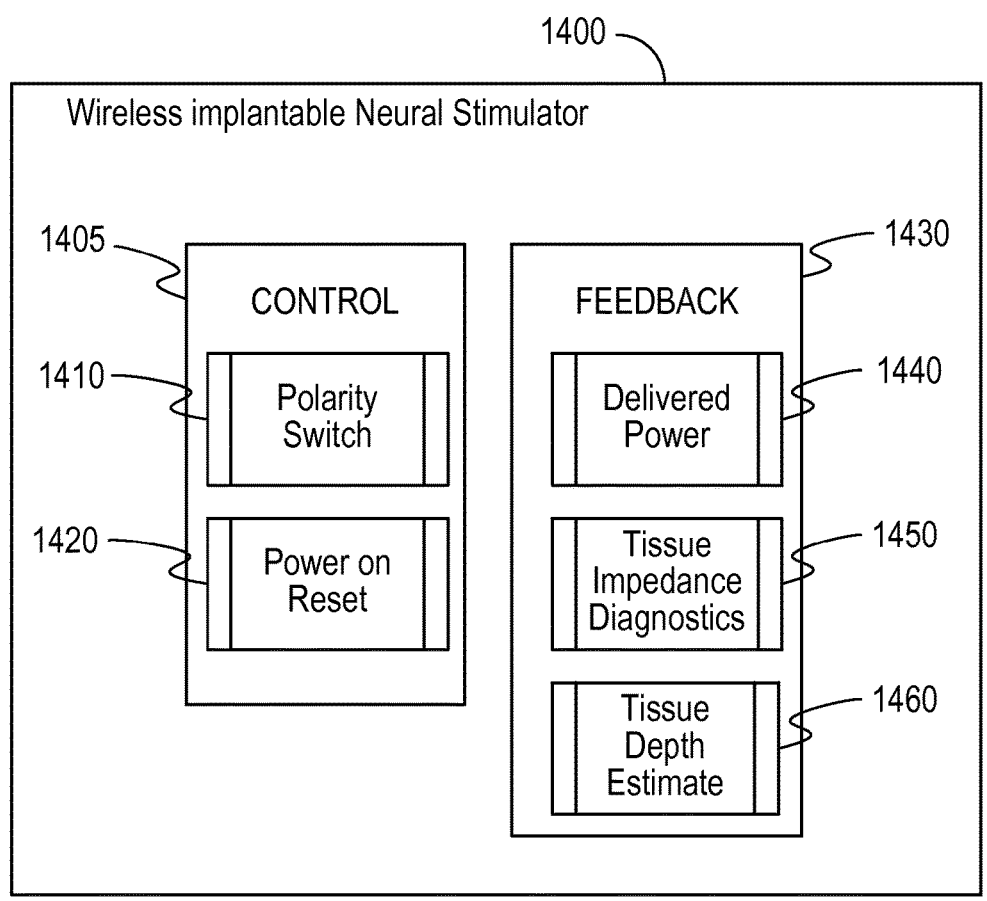
FIG. 14 is a block diagram showing an example of control and feedback functions of a wireless implantable neural stimulator.

FIG. 14 is a block diagram showing an example of control functions 1405 and feedback functions 1430 of a wireless implantable neural stimulator 1400, such as the ones described above or further below. An example implementation of the implantable neural stimulator 1400 may be implanted lead module 114, as discussed above in association with FIG. 2. Control functions 1405 include functions 1410 for polarity switching of the electrodes and functions 1420 for power-on reset.

Polarity switching functions 1410 may employ, for example, a polarity routing switch network to assign polarities to electrodes 254. The assignment of polarity to an electrode may, for instance, be one of: a cathode (negative polarity), an anode (positive polarity), or a neutral (off) polarity. The polarity assignment information for each of the electrodes 254 may be contained in the input signal received by wireless implantable neural stimulator 1400 through Rx antenna 238 from RF pulse generator module 106. Because a programmer module 102 may control RF pulse generator module 106, the polarity of electrodes 254 may be controlled remotely by a programmer through programmer module 102, as shown in FIGS. 2A and 2B.

Power-on reset functions 1420 may reset the polarity assignment of each electrode immediately on each power-on event. As will be described in further detail below, this reset operation may cause RF pulse generator module 106 to transmit the polarity assignment information to the wireless implantable neural stimulator 1400. Once the polarity assignment information is received by the wireless implantable neural stimulator 1400, the polarity assignment information may be stored in a register file, or other short term memory component. Thereafter the polarity assignment information may be used to configure the polarity assignment of each electrode. If the polarity assignment information transmitted in response to the reset encodes the same polarity state as before the power-on event, then the polarity state of each electrode can be maintained before and after each power-on event.

Feedback functions 1430 include functions 1440 for monitoring delivered power to electrodes 254 and functions 1450 for making impedance diagnosis of electrodes 254. For example, delivered power functions 1440 may provide data encoding the amount of power being delivered from electrodes 254 to the excitable tissue and tissue impedance diagnostic functions 1450 may provide data encoding the diagnostic information of tissue impedance. The tissue impedance is the electrical impedance of the tissue as seen between negative and positive electrodes when a stimulation current is being released between negative and positive electrodes.

Feedback functions 1430 may additionally include tissue depth estimate functions 1460 to provide data indicating the overall tissue depth that the input radio frequency (RF)

signal from the pulse generator module, such as, for example, RF pulse generator module 106, has penetrated before reaching the implanted antenna, such as, for example, RX antenna 238, within the wireless implantable neural stimulator 1400, such as, for example, implanted lead module 114. For instance, the tissue depth estimate may be provided by comparing the power of the received input signal to the power of the RF pulse transmitted by the RF pulse generator 106. The ratio of the power of the received input signal to the power of the RF pulse transmitted by the RF pulse generator 106 may indicate an attenuation caused by wave propagation through the tissue. For example, the second harmonic described below may be received by the RF pulse generator 106 and used with the power of the input signal sent by the RF pulse generator to determine the tissue depth. The attenuation may be used to infer the overall depth of wireless implantable neural stimulator 1400 underneath the skin.

The data from blocks 1440, 1450, and 1460 may be transmitted, for example, through Tx antenna 110 to RF pulse generator 106, as illustrated in FIGS. 1 and 2.

As discussed above in association with FIGS. 1, 2, 12, and 13, a wireless implantable neural stimulator 1400 may utilize rectification circuitry to convert the input signal (e.g., having a carrier frequency within a range from about 800 MHz to about 6 GHz) to a direct current (DC) power to drive the electrodes 254. Some implementations may provide the capability to regulate the DC power remotely. Some implementations may further provide different amounts of power to different electrodes, as discussed in further detail below.

Figure 15:
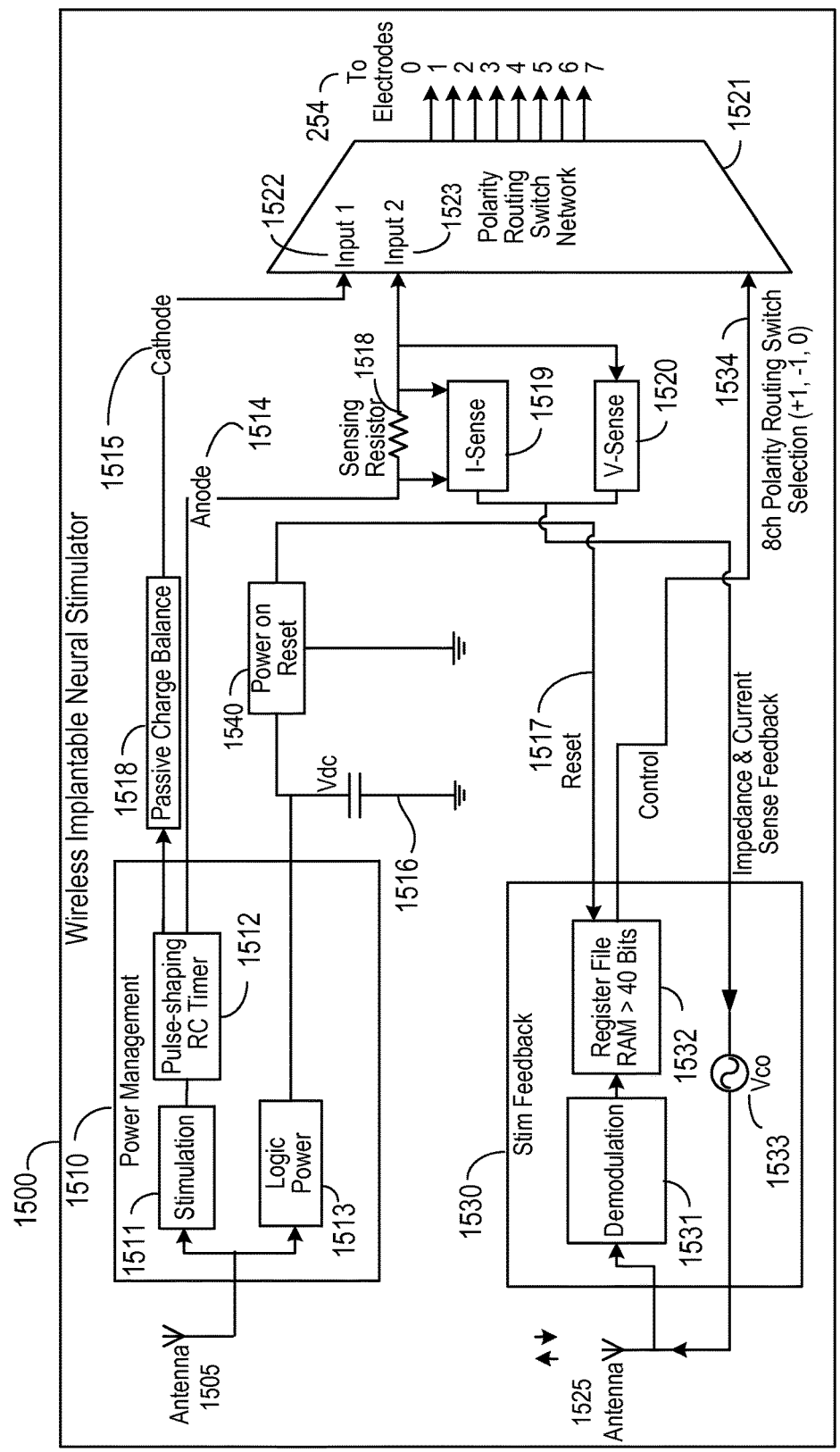
FIG. 15 is a schematic showing an example of a wireless implantable neural stimulator with components to implement control and feedback functions.

FIG. 15 is a schematic showing an example of a wireless implantable neural stimulator 1500 with components to implement control and feedback functions as discussed above in association with FIG. 14. An RX antenna 1505 receives the input signal. The RX antenna 1505 may be embedded as a dipole, microstrip, folded dipole or other antenna configuration other than a coiled configuration, as described above. The input signal has a carrier frequency in the GHz range and contains electrical energy for powering the wireless implantable neural stimulator 1500 and for providing stimulation pulses to electrodes 254. Once received by the antenna 1505, the input signal is routed to power management circuitry 1510. Power management circuitry 1510 is configured to rectify the input signal and convert it to a DC power source. For example, the power management circuitry 1510 may include a diode rectification bridge such as the diode rectification bridge 1202 illustrated in FIG. 12. The DC power source provides power to stimulation circuitry 1511 and logic power circuitry 1513. The rectification may utilize one or more full wave diode bridge rectifiers within the power management circuitry 1510. In one implementation, a resistor can be placed across the output nodes of the bridge rectifier to discharge the electrodes to the ground of the bridge anode, as illustrated by the shunt register 1204 in FIG. 12.

Figure 16:
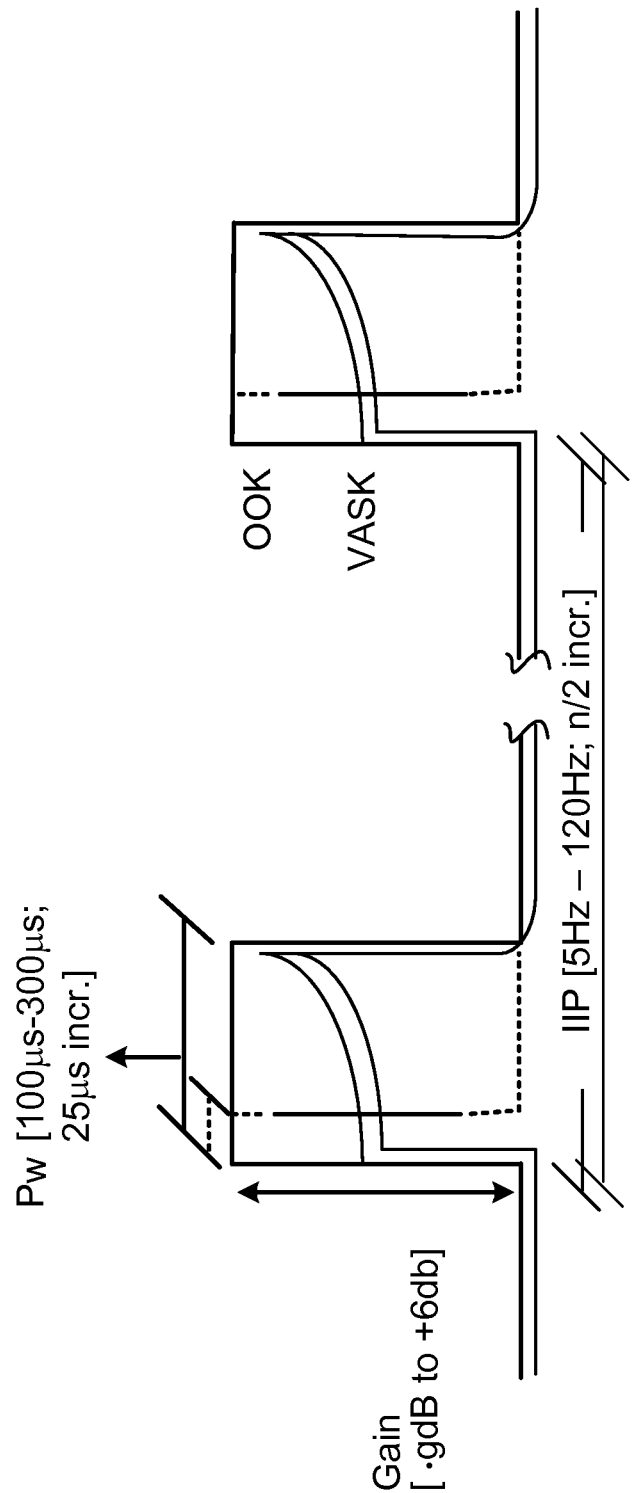
FIG. 16 shows an example of a pulse waveform seen at the power management circuitry of a wireless implantable neural stimulator.

FIG. 16 shows an example pulse waveform generated by the MFS sent to the power management circuitry 1510 of the wireless implantable neural stimulator 1500. This can be a typical pulse waveform generated by the RF pulse generator module 106 and then passed on the carrier frequency. The pulse amplitude is ramped over the pulse width (duration) from a value ranging from −9 dB to +6 dB. In certain implementations, the ramp start and end power level can be set to any range from 0 to 60 dB. The gain control is adjustable and can be an input parameter from RF pulse generator module 106 to the stimulation power management circuitry 1510. The pulse width, Pw, can range from 100 to 300 microseconds (µs) in some implementations, as shown in FIG. 16. In other implementations not shown, the pulse width can be between about 5 microseconds (5 us) and about 10 milliseconds (10 ms). The pulse frequency (rate) can range from about 5 Hz to 120 Hz as shown. In some implementations not shown, the pulse frequency can be below 5 Hz, and as high as about 10,000 Hz.

Returning to FIG. 15, based on the received waveform, stimulation circuitry 1511 creates the stimulation waveform to be sent to the electrodes 254 to stimulate excitable tissues, as discussed above. In some implementations, stimulation circuitry 1511 may route the waveform to pulse-shaping resistor-capacitor (RC) timer 1512 to shape each travelling pulse waveform. An example RC-timer can be the shunt resistor 1204 and smoothing resistor 1206, as illustrated in FIG. 12 and as discussed above. The pulse-shaping RC timer 1512 can also be used to, but is not limited to, inverting the pulse to create a pre-anodic dip or provide a slow ramping in waveform.

Once the waveform has been shaped, the cathodic energy—energy being transmitted over the cathodic branch 1515 of the polarity routing switch network 1523—is routed through the passive charge balancing circuitry 1518 to prevent the build-up of noxious chemicals at the electrodes 254, as discussed above. Cathodic energy is then routed to input 1, block 1522, of polarity routing switch network 1521. Anodic energy—energy being transmitted over the anodic branch 1514 of the polarity routing switch network 1523—is routed to input 2, block 1523, of polarity routing switch network 1521. Thereafter, the polarity routing switch network 1521 delivers the stimulation energy in the form of cathodic energy, anodic energy, or no energy, to the each of the electrodes 254, depending on the respective polarity assignment, which is controlled based on a set of bits stored in the register file 1532. The bits stored in the register file 1532 are output to a selection input 1534 of the polarity routing switch network 1523, which causes input 1 or input 2 to be routed to the electrodes as appropriate.

Figure 17:
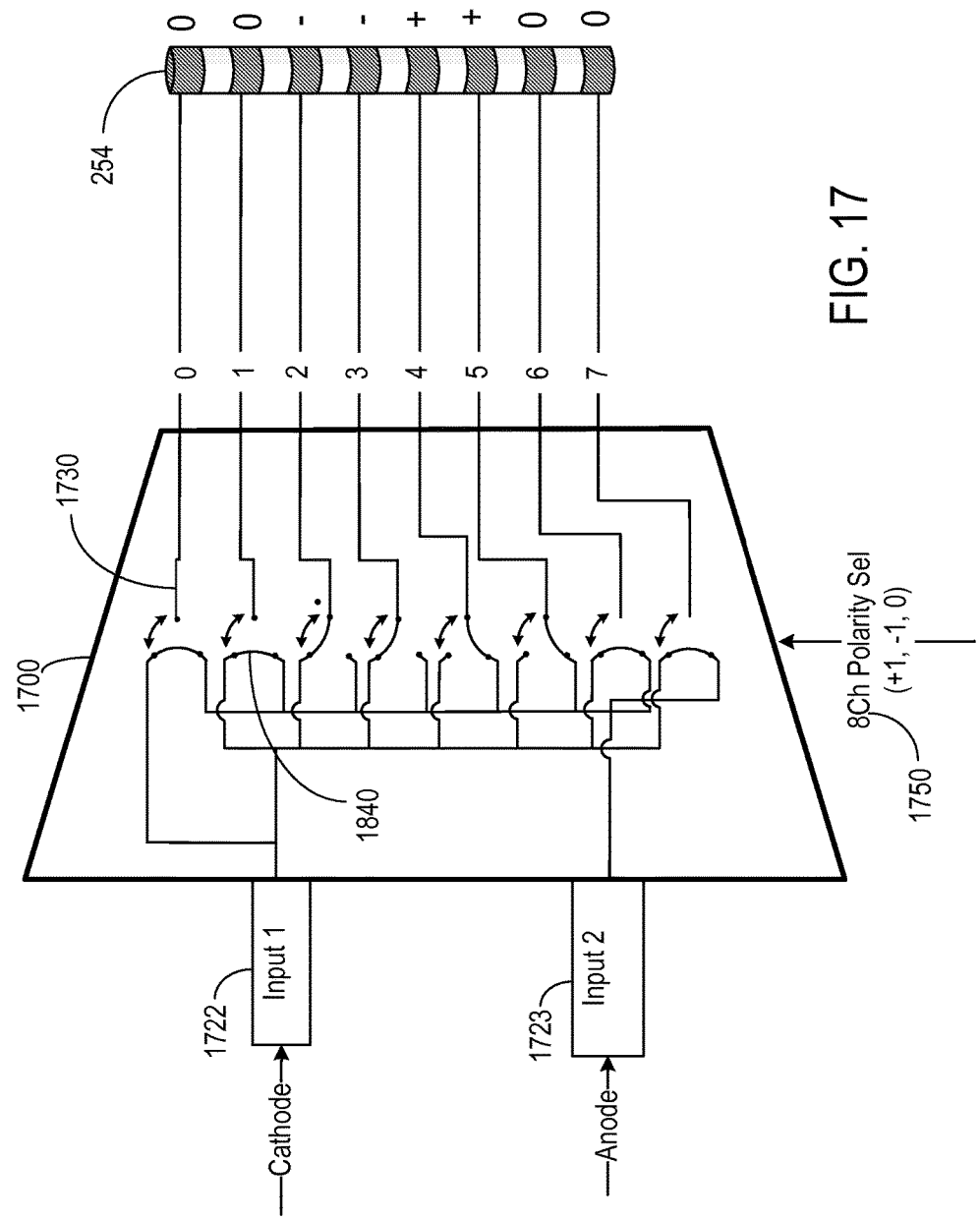
FIG. 17 is a schematic of an example of a polarity routing switch network.

Turning momentarily to FIG. 17, a schematic of an example of a polarity routing switch network 1700 is shown. As discussed above, the cathodic (−) energy and the anodic energy are received at input 1 (block 1522) and input 2 (block 1523), respectively. Polarity routing switch network 1700 has one of its outputs coupled to an electrode of electrodes 254 which can include as few as two electrodes, or as many as sixteen electrodes. Eight electrodes are shown in this implementation as an example.

Polarity routing switch network 1700 is configured to either individually connect each output to one of input 1 or input 2, or disconnect the output from either of the inputs. This selects the polarity for each individual electrode of electrodes 254 as one of: neutral (off), cathode (negative), or anode (positive). Each output is coupled to a corresponding three-state switch 1730 for setting the connection state of the output. Each three-state switch is controlled by one or more of the bits from the selection input 1750. In some implementations, selection input 1750 may allocate more than one bits to each three-state switch. For example, two bits may encode the three-state information. Thus, the state of each output of polarity routing switch device 1700 can be controlled by information encoding the bits stored in the register 1532, which may be set by polarity assignment information received from the remote RF pulse generator module 106, as described further below.

Returning to FIG. 15, power and impedance sensing circuitry may be used to determine the power delivered to the tissue and the impedance of the tissue. For example, a sensing resistor 1518 may be placed in serial connection with the anodic branch 1514. Current sensing circuit 1519 senses the current across the resistor 1518 and voltage sensing circuit 1520 senses the voltage across the resistor. The measured current and voltage may correspond to the actual current and voltage applied by the electrodes to the tissue.

As described below, the measured current and voltage may be provided as feedback information to RF pulse generator module 106. The power delivered to the tissue may be determined by integrating the product of the measured current and voltage over the duration of the waveform being delivered to electrodes 254. Similarly, the impedance of the tissue may be determined based on the measured voltage being applied to the electrodes and the current being applied to the tissue. Alternative circuitry (not shown) may also be used in lieu of the sensing resistor 1518, depending on implementation of the feature and whether both impedance and power feedback are measured individually, or combined.

The measurements from the current sensing circuitry 1519 and the voltage sensing circuitry 1520 may be routed to a voltage controlled oscillator (VCO) 1533 or equivalent circuitry capable of converting from an analog signal source to a carrier signal for modulation. VCO 1533 can generate a digital signal with a carrier frequency. The carrier frequency may vary based on analog measurements such as, for example, a voltage, a differential of a voltage and a power, etc. VCO 1533 may also use amplitude modulation or phase shift keying to modulate the feedback information at the carrier frequency. The VCO or the equivalent circuit may be generally referred to as an analog controlled carrier modulator. The modulator may transmit information encoding the sensed current or voltage back to RF pulse generator 106.

Antenna 1525 may transmit the modulated signal, for example, in the GHz frequency range, back to the RF pulse generator module 106. In some embodiments, antennas 1505 and 1525 may be the same physical antenna. In other embodiments, antennas 1505 and 1525 may be separate physical antennas. In the embodiments of separate antennas, antenna 1525 may operate at a resonance frequency that is higher than the resonance frequency of antenna 1505 to send stimulation feedback to RF pulse generator module 106. In some embodiments. antenna 1525 may also operate at the higher resonance frequency to receive data encoding the polarity assignment information from RF pulse generator module 106.

Antenna 1525 may be a telemetry antenna 1525 which may route received data, such as polarity assignment information, to the stimulation feedback circuit 1530. The encoded polarity assignment information may be on a band in the GHz range. The received data may be demodulated by demodulation circuitry 1531 and then stored in the register file 1532. The register file 1532 may be a volatile memory. Register file 1532 may be an 8-channel memory bank that can store, for example, several bits of data for each channel to be assigned a polarity. Some embodiments may have no register file, while some embodiments may have a register file up to 64 bits in size. The information encoded by these bits may be sent as the polarity selection signal to polarity routing switch network 1521, as indicated by arrow 1534. The bits may encode the polarity assignment for each output of the polarity routing switch network as one of: +(positive), − (negative), or 0 (neutral). Each output connects to one electrode and the channel setting determines whether the electrode will be set as an anode (positive), cathode (negative), or off (neutral).

Returning to power management circuitry 1510, in some embodiments, approximately 90% of the energy received is routed to the stimulation circuitry 1511 and less than 10% of the energy received is routed to the logic power circuitry 1513. Logic power circuitry 1513 may power the control components for polarity and telemetry. In some implementations, the power circuitry 1513, however, does not provide the actual power to the electrodes for stimulating the tissues. In certain embodiments, the energy leaving the logic power circuitry 1513 is sent to a capacitor circuit 1516 to store a certain amount of readily available energy. The voltage of the stored charge in the capacitor circuit 1516 may be denoted as Vdc. Subsequently, this stored energy is used to power a power-on reset circuit 1516 configured to send a reset signal on a power-on event. If the wireless implantable neural stimulator 1500 loses power for a certain period of time, for example, in the range from about 1 millisecond to over 10 milliseconds, the contents in the register file 1532 and polarity setting on polarity routing switch network 1521 may be zeroed. The wireless implantable neural stimulator 1500 may lose power, for example, when it becomes less aligned with RF pulse generator module 106. Using this stored energy, power-on reset circuit 1540 may provide a reset signal as indicated by arrow 1517. This reset signal may cause stimulation feedback circuit 1530 to notify RF pulse generator module 106 of the loss of power. For example, stimulation feedback circuit 1530 may transmit a telemetry feedback signal to RF pulse generator module 106 as a status notification of the power outage. This telemetry feedback signal may be transmitted in response to the reset signal and immediately after power is back on neural stimulator 1500. RF pulse generator module 106 may then transmit one or more telemetry packets to implantable wireless neutral stimulator. The telemetry packets contain polarity assignment information, which may be saved to register file 1532 and may be sent to polarity routing switch network 1521. Thus, polarity assignment information in register file 1532 may be recovered from telemetry packets transmitted by RF pulse generator module 106 and the polarity assignment for each output of polarity routing switch network 1521 may be updated accordingly based on the polarity assignment information.

Figure 18A:
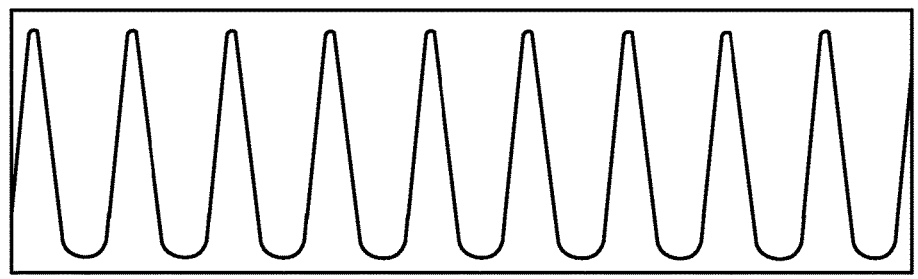
FIGS. 18A and 18B, respectively show an example of a waveform generated by a rectifying circuit of a wireless neural stimulator and the corresponding spectrum.
Figure 18B:
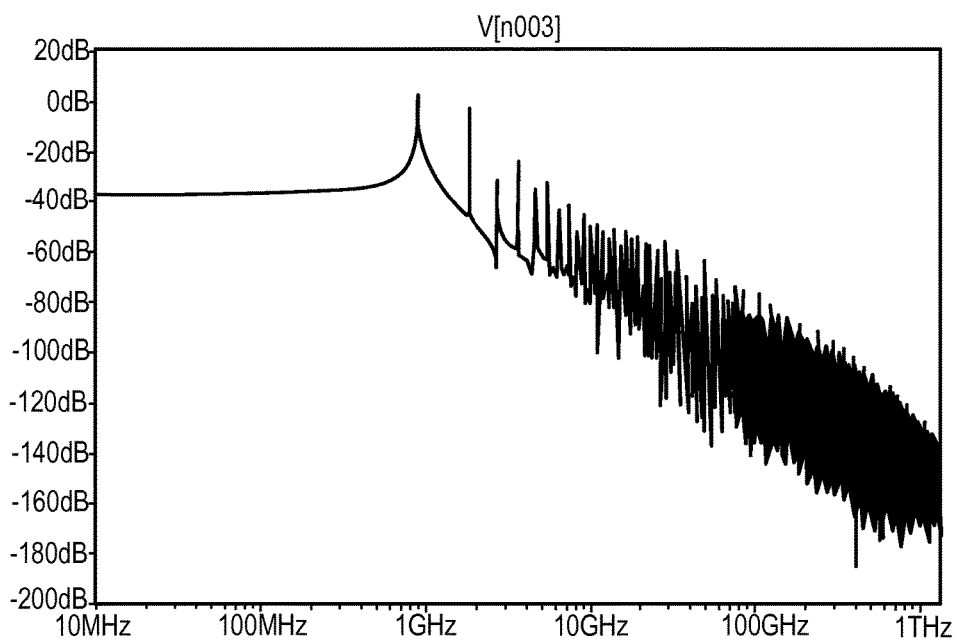

The telemetry antenna 1525 may transmit the telemetry feedback signal back to RF pulse generator module 106 at a frequency higher than the characteristic frequency of an RX antenna 1505. In one implementation, the telemetry antenna 1525 can have a heightened resonance frequency that is the second harmonic of the characteristic frequency of RX antenna 1505. For example, the second harmonic may be utilized to transmit power feedback information regarding an estimate of the amount of power being received by the electrodes. The feedback information may then be used by the RF pulse generator in determining any adjustment of the power level to be transmitted by the RF pulse generator 106. In a similar manner, the second harmonic energy can be used to detect the tissue depth. The second harmonic transmission can be detected by an external antenna, for example, on RF pulse generator module 106 that is tuned to the second harmonic. As a general matter, power management circuitry 1510 may contain rectifying circuits that are non-linear device capable of generating harmonic energies from input signal. Harvesting such harmonic energy for transmitting telemetry feedback signal could improve the efficiency of wireless implantable neural stimulator 1500. FIGS. 18A and 18B and the following discussion demonstrate the feasibility of utilizing the second harmonic to transmit telemetry signal to RF pulse generator module 106.

FIGS. 18A and 18BB respectively show an example full-wave rectified sine wave and the corresponding spectrum. In particular, a full-wave rectified 915 MHz sine wave is being analyzed. In this example, the second harmonic of a 915 MHz sine wave is an 1830 MHz output harmonic. This harmonic wave may be attenuated by the amount of tissue that the harmonic wave needs to pass through before reaching the external harmonic receiver antenna. In general, an estimation of the power levels during the propagation of the harmonic wave can reveal the feasibility of the approach. The estimation may consider the power of received input signal at the receiving antenna (e.g., at antenna 1505 and at 915 MHz), the power of the second harmonic radiated from the rectified 915 MHz waveform, the amount of attenuation for the second harmonic wave to propagate through the tissue medium, and an estimation of the coupling efficiency for the harmonic antenna. The average power transmitted in Watts can be estimated by Equation 1:

$$Pt = Pk\, DuC$$

$$P_r = (P_t/A_{ant})(1-\{\Gamma\}^2)L\lambda^2 G_r \eta/4\pi \quad (1)$$

Table 1 below tabulates the denotations of each symbol and the corresponding value used in the estimation.

TABLE 1

Parameters utilized in development of the Received Power equation.

| Parameter | Value |
| --- | --- |
| $P_k$ (PeakPower)(W) | 1.576 |
| DuC (Duty Cycle) | 0.5 |
| $P_t$ (Average power transmitted) | 1.576 |
| $A_{ant}$ (Antenna aperture area) (m$^2$) | 0.01 |
| $\Gamma$ (Voltage reflection coefficient) | 0.5 |
| $1 - \{\Gamma\}^2$ (Transmission Loss) | 0.75 |
| L (Loss through tissue) (dB) | 10 |
| $\lambda$ (Wavelength) (m) | 0.689 |
| $G_r$ (Gain of implanted receiving antenna) | 2 |
| $\eta$ (RF-DC efficiency) | 0.5 |
| $R_{torso}$ (Equivalent Tissue Resistance) (Ohm) | 500 |

In estimating L, the loss due to the attenuation in the tissue, attenuations from the fundamental (for the forward path to the implanted lead module 114) and second harmonics (for the reverse path from the implanted lead module 113) may be considered. The plane wave attenuation is given by the following equation (2) and Table 2:

$$\alpha = \frac{2\pi f}{c}\left(\frac{\varepsilon_r}{2}\right)^{0.5}\left(-1 + \left(1+\left(\frac{\sigma}{\omega\varepsilon_0\varepsilon_r}\right)^2\right)^{0.5}\right)^{0.5} \quad (2)$$

where $f$ = frequency $c$ = speed of light in vaccum $\varepsilon_r$ = relative dielectric constant $\sigma$ = conductivity $\varepsilon_0$ = permittivity of vacuum

TABLE 2

Estimated output power loss for 915 MHz and 1830 MHz harmonic at 1 cm depth.

| Freq(MHz) | r | S/m | neper/m | Power loss |
| --- | --- | --- | --- | --- |
| 0.915e9 | 41.329 | 0.87169 | 25.030 | 0.606 |
| 1.83e9 | 38.823 | 1.1965 | 35.773 | 0.489 |

The worst-case assumption for coupling of the harmonics wave to the external receive antenna is that the power radiated at the harmonic frequency by the implanted telemetry antenna (e.g., telemetry antenna 1625) is completely absorbed by external receive antenna. This worse-case scenario can be modeled by the following equation (3) and Table 3:

$$P_{nr} = P_t L_n L_{na} \quad (3)$$

where n=nth Harmonic $P_{nr}$=nth Harmonic Antenna Received Power (W)

$P_t$=Total Received power of Implant (W)

$L_n$=Power of nth Harmonic of ImplantPower (W)

$L_{na}$=Attenuation Loss Factor

TABLE 3

Output total power and received harmonic power for the 2$^{nd}$ harmonic.

| $P_t$(W) | $L_n$ | $L_{na}$ | $P_{nr}$(W) | dBm |
| --- | --- | --- | --- | --- |
| 0.356 | .2421 | 0.489 | 0.0422 | 16.3 |

In sum, the reduction of power levels has been estimated to be about 10 dB utilizing these developed equations. This includes the attenuation of a 915 MHz plane wave that propagates through tissue depths from 1 cm to 6 cm. The average received power, Pr, at 915 MHz is 0.356 W. The power in the second harmonic (1830 MHz) is about −6.16 dB, as obtained from a SPICE simulation using a full wave rectified 915 MHz sine wave. The estimate of 10 dB means a reduction of a factor of 10, which is acceptable for field operations. Thus, the feasibility of utilizing the second harmonic frequency to transmit the telemetry feedback signal back to the RF pulse generator module 106 has been demonstrated.

Figure 19:
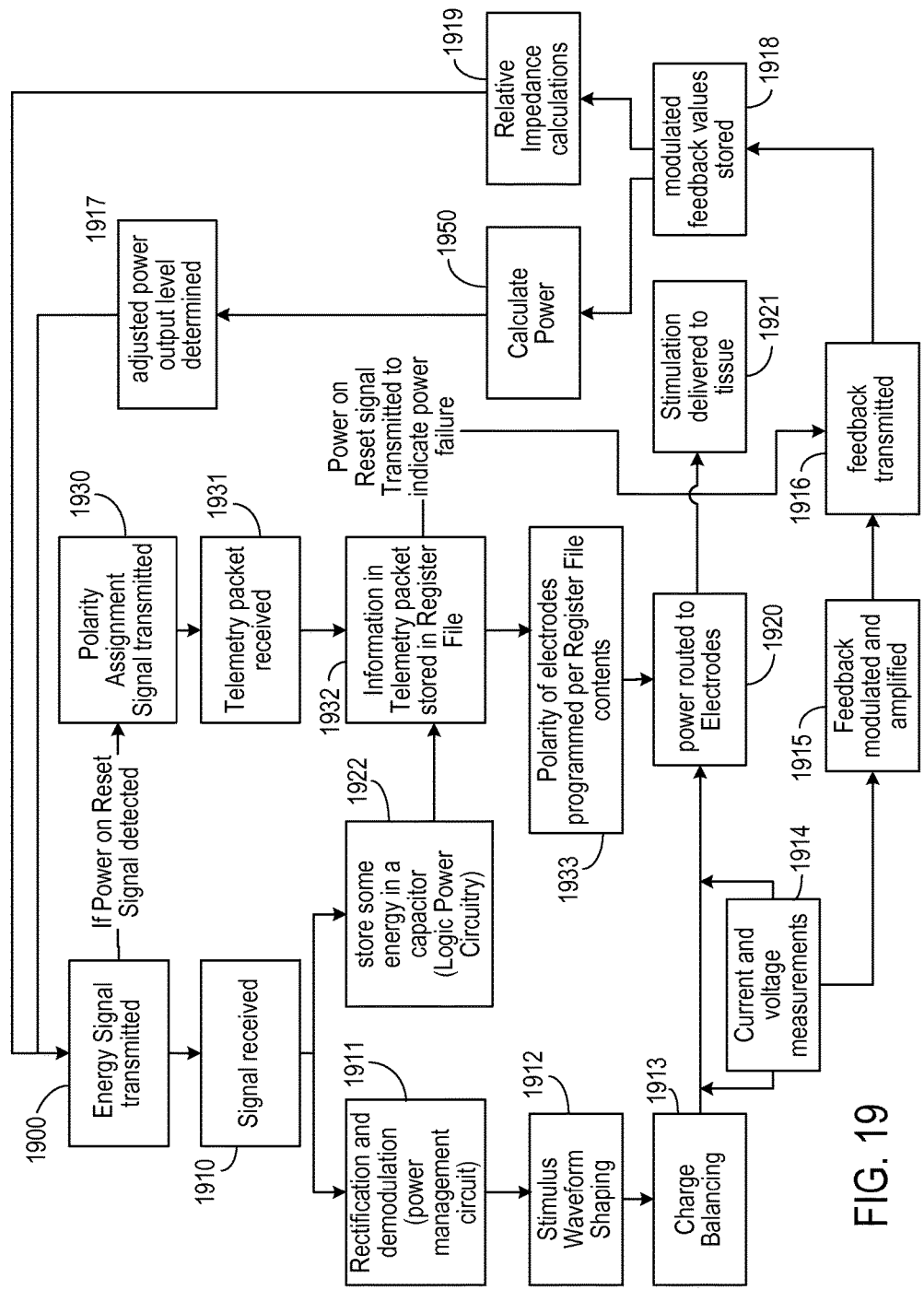
FIG. 19 is a flow chart illustrating an example of the operations of control and feedback functions of a wireless implantable neural stimulator.

FIG. 19 is a flow chart illustrating an example of operations of control and feedback functions of the neural stimulator. The operations are described with respect to the wireless implantable neural stimulator 1500, although the operations may be performed by other variations of a wireless implantable neural stimulator, such as the ones described above.

RF pulse generator module 106 transmits one or more signals containing electrical energy (1900). RF pulse generator module 106 may also be known as a microwave field stimulator (MFS) in some implementations. The signal may be modulated at a microwave frequency band, for example, from about 800 MHz to about 6 GHz.

The input signal containing electrical energy is received by RX antenna 1505 of the neural stimulator 1500 (1910). As discussed above, RX antenna 1505 may be embedded as a dipole, microstrip, folded dipole or other antenna configuration other than a coiled configuration.

The input signal is rectified and demodulated by the power management circuitry 1510, as shown by block 1911. Some implementations may provide waveform shaping and, in this case, the rectified and demodulated signal is passed to pulse shaping RC timer (1912). Charge balancing may be performed by charge balancing circuit 1518 to provide a charged balanced waveform (1913). Thereafter, the shaped and charge balanced pulses are routed to electrodes 254 (1920), which deliver the stimulation to the excitable tissue (1921).

In the meantime, the current and voltage being delivered to the tissue is measured using the current sensor 1519 and voltage sensor 1520 (1914). These measurements are modulated and amplified (1915) and transmitted to the RF pulse generator module 106 from telemetry antenna 1525 (1916). In some embodiments, the telemetry antenna 1525 and RX antenna 1505 may utilize the same physical antenna embedded within the neural stimulator 1500. The RF pulse generator module 106 may use the measured current and voltage to determine the power delivered to the tissue, as well as the impedance of the tissue.

For example, the RF pulse generator module 106 may store the received feedback information such as the information encoding the current and voltage. The feedback information may be stored, for instance, as a present value in a hardware memory on RF pulse generator module 106. Based on the feedback information, RF pulse generator module 106 may calculate the impedance value of the tissue based on the current and voltage delivered to the tissue.

In addition, RF pulse generator module 106 may calculate the power delivered to the tissue based on the stored current and voltage (1950). The RF pulse generator module 106 can then determine whether power level should be adjusted by comparing the calculated power to the desired power stored, for example, in a lookup table stored on the RF pulse generator module 106 (1917). For example, the look-up table may tabulate the optimal amount of power that should be delivered to the tissue for the position of the receive antenna 1505 on neural stimulator 1500 relative to the position of the transmit antenna on RF pulse generator module 106. This relative position may be determined based on the feedback information. The power measurements in the feedback information may then be correlated to the optimal value to determine if a power level adjustment should be made to increase or decrease the amplitude of stimulation of the delivered power to the electrodes. The power level adjustment information may then enable the RF pulse generator module 106 to adjust parameters of transmission so that the adjusted power is provided to the RX antenna 1505.

In addition to the input signal containing electrical energy for stimulation, the RF pulse generator module 106 may send an input signal that contains telemetry data such as polarity assignment information (1930). For instance, upon power on, the RF pulse generator module 106 may transmit data encoding the last electrode polarity settings for each electrode before RF pulse generator module 106 was powered off. This data may be sent to telemetry antenna 1525 as a digital data stream embedded on the carrier waveform. In some implementations, the data stream may include telemetry packets. The telemetry packets are received from the RF pulse generator module 106 and subsequently demodulated (1931) by demodulation circuit 1531. The polarity setting information in the telemetry packets is stored in the register file 1532 (1932). The polarity of each electrode of electrodes 254 is programmed according to the polarity setting information stored in the register file 1532 (1933). For example, the polarity of each electrode may be set as one of: anode (positive), cathode (negative), or neutral (off).

As discussed above, upon a power-on reset, the polarity setting information is resent from the RF pulse generator module 106 to be stored in the register file 1532 (1932). This is indicated by the arrow 1932 to 1916. The information of polarity setting stored in the register file 1532 may then be used to program the polarity of each electrode of electrodes 254 (1933). The feature allows for re-programming of a passive device remotely from the RF pulse generator module 106 at the start of each powered session, thus obviating the need of maintaining CMOS memory within the neural stimulator 1500.

Figure 20A:
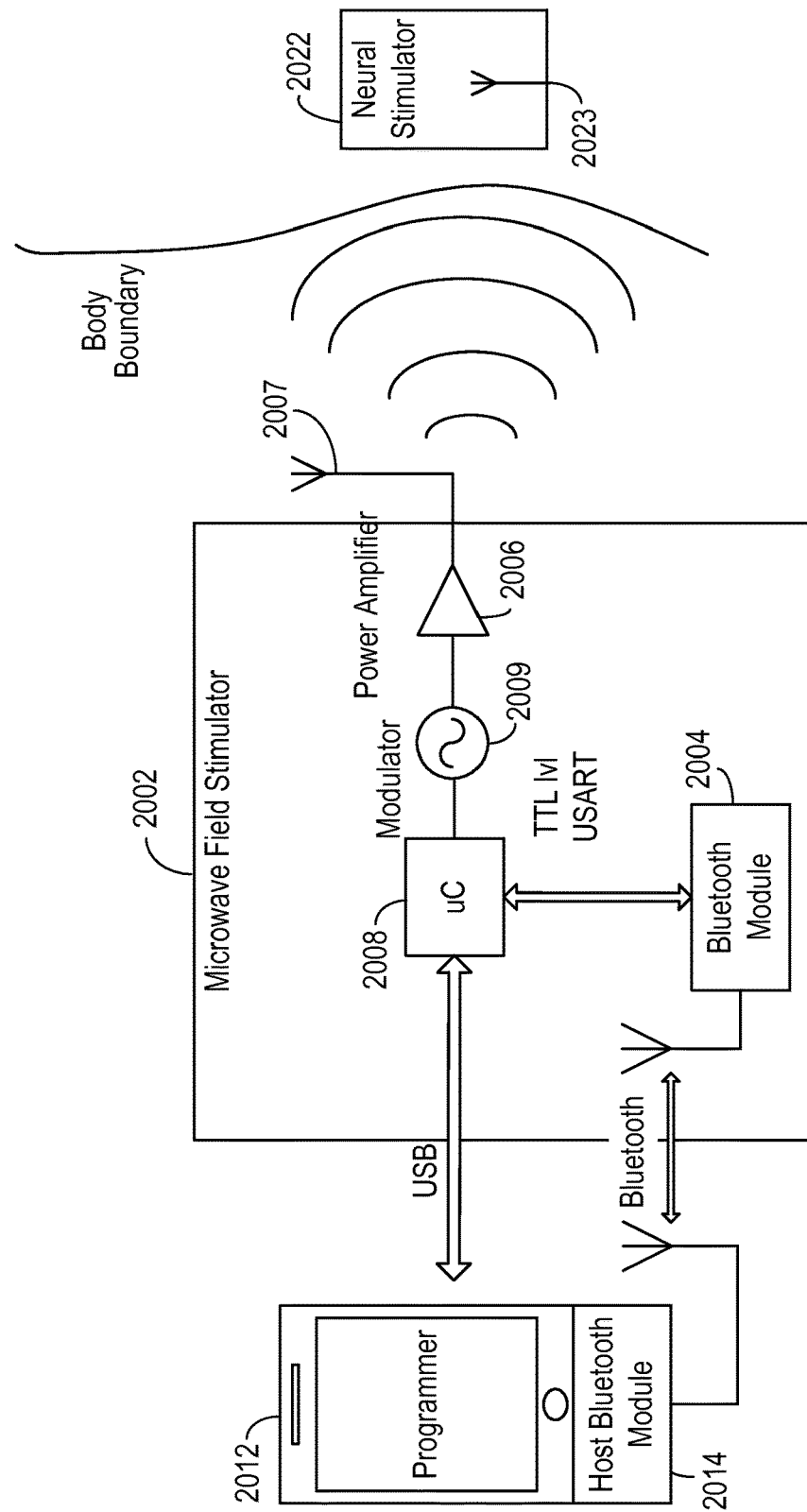
FIG. 20A is a diagram of an example microwave field stimulator (MFS) operating along with an implantable stimulation device.

FIG. 20A is a diagram of an example implementation of a microwave field stimulator (MFS) 2002 as part of a stimulation system utilizing an implantable, passive device 2022. In this example, the MFS 2002 is external to a patient's body and may be placed within in close proximity, for example, within 3 feet, to an implantable, passive 2022. The RF pulse generator module 106 may be one example implementation of MFS 2002. MFS 2002 may be generally known as a controller module. The implanted lead module 114 may be one example of an implantable, passive simulation device 2022. The implantable, passive simulation device 2022 is a passive device. The implantable, passive stimulation device does not have its own independent power source, rather it receives power for its operation from transmission signals emitted from a TX antenna powered by the MFS 2002, as discussed above.

In certain embodiments, the MFS 2002 may communicate with a programmer 2012. The programmer 2012 may be a mobile computing device, such as, for example, a laptop, a smart phone, a tablet, etc. The communication may be wired, using for example, a USB or firewire cable. The communication may also be wireless, utilizing for example, a bluetooth protocol implemented by a transmitting blue tooth module 2004 which communicates with the host bluetooth module 2014 within the programmer 2012. A user, such as a patient, company representative, or a doctor may use the programmer 2012 to send stimulation information to the MFS 2012, which stores the stimulation information. The stimulation information may include, for example, the polarity of the electrodes in the implantable, passive stimulation device 2022 and/or the parameters defining the stimulation waveform.

The MFS 2002 may additionally communicate with implantable, passive stimulation device 2022 by transmitting a transmission signal through a TX antenna 2007 coupled to an amplifier 2006. The transmission signal may propagate through skin and underlying tissues to arrive at the RX antenna 2023 of the implantable, passive stimulation device 2022. As discussed in further detail below, this transmission signal may encode polarity assignments for the electrodes in the stimulation device 2022 and include the stimulation waveform. In some implementations, the implantable, passive stimulation device 2022 may transmit a telemetry feedback signal back to MFS 2002.

The MFS 2002 may include a microcontroller 2008 configured to manage the communication with a programmer 2012 and generate an output signal based on the stimulation information sent from the programmer. The output signal may be used by the modulator 2009 to modulate a RF carrier signal to generate the transmission signal. The frequency of the carrier signal may be in the microwave range, for example, from about 300 MHz to about 8 GHz. This frequency may be known as the stimulus carrier frequency. The modulated RF carrier signal may be amplified by an amplifier 2006 to provide the transmission signal for transmission to the implantable, passive stimulation device 2022 through a TX antenna 2007.

Figure 20B:
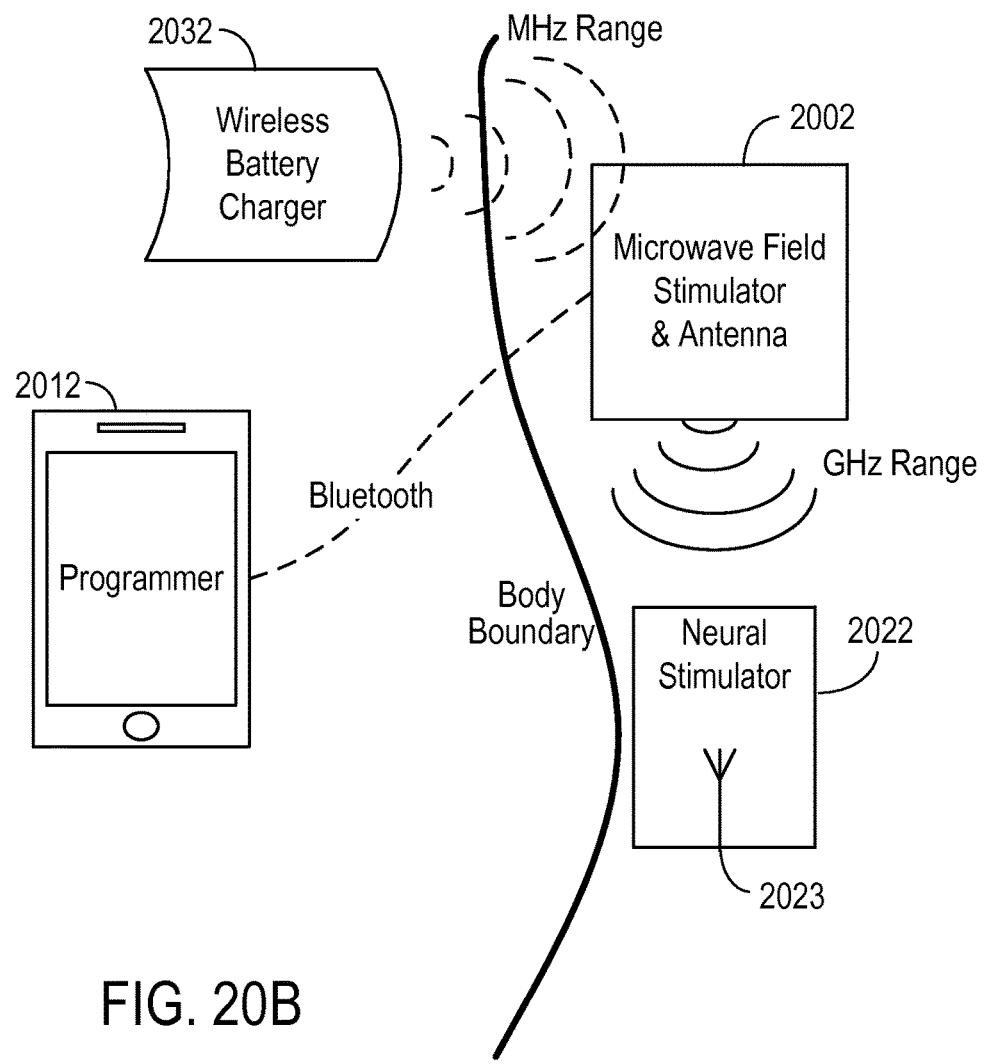
FIG. 20B is a diagram of another example microwave field stimulator (MFS) operating along with an implantable stimulation device.

FIG. 20B is a diagram of another example of an implementation of a microwave field stimulator 2002 as part of a stimulation system utilizing an implantable, passive neural stimulator 2022. In this example, the MFS 2002 may be embedded in the body of the patient, for example, subcutaneously. The embedded MFS 2002 may receive power from a detached, remote wireless battery charger 2032.

The power from the wireless battery charger 2032 to the embedded MFS 2002 may be transmitted at a frequency in the MHz or GHz range and via inductive coupling. The MFS 2002 may be embedded subcutaneously at a very shallow depth (e.g., less than 1 cm), inductive coupling to transfer energy from wireless battery charger 2032 to the embedded MFS 2002 may be feasible and efficient.

In some embodiments, the MFS 2002 may be adapted for placement at the epidural layer of a spinal column, near or on the dura of the spinal column, in tissue in close proximity to the spinal column, in tissue located near a dorsal horn, in dorsal root ganglia, in one or more of the dorsal roots, in dorsal column fibers, or in peripheral nerve bundles leaving the dorsal column of the spine.

In this embodiment, the MFS 2002 may transmit power and parameter signals to a passive TX antenna also embedded subcutaneously, which may be coupled to the RX antenna within the implanted, passive stimulation device. The power required in this embodiment is substantially lower since the TX antenna and the RX antenna are already in body tissue and there is no requirement to transmit the signal through the skin.

Figure 21:
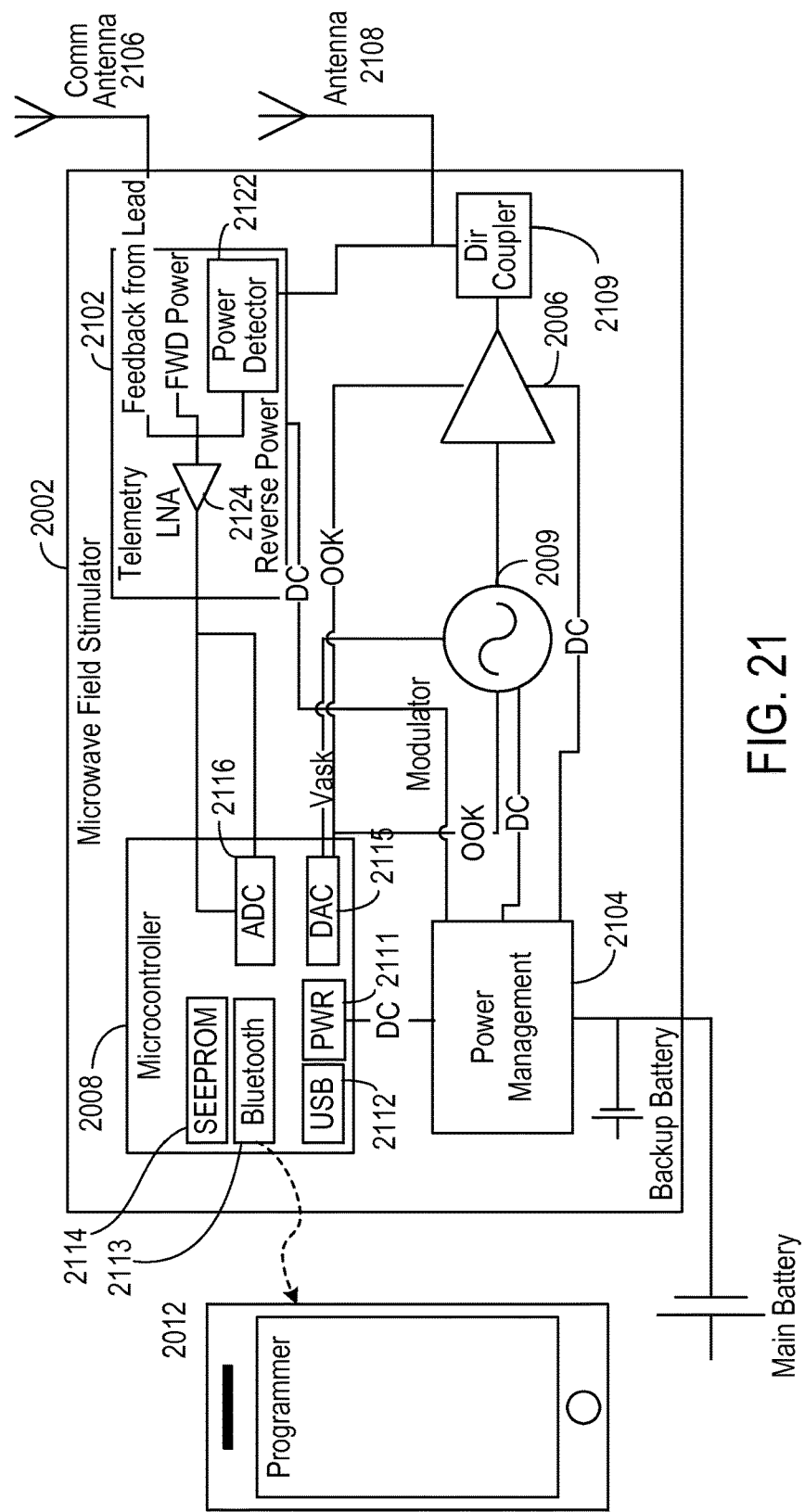
FIG. 21 is a detailed diagram of an example microwave field stimulator.

FIG. 21 is a detailed diagram of an example microwave field stimulator 2002. A microwave field stimulator 2002 may include a microcontroller 2008, a telemetry feedback module 2102, and a power management module 2104. A MFS 2002 has a two-way communication schema with a programmer 2012, as well as with a communication or telemetry antenna 2106. A MFS sends output power and data signals through a TX antenna 2108.

The microcontroller 2008 may include a storage device 2114, a bluetooth interface 2113, a USB interface 2112, a power interface 2111, an Analog to Digital convertor (ADC) 2116, and a Digital to Analog convertor (DAC) 2115. Implementations of a storage device 2114 may include non-volatile memory, such as, for example, static electrically erasable programmable read-only memory (SEEPROM) or NAND flash memory. A storage device 2114 may store waveform parameter information for the microcontroller 2008 to synthesize the output signal used by modulator 2009. The stimulation waveform may include multiple pulses. The waveform parameter information may include the shape, duration, amplitude of each pulse, as well as pulse repetition frequency. A storage device 2114 may additionally store polarity assignment information for each electrode of implantable, passive neural stimulation device 2022. The Bluetooth interface 2113 and USB interface 2112 respectively interact with either the bluetooth module 2004 or the USB module to communicate with the programmer 2012.

The communication antenna 2106 and a TX antenna 2108 may, for example, be configured in a variety of sizes and form factors, including, but not limited to a patch antenna, a slot antenna, or a dipole antenna. The TX antenna 2108 may be adapted to transmit a transmission signal to the implantable, passive neural stimulation device 2022. As discussed above, an output signal generated by the microcontroller 2008 may be used by the modulator 2009 to provide a modulated RF carrier signal. As discussed above, the RF carrier frequency can be referred to as the stimulus carrier frequency. The modulated RF carrier signal may be amplified by amplifier 2006 to generate the transmission signal. A directional coupler 2109 may be utilized to provide two-way coupling so that both the forward power of the transmission signal flow transmitted by the TX antenna 2108 and the reverse power of the reflected transmission may be picked up by power detector 2122 of telemetry feedback module 2102. In some implementations, a separate communication antenna 2106 may function as the receive antenna for receiving telemetry feedback signal from implantable, passive stimulation device 2022. In some configurations, the communication antenna may operate at a higher frequency band than the TX antenna 2108. For example, the communication antenna 2106 may have a characteristic frequency that is a second harmonic of the characteristic frequency of TX antenna 2108, as discussed above.

In some embodiments, the microwave field stimulator 2002 may additionally include a telemetry feedback module 2102. In some implementations, the telemetry feedback module 2102 may be coupled directly to communication antenna 2106 to receive telemetry feedback signals. The power detector 2122 may provide a reading of both the forward power of the transmission signal and a reverse power of a portion of the transmission signal that is reflected during transmission. The telemetry signal, forward power reading, and reverse power reading may be amplified by low noise amplifier (LNA) 2124 for further processing. For example, the telemetry module 2102 may be configured to process the telemetry feedback signal by demodulating the telemetry feedback signal to extract the encoded information. Such encoded information may include, for example, a status of implantable, passive stimulation device 2022 and one or more electrical parameters associated with a particular channel (electrode) of the implantable, passive stimulation device 2022. Based on the decoded information, the telemetry feedback module 2102 may be used to calculate an operational characteristic of implantable, passive stimulation device 2022.

Some embodiments of the MFS 2002 may further include a power management module 2104. A power management module 2104 may manage various power sources for the MFS 2002. Example power sources include, but are not limited to, lithium-ion or lithium polymer batteries. The power management module 2104 may provide several operational modes to save battery power. Example operation modes may include, but are not limited to, a regular mode, a low power mode, a sleep mode, a deep sleep/hibernate mode, and an off mode. The regular mode provides regulation of the transmission of transmission signals and stimulus to the implantable passive stimulation device 2022. In this regular mode, the telemetry feedback signal is received and processed to monitor the stimuli as normal. Low-power mode also provides regulation of the transmission of transmission signals and stimulus to the electrodes of the implantable, passive stimulation device 2022. However, under this mode, the telemetry feedback signal may be ignored. More specifically, the telemetry feedback signal encoding the stimulus power may be ignored, thereby saving MFS 2002 overall power consumption. Under sleep mode, the transceiver and amplifier 2006 are turned off, while the microcontroller is kept on with the last saved state in its memory. Under the deep sleep/hibernate mode, the transceiver and amplifier 2006 are turned off, while the microcontroller is in power down mode, but power regulators are on. Under the off mode, all transceiver, microcontroller and regulators are turned off achieving zero quiescent power.

Figure 22:
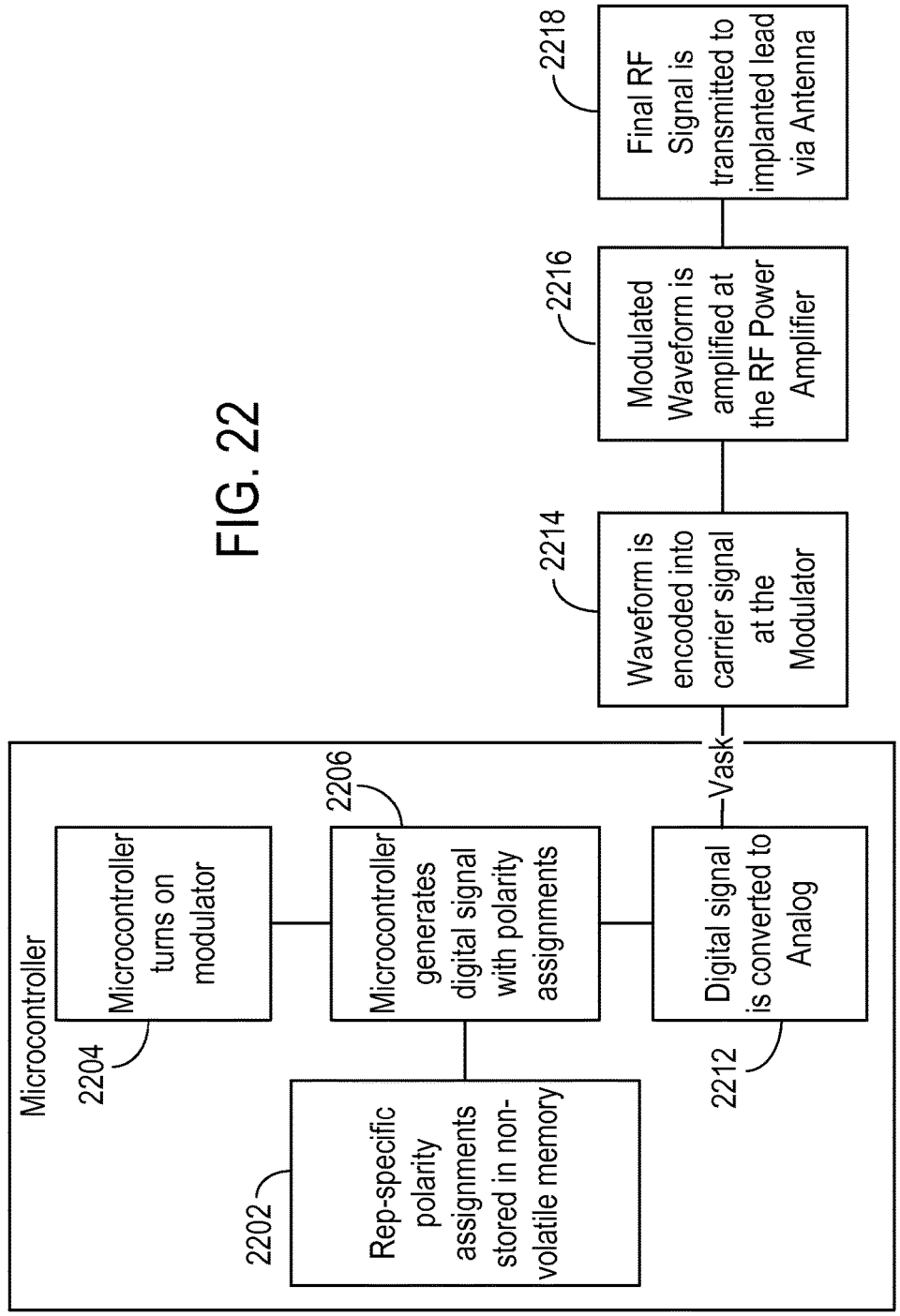
FIG. 22 is a flowchart showing an example process in which the MFS transmits polarity setting information to the implanted lead module.

FIG. 22 is a flowchart showing an example process in which the MFS 2002 transmits polarity setting information to the implantable, passive stimulation device 2022.

Polarity assignment information is stored in a non-volatile memory (2202) within the microcontroller 2008 of the MFS 2002. The polarity assignment information may be representative-specific and may be chosen to meet the specific need of a particular patient. Based on the polarity assignment information chosen for a particular patient, the microcontroller 2008 executes a specific routine for assigning polarity to each electrode of the electrode array of the implantable, passive stimulation device 2022. The particular patient has an implantable, passive stimulation device 2022 implanted, as described above.

In some implementations, the polarity assignment procedure includes sending a signal to the implantable, passive stimulation device 2022 with an initial power-on portion followed by a configuration portion that encodes the polarity assignments. The power-on portion may, for example, simply include the RF carrier signal (e.g., at the stimulus carrier frequency). The initial power-on portion has a duration that is sufficient to power-on the stimulator and allow the stimulator to reset into a configuration mode. Once in the configuration mode, the stimulator reads the encoded information in the configuration portion and sets the polarity of the electrodes as indicated by the encoded information.

Thus, in some implementations, the microcontroller 2008 turns on the modulator 2009 so that the unmodulated RF carrier is sent to the implantable, passive stimulation device 2022 (2204). After a pre-determined duration, the microcontroller 2008 automatically initiates transmitting information encoding the polarity assignment. In this scenario, the microcontroller 2008 transmits the polarity settings in the absence of handshake signals from the implantable, passive neural stimulator. Because the MFS 2002 is operating in close proximity to implantable, passive stimulation device 2022, signal degradation may not be severe enough to warrant the use of handshake signals to improve quality of communication.

To transmit the polarity information, the microcontroller 2008 reads the polarity assignment information from the non-volatile memory and generates a digital signal encoding the polarity information (2206). The digital signal encoding the polarity information may be converted to an analog signal, for example, by a digital-to-analog (DAC) converter (2212). The analog signal encoding the waveform may modulate a carrier signal at modulator 2009 to generate a configuration portion of the transmission signal (2214). The frequency of this carrier signal is the stimulus carrier frequency. This configuration portion of the transmission signal may be amplified by the power amplifier 2006 to generate the signal to be transmitted by antenna 2007 (2216). Thereafter, the configuration portion of the transmission signal is transmitted to implantable, passive neural stimulation device 2022 (2218).

Once the configuration portion is transmitted to the implantable, passive neural stimulation device 2022, the microcontroller 2008 initiates the stimulation portion of the transmission signal. Similar to the configuration portion, the microcontroller 2008 generates a digital signal that encodes the stimulation waveform. The digital signal is converted to an analog signal using the DAC. The analog signal is then used to modulate a carrier signal at modulator 2009 to generate a stimulation portion of the transmission signal. The frequency of this carrier signal is also at the stimulus carrier frequency.

In other implementations, the microcontroller 2008 initiates the polarity assignment protocol after the microcontroller 2008 has recognized a power-on reset signal transmitted by the implantable, passive stimulation device 2022. The power-on reset signal may be extracted from a feedback signal received by microcontroller 2008 from the implantable passive neural stimulator. The feedback signal may also be known as a handshake signal in that it alerts the MFS 2002 of the ready status of the implantable, passive stimulation device 2022. In an example, the feedback signal may be demodulated and sampled to digital domain before the power-on reset signal is extracted in the digital domain.

Figure 23:
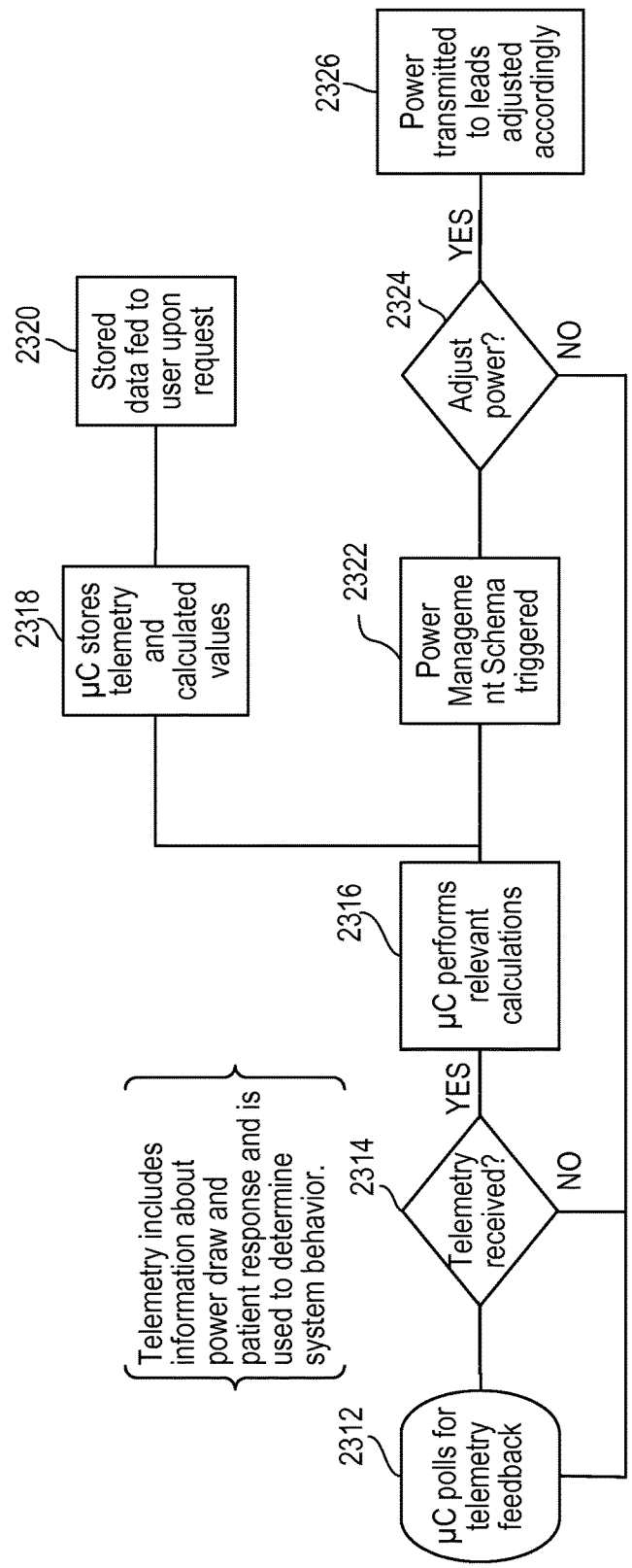
FIG. 23 is another flow chart showing an example process in which the MFS receives and processes the telemetry feedback signal to make adjustments to subsequent transmissions.

FIG. 23 is a flow chart showing an example of the process in which MFS 2002 receives and processes the telemetry feedback signal to make adjustments to subsequent transmissions.

In some implementations, the microcontroller 2008 polls the telemetry feedback module 2102 (2312). The polling is to determine whether a telemetry feedback signal has been received (2314). The telemetry feedback signal may include information based on which the MFS 2002 may ascertain the power consumption being utilized by the electrodes of the implantable, passive stimulation device 2022. This information may also be used to determine the operational characteristics of the combination system of the MFS 2002 and the neural stimulator 2022, as will be discussed in further detail in association with FIG. 24. The information may also be logged by MFS 2002 so that the response of the patient may be correlated with past treatments received over time. The correlation may reveal the patient's individual response to the treatments the patient has received up to date.

If the microcontroller 2008 determines that telemetry feedback module 2102 has not yet received telemetry feedback signal, microcontroller 2008 may continue polling (2312). If the microcontroller 2008 determines that telemetry feedback module 2102 has received telemetry feedback signal, the microcontroller 2008 may extract the information contained in the telemetry feedback signal to perform calculations (2316). The extraction may be performed by demodulating the telemetry feedback signal and sampling the demodulated signal in the digital domain. The calculations may reveal operational characteristics of the implantable, passive stimulation device 2022, including, for example, voltage or current levels associated with a particular electrode, power consumption of a particular electrode, and/or impedance of the tissue being stimulated through the electrodes.

Thereafter, in certain embodiments, the microcontroller 2008 may store information extracted from the telemetry signals as well as the calculation results (2318). The stored data may be provided to a user through the programmer upon request (2320). The user may be the patient, the doctor, or representatives from the manufacturer. The data may be stored in a non-volatile memory, such as, for example, NAND flash memory or EEPROM.

In other embodiments, a power management schema may be triggered (2322) by the microcontroller 2008. Under the power management schema, the microcontroller 2008 may determine whether to adjust a parameter of subsequent transmissions (2324). The parameter may be amplitude of the stimulation waveform or the stimulation waveform shape. In one implementation, the amplitude level may be adjusted based on a lookup table showing a relationship between the amplitude level and a corresponding power applied to the tissue through the electrodes. In one implementation, the waveform shape may be pre-distorted to compensate for a frequency response of the MFS 2002 and implantable, passive stimulation device 2022. The parameter may also be the carrier frequency of the transmission signal (known as the stimulus carrier frequency). For example, this carrier frequency of the transmission signal may be modified to provide fine-tuning that improves transmission efficiency. Detailed examples of parameter adjustment will be discussed in association with FIG. 25B.

If an adjustment is made, the subsequently transmitted transmission signals are adjusted accordingly. If no adjustment is made, the microcontroller 2008 may proceed back to polling the telemetry feedback module 2102 for telemetry feedback signal (2312).

In other implementations, instead of polling the telemetry feedback module 2102, the microcontroller 2008 may wait for an interrupt request from telemetry feedback module 2102. The interrupt may be a software interrupt, for example, through an exception handler of the application program. The interrupt may also be a hardware interrupt, for example, a hardware event and handled by an exception handler of the underlying operating system.

Figure 24:
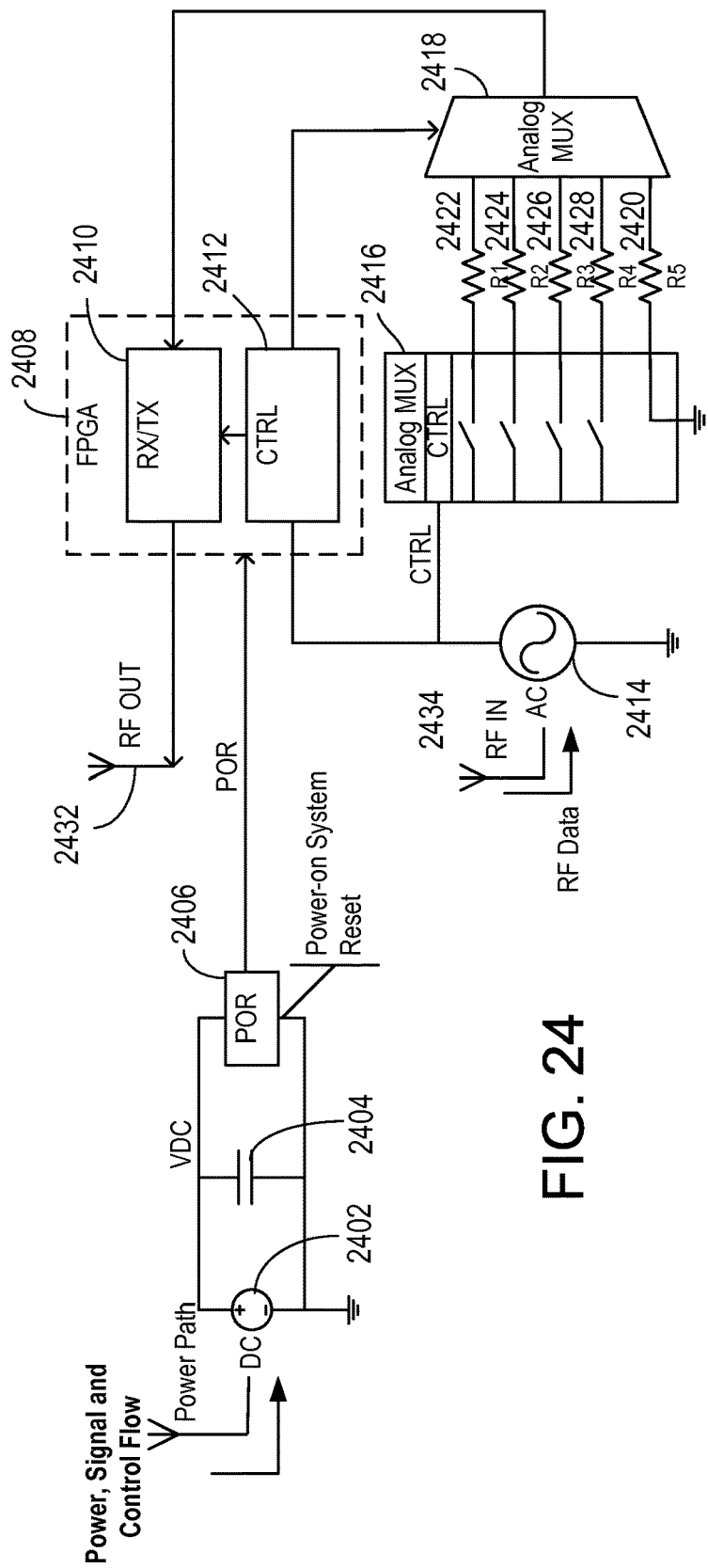
FIG. 24 is a schematic of an example implementation of power, signal and control flow on the implanted lead module.

FIG. 24 is a schematic of an example implementation of the power, signal and control flow for the implantable, passive stimulation device 2022. A DC source 2402 obtains energy from the transmission signal received at stimulation device 2022 during the initial power-on portion of the transmission signal while the RF power is ramping up. In one implementation, a rectifier may rectify the received power-on portion to generate the DC source 2402 and a capacitor 2404 may store a charge from the rectified signal during the initial portion. When the stored charge reaches a certain voltage (for example, one sufficient or close to sufficient to power operations of the implantable, passive stimulation device 2022), the power-on reset circuit 2406 may be triggered to send a power-on reset signal to reset components of the implantable, passive stimulation device 2022. The power-on set signal may be sent to circuit 2408 to reset, for example, digital registers, digital switches, digital logic, or other digital components, such as transmit and receive logic 2410. The digital components may also be associated with a control module 2412. For example, a control module 2412 may include electrode control 252, register file 1532, etc. The power-on reset may reset the digital logic so that the circuit 2408 begins operating from a known, initial state.

In some implementations, the power-on reset signal may subsequently cause circuit 2408 to transmit a power-on reset telemetry signal back to MFS 2002 to indicate that the implantable, passive stimulation device 2022 is ready to receive the configuration portion of the transmission signal that contains the polarity assignment information. For example, the control module 2412 may signal the RX/TX module 2410 to send the power-on reset telemetry signal to the RF out antenna 2432 for transmission to MFS 2002. Circuit 2408 may be an FGPA circuit.

In other implementations, the power-on reset feedback signal may not be provided. As discussed above, due to the proximity between MFS 2002 and implantable, passive stimulator device 2022, signal degradation due to propagation loss may not be severe enough to warrant implementations of handshake signals from the implantable, passive stimulation device 2022 in response to the transmission signal. In addition, the operational efficiency of implantable, passive stimulation device 2022 may be another factor that weighs against implementing handshake signals.

Once the circuit 2408 has been reset to an initial state, the circuit 2408 transitions to a configuration mode configured to read polarity assignments encoded on the received transmission signal during the configuration portion. In some implementations, the configuration portion of the transmission signal may arrive at implantable, passive stimulation device through RF in antenna 2434. The transmission signal received may provide an AC source 2414. The AC source 2414 may be at the carrier frequency of the transmission signal, for example, from about 300 MHz to about 8 GHz.

Thereafter, the control module 2412 may read the polarity assignment information and set the polarity for each electrode through the analog mux control 2416 according to the polarity assignment information in the configuration portion of the received transmission signal. The electrode interface 252 may be one example of analog mux control 2416, which may provide a channel to a respective electrode of the implantable, passive stimulation device 2022.

Once the polarity for each electrode is set through the analog mux control 2416, the implantable, passive stimulation device 2022 is ready to receive the stimulation waveforms. Some implementations may not employ a handshake signal to indicate the stimulation device 2022 is ready to receive the stimulation waveforms. Rather, the transmission signal may automatically transition from the configuration portion to the stimulation portion. In other implementations, the implantable, passive stimulation device 2022 may provide a handshake signal to inform the MFS 2002 that implantable, passive stimulation device 2022 is ready to receive the stimulation portion of the transmission signal. The handshake signal, if implemented, may be provided by RX/TX module 2410 and transmitted by RF out antenna 2432.

In some implementations, the stimulation portion of the transmission signal may also arrive at implantable, passive stimulation device through RF in antenna 2434. The transmission signal received may provide an AC source 2414. The AC source 2414 may be at the carrier frequency of the transmission signal, for example, from about 300 MHz to about 8 GHz. The stimulation portion may be rectified and conditioned in accordance with discussions above to provide an extracted stimulation waveform. The extracted stimulation waveform may be applied to each electrode of the implantable, passive stimulator device 2022. In some embodiments, the application of the stimulation waveform may be concurrent, i.e., applied to the electrodes all at once. As discussed above, the polarity of each electrode has already been set and the stimulation waveform has been applied to the electrodes in accordance with the polarity settings.

In some implementations, each channel of analog mux control 2416 is connected to a corresponding electrode and may have a reference resistor placed serially. For example, FIG. 24 shows reference resistors 2422, 2424, 2426, and 2428 in a serial connection with a matching channel. Analog mux control 2416 may additionally include a calibration resistor 2420 placed in a separate and grounded channel. The calibration resistor 2420 is in parallel connection with a given electrode on a particular channel. The reference resistors 2422, 2424, 2426, and 2428 as well as the calibration resistor 2420 may also be known as sensing resistors 1518. These resistors may sense an electrical parameter in a given channel, as discussed below.

In some configurations, an analog controlled carrier modulator may receive a differential voltage that determines the carrier frequency generated. This carrier frequency may be referred to as the feedback carrier frequency, which may be distinct from the stimulus carrier frequency associated with the transmission signal discussed earlier. The generated carrier frequency may be proportional to the differential voltage. An example analog controlled carrier modulator is VCO 1533, as discussed above in association with FIG. 15.

In one configuration, the carrier frequency may indicate an absolute voltage, measured in terms of the relative difference from a pre-determined and known voltage. For example, the differential voltage may be the difference between a voltage across a reference resistor connected to a channel under measurement and a standard voltage. The differential voltage may be the difference between a voltage across calibration resistor 2420 and the standard voltage. One example standard voltage may be the ground.

In another configuration, the feedback carrier frequency may reveal an impedance characteristic of a given channel. For example, the differential voltage may be the difference between the voltage over the electrode connected to the channel under measurement and a voltage across the reference resistor in serial connection. Because of the serial connection, a comparison of the voltage across the reference resistor and the voltage over the electrode would indicate the impedance of the electrode and the underlying tissue being stimulated relative to the impedance of the reference resistor. As the reference resistor's impedance is known, the impedance of the electrode and the underlying tissue being stimulated may be inferred based on the resulting feedback carrier frequency. Because the electrodes may only provide an insignificant contact impedance, the impedance of the electrode and the underlying tissue being stimulated may be dominated by the impedance of the underlying tissue being stimulated.

For example, the differential voltage may be the difference between a voltage over the calibration resistor and a voltage across the reference resistor. Because the calibration resistor is placed in parallel to a given channel, the voltage over the calibration is substantially the same as the voltage over the given channel. Because the reference resistor is in a serial connection with the given channel, the voltage over the reference resistor is a part of the voltage across the given channel. Thus, the difference between the voltage over the calibration resistor and the voltage across the reference resistor correspond to the voltage drop over the electrode. Hence, the voltage over the electrode may be inferred based on the voltage difference.

In yet another configuration, the feedback carrier frequency may provide a reading of a current. For example, if the voltage over reference resistor 2422 has been measured, as discussed above, the current going through reference resistor and the corresponding channel may be inferred by dividing the measured voltage by the impedance of reference resistor 2422.

Many variations may exist in accordance with the specifically disclosed examples above. The examples and their variations may sense one or more electrical parameters concurrently and may use the concurrently sensed electrical parameters to drive an analog controlled modulator device. The resulting carrier frequency varies with the differential of the concurrent measurements. This carrier frequency may be referred to as the feedback carrier frequency for transmitting the telemetry feedback signal to MFS 2002. The telemetry feedback signal may include a signal at the resulting feedback carrier frequency.

The MFS 2002 may determine the feedback carrier frequency variation by demodulating at a fixed frequency and measure phase shift accumulation caused by the feedback carrier frequency variation. Generally, a few cycles of RF waves at the resulting feedback carrier frequency may be sufficient to resolve the underlying feedback carrier frequency variation. The determined variation may indicate an operation characteristic of the implantable, passive stimulation device 2022. The operation characteristics may include an impedance, a power, a voltage, a current, etc. The operation characteristics may be associated with an individual channel. Therefore, the sensing and feedback carrier frequency modulation may be channel specific and applied to one channel at a given time. Consequently, the telemetry feedback signal may be time shared by the various channels of the implantable, passive stimulation device 2022.

In one configuration, the analog MUX 2418 may be used by the controller module 2412 to select a particular channel in a time-sharing scheme. The sensed information for the particular channel, for example, in the form of a carrier frequency modulation, may be routed to RX/TX module 2410. Thereafter, RX/TX module 2410 transmits, through RF out antenna 2432, to the MFS 2002, the telemetry feedback encoding the sensed information for the particular channel.

Figure 25A:
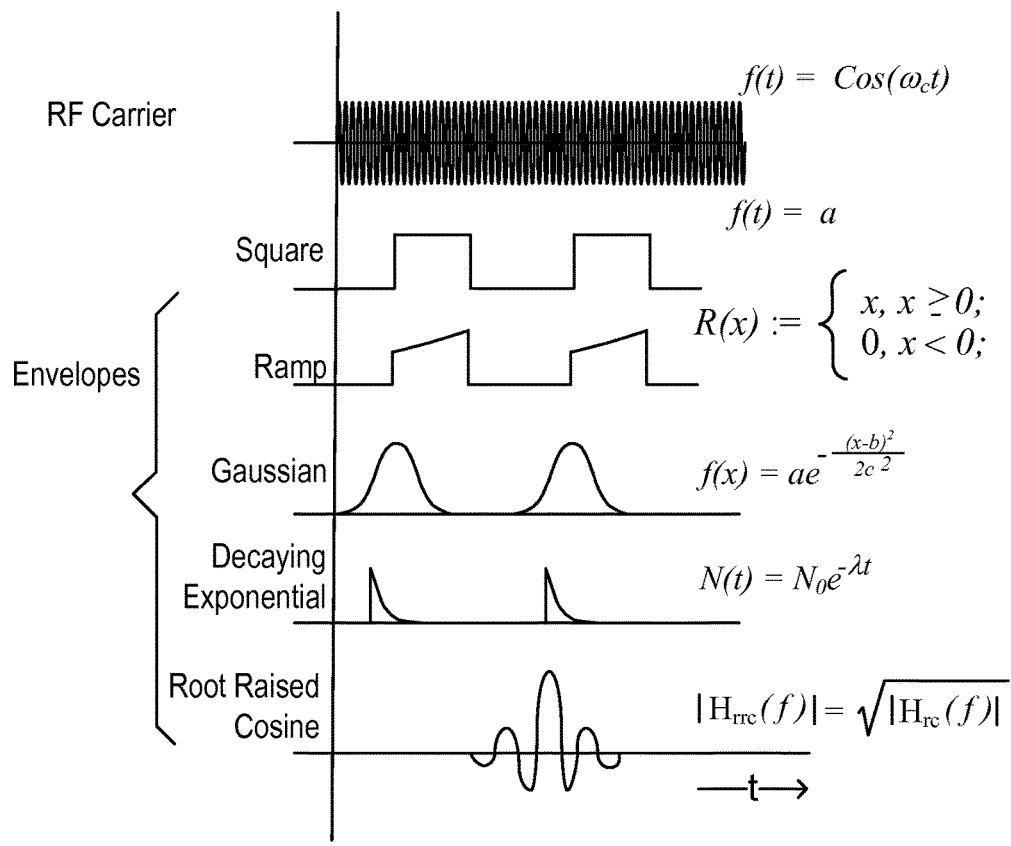
FIG. 25A shows an example RF carrier wave and example envelope waveforms suitable for use as stimulation waveforms.

FIG. 25A shows an example RF carrier wave and example envelope waveforms suitable for use as stimulation waveforms. The frequency of this RF carrier wave may be known as the stimulus carrier frequency, as discussed earlier. The top panel shows an example waveform corresponding to the RF carrier. As discussed above, the RF carrier may be in a microwave band with a center frequency from about 300 MHz to about 8 GHz. The remaining panels show example envelope waveforms suitable to be used as stimulation waveforms. Examples include, but are not limited to, a square wave, a Gaussian waveform, a decaying exponential waveform, a root raised cosine waveform. The envelope waveform may modulate the RF carrier (at the stimulus carrier frequency) to generate to generate an output signal to feed the power amplifier 2006. This modulated and amplified signal correspond to a stimulation portion of a transmission signal. The implantable, passive neural stimulator may decoded the received transmission signal to extract the stimulation waveform by rectifying the transmission signal and conditioning the rectified signal, as discussed above.

Figure 25B:
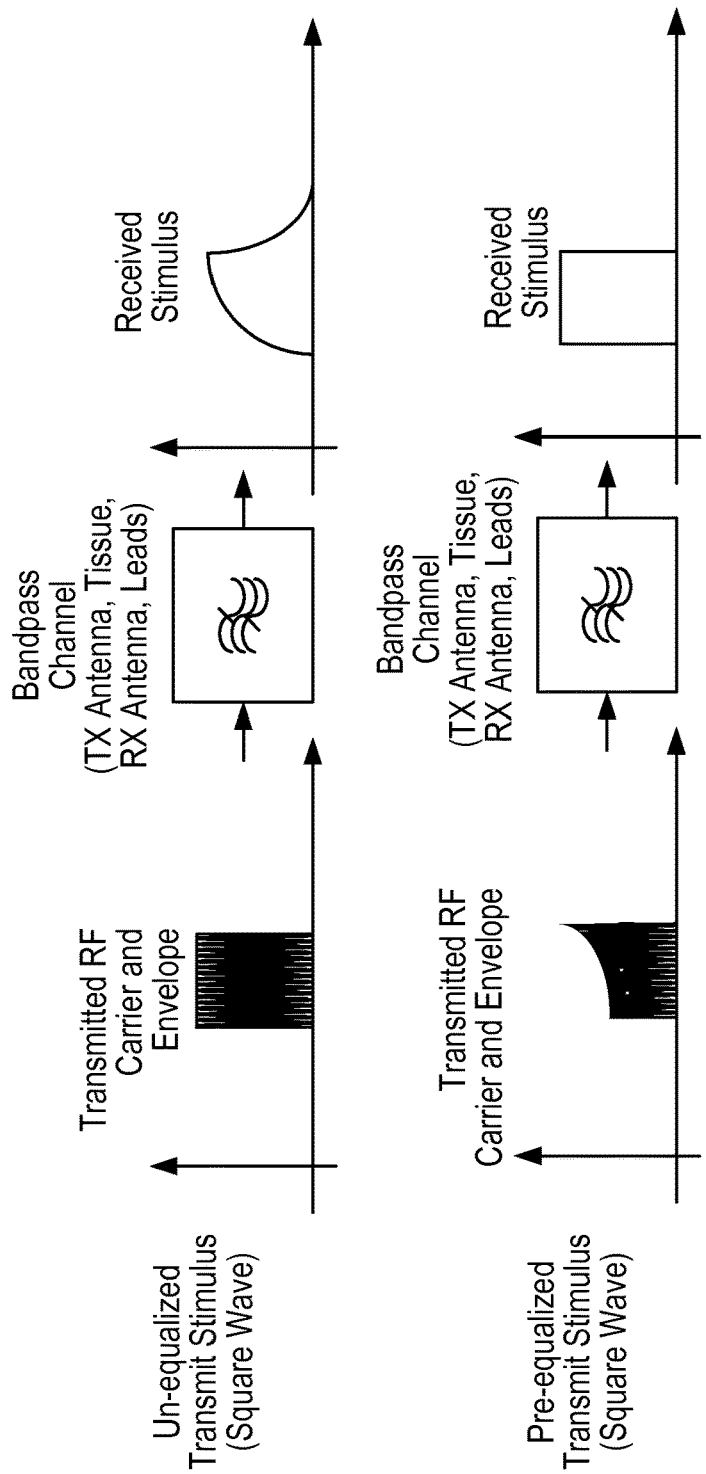
FIG. 25B shows an example pre-distorted stimulation waveform to offset distortions caused by the MFS and the implanted lead module as well as the impedance characteristic of the tissue being stimulated.

FIG. 25B shows an example of pre-distorted stimulation waveform to offset distortions caused by the MFS 2002 and the implantable, passive stimulation device 2022 as well as the impedance characteristic of the tissue being stimulated. The top panel shows an example of an un-equalized transmission signal modulated by a square waveform. To reach the electrodes, the transmission signal generally undergoes the transmission from the antenna 2007 on MFS 2002, the propagation through skin and underlying tissue, the reception by the RX antenna 2023 of the implantable, passive stimulation device 2022, and the application at the electrodes with a frequency response. The combined effect amounts to a band pass characteristic in the frequency domain. A resulting actual stimulus applied may deviate substantially from the intended waveform shape, as shown in the top panel of FIG. 25B.

To compensate for this band pass effect, the stimulation waveform may be pre-distorted. The pre-distortion may be based on the inverse frequency response of the band pass effect. By imposing the inverse frequency response to provide a pre-distorted waveform shape, the received stimulation waveform at the implantable, passive stimulation device 2022 may match the desired waveform shape. The bottom panel of FIG. 25B shows a pre-equalized transmission signal modulated by a pre-distorted square waveform. As illustrated, the pre-equalized transmission signal can offset the band pass effect so that the actual stimulus applied may substantially match the intended square waveform shape.

In some implementations, the pre-equalization may be applied based on information in the telemetry feedback signal from the implantable, passive stimulation device 2022. In other implementations, the amplitude or frequency of the transmission signal may be adjusted based on the information in the telemetry signal, as discussed above in association with FIG. 23.

In one configuration, the amplitude may be adjusted according to data stored in a table on the MFS 2002. The table may, for example, provide a chart showing, for a desired power output at the electrodes, the corresponding amplitude of the transmission signal. The amplitude of the transmission may be increased if the calculated power is below the desired power in accordance with the chart. Likewise, the amplitude of the transmission may be reduced if the calculated power is above the desired power.

In another configuration, the stimulus carrier frequency may be adjusted so that the transmission signal may be better tuned to the combined band pass effect as discussed above. The adjustment may be in the megahertz range, for example, up to 10 MHz, to provide fine tuning to the carrier frequency. The fine tuning may improve the efficiency of transmitting the stimulation portion of the transmission signal from MFS 2002 to implantable, passive stimulation device 2022. In certain situations, patient body movement during a treatment session may necessitate such fine tuning to maintain substantially identical stimulus over the treatment session.

FIG. 26
is a timing diagram showing example waveforms during the initial portion and the subsequent configuration portion of a transmission signal received at the implantable, passive stimulation device 2022. The top panel 2602 shows an example waveform corresponding to the RF carrier transmitted by the MFS 2002. As discussed above, the RF carrier may be in a microwave band with a center frequency from about 300 MHz to about 8 GHz.

Panel 2604 shows the power supply received at implantable, passive neural stimulation device 2022. The initial portion corresponds to a power ramp-up. When implantable, passive neural stimulation device 2022 has received enough power for operation, a power-on event signal may be generated by a power-on reset circuit 2406. The power-on reset signal, shown in panel 2606, may be used to reset the component son the stimulation device 2022 as described above.

Thereafter, the stimulation device 2022 is ready to receive the configuration portion. Panel 2608 shows example waveforms received by implantable, passive stimulation device 2022 during the configuration portion. The configuration portion may include N data cycles to encode the polarity assignment information for each channel of the implantable, passive neural stimulation device 2022. In some implementations, for a particular channel, the configuration portion may contain several data cycles to encode the channel identification information. The configuration portion may contain additional data cycles to encode the polarity assignment of the particular channel. In some implementations, the waveform edges may be used to encode the channel identification information and the corresponding polarity assignment information for the channel. For example, the rising edge may denote a "1" while the falling edge may denote a "0." Edge triggered encoding may be more robust than static level encoding for transmitting the polarity assignment information. The channel identification information and the corresponding polarity assignment information may then be stored, for example, in register file 1532. Controller module 2412 may set the polarity of a particular channel according to the information stored in the register file 1532, as discussed above and indicated by panel 2610.

Thus, the polarity assignment information of each channel may be maintained persistent at the implantable passive stimulation device 2022 by providing the information during the configuration portion of a transmission signal before a stimulation is subsequently applied according to the assigned polarity.

Figure 27:
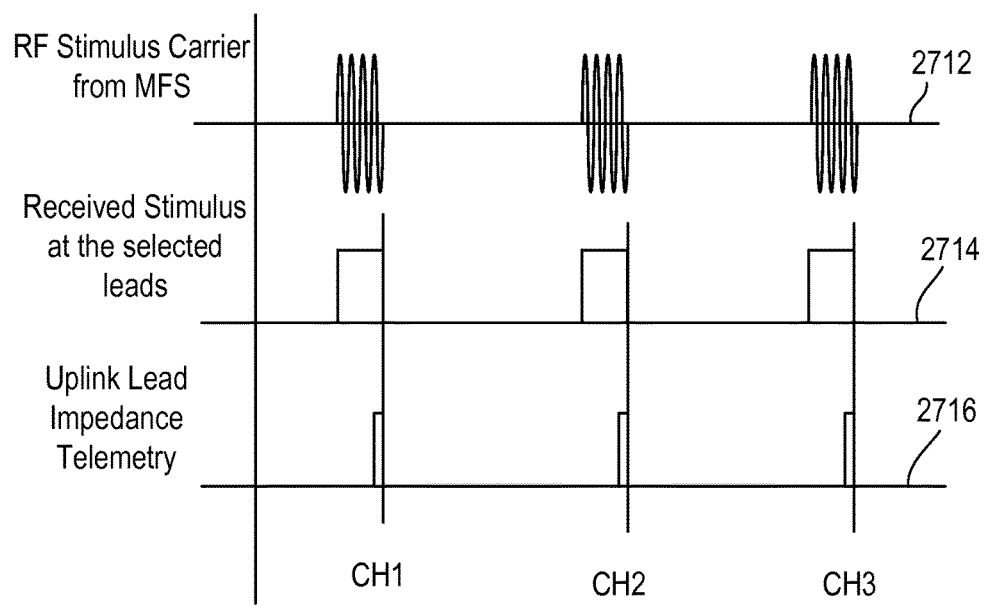
FIG. 27 is a timing diagram showing example waveforms during the final stimulation portion of the transmission signal received at the implantable, passive stimulation device.

FIG. 27 is a timing diagram showing example waveforms during the final stimulation portion of the transmission signal received at the implantable, passive stimulation device 2022. As discussed above, a transmission signal may include an initial portion containing energy to power up the implantable, passive stimulation device 2022, a subsequent configuration portion containing polarity assignment information for implantable, passive stimulation device 2022 to set the polarities of the electrodes. Panel 2712 illustrates the RF carrier modulated by the stimulation waveform, as synthesized by microcontroller 2008 and modulator 2009 and then amplified by amplifier 2006. The stimulation portion of the received transmission signal may be rectified and conditioned to provide the received stimulation waveform, as shown in panel 2714. The envelope detection is performed at the implantable passive stimulation device 2022, as discussed above. At the end of each stimulation waveform, a telemetry feedback signal may be provided by the implantable, passive stimulation device 2022 in accordance with discussions above. The timing of when the telemetry signal is provided and transmitted to MFS 2002 is illustrated in panel 2716. As discussed above, the telemetry signal may provide information of an operation characteristic of one channel at a given time instant. For example, panel 2716 shows channels 1 through 3 are being measured individually and the corresponding telemetry feedback signal is provided on a time-sharing basis.

Figure 28:
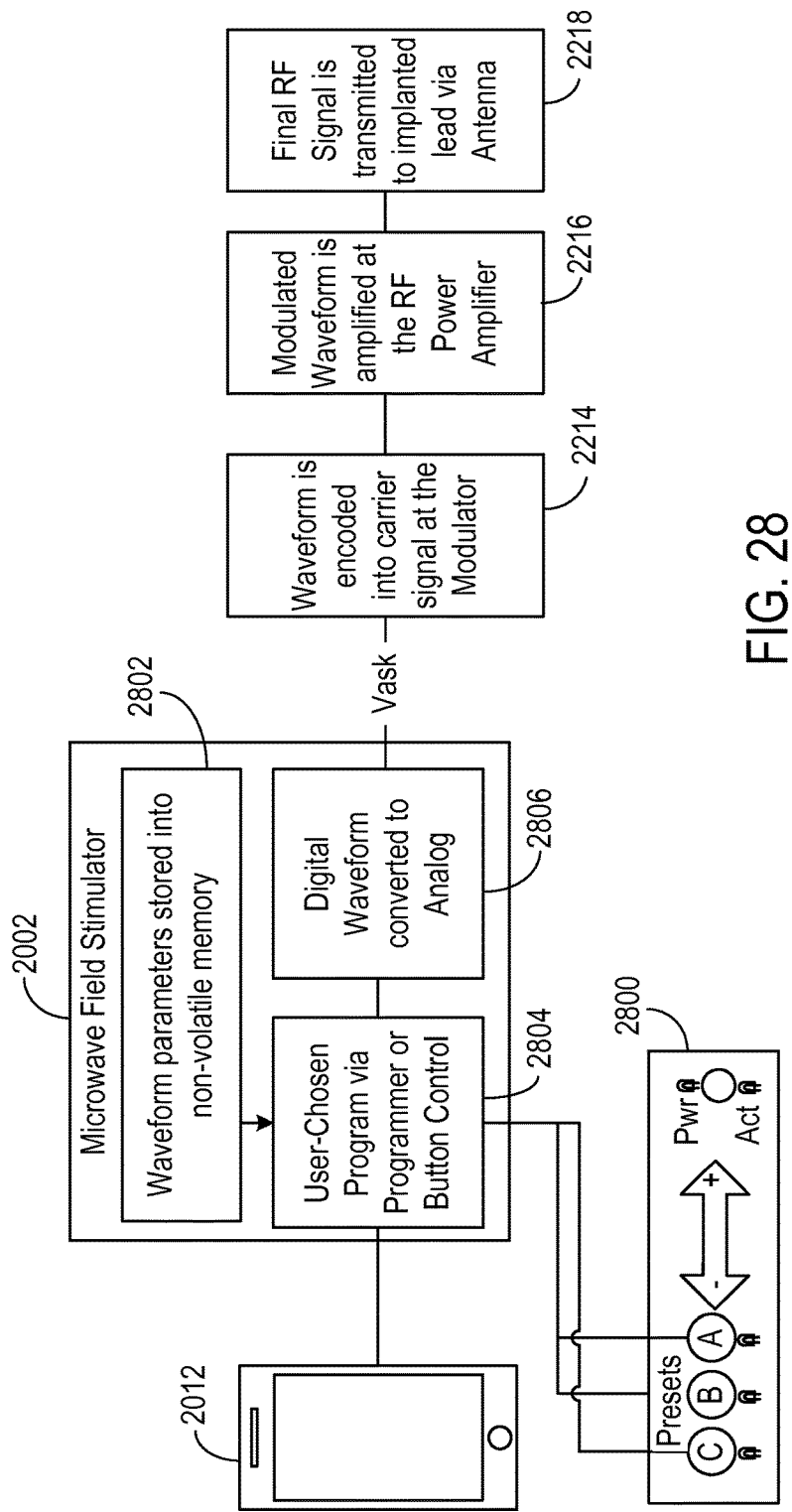
FIG. 28 is a block diagram illustrating an example in which a user programs the stimulation waveform to be embedded in the signal sequence for transmission to the implanted lead module.

FIG. 28 is a block diagram illustrating an example in which a user programs the stimulation waveform to be embedded in the signal sequence for transmission to the implantable, passive stimulation device 2022. The programmer 2012 may be a mobile computing device. The programmer 2012 may communicate with the MFS 2002 via, for example, blue-tooth or USB. The user may authenticate him or herself to the MFS before he can access data on the MFS 2002 or modify existing settings on the MFS 2002. The communication may also be encrypted.

A user may modify a setting of the MFS 2002 by, for example, choosing a preset program or using a button control (2804). A user of the programmer 2012 may be presented with a user interface (UI) 2800. The UI 2800 may be a visual programming interface to provide easy access to programming capabilities. The UI 2800 may provide a collection of preset programs that the user may choose to apply to his treatment. The preset programs A, B, and C may be provided by the manufacturer as treatment protocols in compliance with any regulatory provisions. The preset programs may prescribed by an attending physician as the treatment plans most likely to be efficacious for the user/patient. The UI 2008 may also provide a button for the user/patient to adjust a power level of the stimuli to be or being applied.

In some implementations, the UI 2800 may provide debouncing in response to user inputs. After receiving user selections as made on the UI 2008, waveform parameters stored in a non-volatile memory may be activated (2802) so that the micro-controller 2008 may synthesize an output signal based on the waveform parameters. The synthesized output signal may be converted into an analog signal (2806). As discussed above, the analog signal may modulate a carrier frequency to provide a modulated signal (2216), the modulated signal may be subsequently amplified by amplifier 2006 (2216), and the amplified signal may be transmitted from the MFS 2002 to the implantable, passive stimulation device 2022 (2218).

Figure 29A:
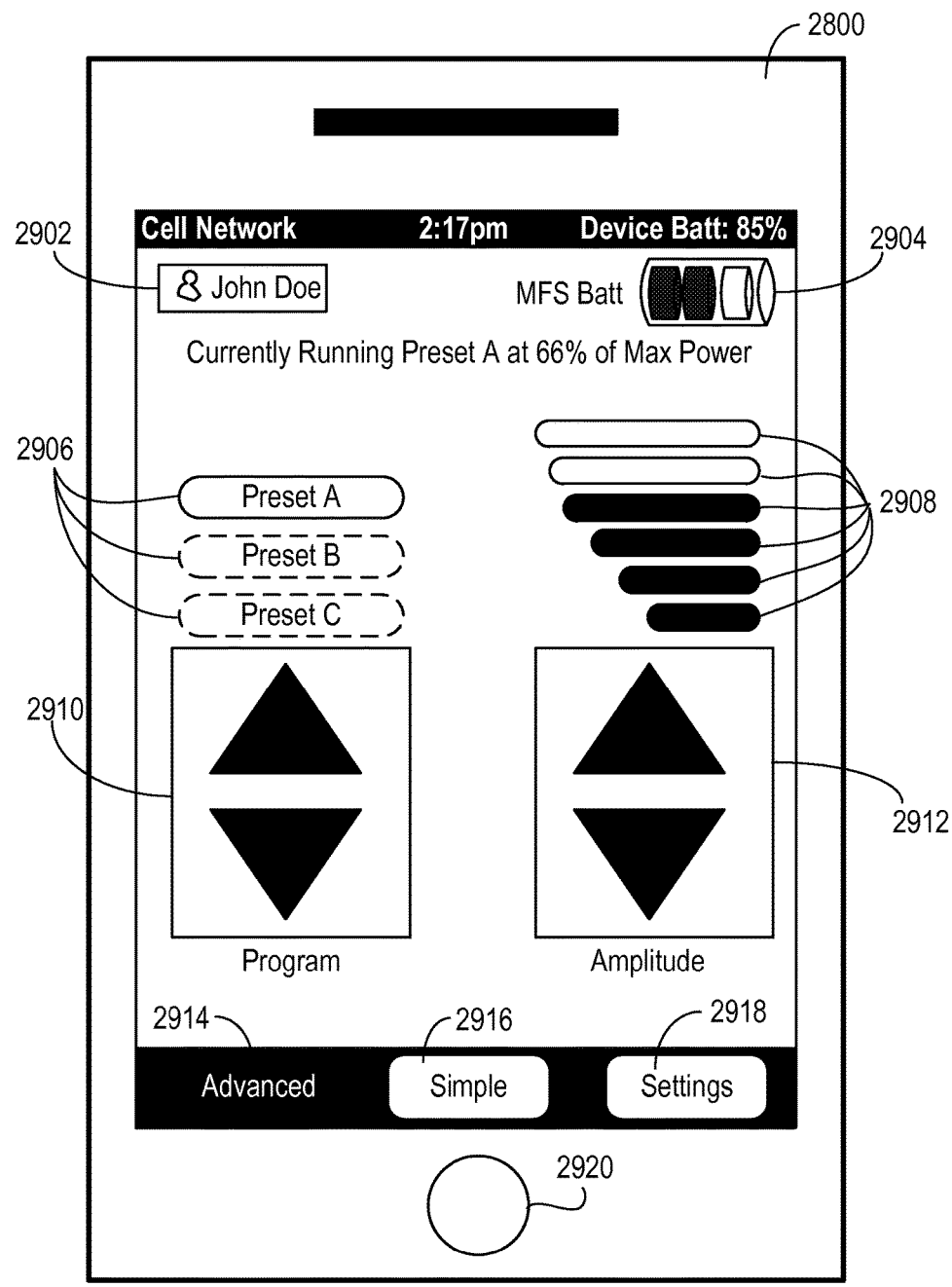
FIG. 29A shows an example user interface for the user to program the stimulation waveform.

FIG. 29A shows an example UI 2800 for the user to program the stimulation waveform. The UI 2800 may include a name label 2902 indicating the name of the patient registered to MFS 2002, a battery indicator 2904, a menu of preset programs 2906 for the user to choose from, bar indicators 2908 to indicate the amplitude or power of the stimuli, program button 2910 for the user to scroll through the menu of preset programs 2906, and an amplitude button 2912 for the user to adjust the amplitude or power of the stimuli. The UI 2800 may additionally include an advanced button for the user to access advanced or more sophisticated options of programming MFS 2002, a simple button for the user to access standard options of programming MFS 2002, an a settings button for the user to change settings on MFS 2002. The UI 2800 of FIG. 29A corresponds to a UI under the advanced option. The UI 2800 may further include power button 2920 to power on or off MFS 2002.

Figure 29B:
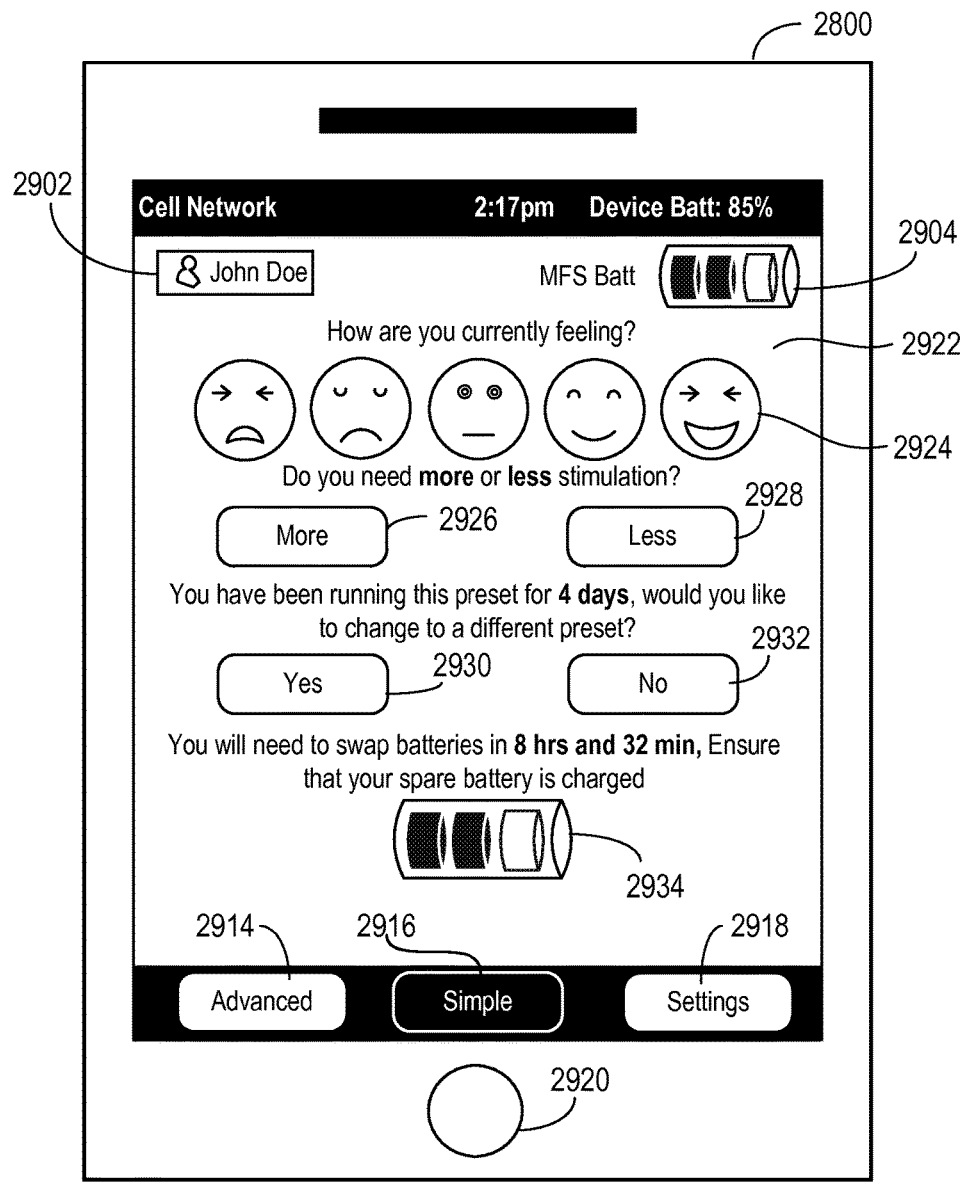
FIG. 29B shows another example user interface for the user to program the stimulation waveform.

FIG. 29B shows another example UI 2800 for the user to program the stimulation waveform. UI 2800 of FIG. 29B correspond to the UI after the simple option is selected. The UI 2800 may include an interactive questionnaire 2922 for the user to supply information of the user's current feeling and past treatment history. Questionnaire 2922 may include icon bar 2924 to guide the user to convey the user's need for more (2926) or less (2928) stimulation. Questionnaire 2922 may also include button 2930 and button 2932 to convey the user's desire to change to a different preset program. Questionnaire may additionally include an indicator 2934 to notify the user of battery power status.

A number of implementations have been described. Nevertheless, it will be understood that various modifications may be made. Accordingly, other implementations are within the scope of the following claims.

What is claimed is:

1. A system, comprising:
an implantable passive stimulation device that does not have its own independent power source, the implantable passive stimulation device comprising one or more stimulation electrodes, a power-on reset circuit, control logic, stimulation circuitry, and a receiving antenna;
a controller module comprising:
a storage device configured to store parameters defining a stimulation waveform and polarity assignments for the stimulation electrodes of the implantable passive stimulation device;
a controller configured to generate, based on the stored parameters and polarity assignments, an output signal that includes an initial power-on portion followed by a configuration portion that encodes the polarity assignments followed by a stimulation portion that includes the stimulation waveform, wherein the stimulation portion is generated by modulating an envelope waveform on a carrier wave;
one or more antennas configured to transmit, in repeated cycles, the output signal non-inductively to the receiving antenna on the implantable passive stimulation device to generate power sufficient for electrodes on the implantable passive stimulation device to stimulate surrounding excitable tissue when the implantable passive stimulation device is implanted inside a patient such that for each particular repetition cycle of the output signal, (i) a power-on reset signal that resets the control logic is generated from the power-on portion of the received output signal, (ii) the polarity assignment information is decoded from the configuration portion of the received output signal to set the polarities for the stimulation electrodes, and (iii) electrical pulses are generated by demodulating the stimulation portion of the output signal to extract the stimulation waveform and then applied, using power generated from the output signal received non-inductively inside the patient, to excitable tissue according to the polarity assignment information decoded from the configuration portion that precedes the stimulation portion of the particular repetition cycle.

2. The system of claim 1, wherein the controller module is configured to read a telemetry feedback signal from the implantable passive stimulation device, the telemetry feedback signal generated by solely using the output signal of the particular repetition cycle to power the implantable passive stimulator device to cause the implantable passive stimulator device to:
sense a first electrical parameter and a second electrical parameter concurrently; and
compare the first electrical parameter and the second electrical parameter to generate an analog feedback carrier frequency signal with a feedback carrier frequency that is proportional to a difference between the first electrical parameter and the second electrical parameter.

3. The system of claim 2, wherein the controller module powers the implantable passive stimulation device to cause the telemetry feedback signal to be generated based on the first and second electrical parameters for which the first electrical parameter is a voltage over a reference resistor placed in serial connection with the electrode, and the second electrical parameter is a voltage over the electrode.

4. The system of claim 3, wherein the controller module powers the implantable passive stimulation device to cause the telemetry feedback signal to be generated such that the feedback carrier frequency is proportional to a difference between a voltage over the reference resistor and a voltage over the electrode.

5. The system of claim 2, wherein the controller module powers the implantable passive stimulation device to cause the telemetry feedback signal to be generated based on the first and second electrical parameters for which the first electrical parameter is a voltage over a reference resistor placed in serial connection with the electrode, and the second electrical parameter is a voltage over a calibration resister placed in parallel connection with the electrode.

6. The system of claim 5, wherein the controller module powers the implantable passive stimulation device to cause the telemetry feedback signal to be generated such that the feedback carrier frequency is proportional to a difference between a voltage over the reference resistor and the voltage over the calibration resistor.

7. The system of claim 2, wherein the controller module powers the implantable passive stimulation device to cause the telemetry feedback signal to be generated based on the first and second electrical parameters for which the first electrical parameter corresponds to a fixed voltage and the second electrical parameter is a voltage over one of: a calibration resistor, a reference resistor, an electrode.

8. The system of claim 1, wherein the controller module powers the implantable passive stimulation device such that the power-on signal causes a handshake signal to be transmitted from implantable passive stimulation device to the controller module, the handshake signal confirms to the controller module that the implantable passive stimulation device is ready to receive polarity setting information.

9. The system of claim 1, wherein the controller module powers the implantable passive stimulation device such that a handshake signal is received from the implantable passive stimulation device when the polarities for the electrodes are set according to the polarity assignment information encoded in the configuration portion, the handshake signal confirms to the controller module that the implantable, passive stimulator is ready to receive the stimulation portion of the output signal.

* * * * *